US012662678B2

(12) United States Patent
Sierks et al.

(10) Patent No.: US 12,662,678 B2
(45) Date of Patent: Jun. 23, 2026

(54) BINDING MOLECULE BINDING TO TRAUMATIC BRAIN INJURY-ASSOCIATED TAU AND METHODS OF USE THEREOF

(71) Applicant: ARIZONA BOARD OF REGENTS ON BEHALF OF ARIZONA STATE UNIVERSITY, Scottsdale, AZ (US)

(72) Inventors: Michael Sierks, Fort McDowell, AZ (US); Lalitha Venkataraman, Tempe, AZ (US); Wei Xin, Tempe, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 711 days.

(21) Appl. No.: 18/085,418

(22) Filed: Dec. 20, 2022

(65) Prior Publication Data

US 2023/0220401 A1 Jul. 13, 2023

Related U.S. Application Data

(63) Continuation of application No. 16/712,652, filed on Dec. 12, 2019, now Pat. No. 11,549,113, which is a continuation of application No. 16/400,894, filed on May 1, 2019, now abandoned, which is a continuation of application No. 16/060,880, filed as application No. PCT/US2016/065908 on Dec. 9, 2016, now abandoned.

(60) Provisional application No. 62/266,461, filed on Dec. 11, 2015.

(51) Int. Cl.

| | |
|---|---|
| *A61K 39/395* | (2006.01) |
| *A61K 39/00* | (2006.01) |
| *A61K 49/00* | (2006.01) |
| *A61K 49/16* | (2006.01) |
| *A61P 25/28* | (2006.01) |
| *C07K 1/22* | (2006.01) |
| *C07K 14/00* | (2006.01) |
| *C07K 14/435* | (2006.01) |
| *C07K 14/47* | (2006.01) |
| *C07K 16/00* | (2006.01) |
| *C07K 16/18* | (2006.01) |
| *C12N 15/62* | (2006.01) |
| *G01N 33/48* | (2006.01) |
| *G01N 33/483* | (2006.01) |
| *G01N 33/487* | (2006.01) |
| *G01N 33/50* | (2006.01) |
| *G01N 33/53* | (2006.01) |
| *G01N 33/569* | (2006.01) |
| *G01N 33/68* | (2006.01) |
| *C07K 16/28* | (2006.01) |

(52) U.S. Cl.
CPC .......... *C12N 15/62* (2013.01); *A61K 39/0005* (2013.01); *A61K 39/0007* (2013.01); *A61K 39/395* (2013.01); *A61P 25/28* (2018.01); *C07K 1/22* (2013.01); *C07K 14/00* (2013.01); *C07K 14/435* (2013.01); *C07K 14/4711* (2013.01); *C07K 16/00* (2013.01); *C07K 16/18* (2013.01); *G01N 33/48* (2013.01); *G01N 33/483* (2013.01); *G01N 33/487* (2013.01); *G01N 33/50* (2013.01); *G01N 33/5005* (2013.01); *G01N 33/5058* (2013.01); *G01N 33/53* (2013.01); *G01N 33/56966* (2013.01); *G01N 33/68* (2013.01); *G01N 33/6854* (2013.01); *G01N 33/6857* (2013.01); *G01N 33/6869* (2013.01); *G01N 33/6896* (2013.01); *C07K 16/2872* (2013.01); *C07K 2317/24* (2013.01); *C07K 2317/54* (2013.01); *C07K 2317/56* (2013.01); *C07K 2317/569* (2013.01); *C07K 2317/62* (2013.01); *C07K 2317/622* (2013.01); *G01N 2333/435* (2013.01); *G01N 2333/4709* (2013.01); *G01N 2800/00* (2013.01); *G01N 2800/28* (2013.01); *G01N 2800/2814* (2013.01); *G01N 2800/2821* (2013.01); *G01N 2800/2871* (2013.01)

(58) Field of Classification Search
CPC ............ A61K 2039/505; A61K 39/395; C07K 2317/569; C07K 14/47; C07K 2317/55; C07K 16/00; C07K 14/4711; C07K 2317/54; A61P 25/28; A61P 25/00
See application file for complete search history.

(56) References Cited

U.S. PATENT DOCUMENTS

| | | | | |
|---|---|---|---|---|
| 10,695,406 | B2 * | 6/2020 | McGuckin ............. | C07K 14/54 |
| 2011/0143375 | A1 | 6/2011 | Wang et al. | |
| 2012/0087919 | A1 | 4/2012 | Schneider | |
| 2015/0004169 | A1 | 1/2015 | Kayed et al. | |
| 2022/0281943 | A1 | 9/2022 | Bluestone | |

FOREIGN PATENT DOCUMENTS

| | | | | |
|---|---|---|---|---|
| CN | 104498501 A | 4/2015 | | |
| CN | 104926940 A | 9/2015 | | |
| WO | WO-2010096930 A1 * | 9/2010 | ............. | C07K 16/28 |
| WO | WO-2014059442 A2 | 4/2014 | | |

(Continued)

OTHER PUBLICATIONS

MacCallum et al., J. Mol. Biol., 1996; 262: 732-745.*

(Continued)

*Primary Examiner* — Chang-Yu Wang
(74) *Attorney, Agent, or Firm* — Riverside Law LLP

(57) ABSTRACT

The present invention provides detection reagents and method for determining risk of traumatic brain injury (TBI) and/or susceptibility to neurodegenerative disease in a subject.

14 Claims, 7 Drawing Sheets

Specification includes a Sequence Listing.

(56) References Cited

FOREIGN PATENT DOCUMENTS

WO      WO-2015081085 A2     6/2015
WO      WO-2015179918 A1  *  12/2015   ................ A61P 5/50

OTHER PUBLICATIONS

Pascalis et al., The Journal of Immunology, 2002; 169: 3076-3084.*
Casset et al., BBRC, 2003; 307: 198-205.*
Vajdos et al., J. Mol. Biol. 2002; 320: 415-428.*
Holm et al., Mol. Immunol., 2007; 44: 1075-1084.*
Chen et al., J. Mol. Bio., 1999; 293: 865-881.*
Wu et al., J. Mol. Biol., 1999; 294:151-162.*
Burgess et al. J of Cell Bio. 1990, 111:2129-2138.*
Bowie et al. Science, 1990, 247:1306-1310.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
Rudikoff et al., Proc. Natl. Acad. Sci. USA 1982 vol. 79: p. 1979.*
Albayram, et al., "Function and Regulation of TAU conformations in the development and treatment of traumatic brain injury and neurodegeneration", Cell & Bioscience 6(59), 6 pages (2016).
Chen "Enhancement and destruction of antibody function by somatic mutation: unequal occurrence is controlled by V gene combinatorial associations" EMBO 14(12):2784-2794 (Year: 1995).
Google.com—machine translation of CN 104926940—accessed on Feb. 24, 2022 (Year: 2015).
Kenkel "What is an scFv?" accessed from blog.addgene.org on Feb. 24, 2022 (Year: 2021).
Kondo, et al., "cis p-tau: early driver of brain injury and tauopathy blocked by antibody", Nature 523 (7561), 431-436 (2015).
Kussie "A Single Engineered Amino Acid Substitution Changes Antibody Fine Specificity" J Immunol 152(1): 146-52 (Year: 1994).
Muyldermans "a guide to: generation and design of nanobodies" FEBS 288:2084-2102 (Year: 2021).
Patent Cooperation Treaty, International Searching Authority, Search Report and Written Opinion for PCT/US2016/065908, 12 pages, Apr. 28, 2017.
Wikipedia "Single-domain antibody" accessed from wikipedia.org on Feb. 24, 2022 (Year: 2022).

* cited by examiner

AD Patient                                        ND control Patient

AD Sample    ND Sample 70 kd
50 kd 35 kd
25 kd

Phosphorylated tau AT8

5μm

2μm

Binding to BSA (round 1) at 20μm        Binding to BSA (round 34) at 20μm

2μm

5μm

Binding to aggregated α-syn          Binding to aggregated α-syn
(round 1) at 20μm                    (round 12) at 20μm Binding to AD Braak I tissue
(round 1) at 5µm Binding to Braak I tissue
(round 15) at 5µm Binding to AD Braak I tau IP
(round 1) at 5µm Binding to Braak I tau IP
(round 8) at 5µm

SEQUENCE LISTING

```
Sequence total quantity: 57
SEQ ID NO: 1              moltype = DNA  length = 912
FEATURE                   Location/Qualifiers
variation                 7
                          note = a, c, t, g, unknown or other
variation                 28
                          note = a, c, t, g, unknown or other
variation                 41
                          note = a, c, t, g, unknown or other
variation                 59
                          note = a, c, t, g, unknown or other
variation                 68
                          note = a, c, t, g, unknown or other
variation                 71
                          note = a, c, t, g, unknown or other
source                    1..912
                          mol_type = other DNA
                          organism = synthetic construct
SEQUENCE: 1
gattacngcc aagcttgcat gcaaattnta tttcaaggag ncagtcataa tgaaatacnt   60
attgcctncg ncagccgctg gattgttatt actcgcggcc cagccggcca tggccgaggt  120
gcagctgttg gagtctgggg gaggcttggt acagcctggg gggtccctga gactctcctg  180
tgcagcctct ggattcacct ttagcagcta tgccatgagc tgggtccgcc aggctccagg  240
gaaggggctg gagtgggtct catctatttc ttctaatggt gatgatacag cttacgcaga  300
ctccgtgaag ggccggttca ccatctccag agacaattcc aaggacacgc tgtatctgca  360
aatgaacagc ctgagagccg aggacacggc cgtatattac tgtgcgaaag ctaataattc  420
```

```
ttttgactac tggggccagg gaaccctggt caccgtctcg agcggtggag gcggttcagg  480
cggaggtggc agcggcggtg gcgggtcgac ggacatccag atgacccagt ctccatcctc  540
cctgtctgca tctgtaggag acagagtcac catcacttgc cgggcaagtc agagcattag  600
cagctattta aattggtatc agcagaaacc agggaaagcc cctaagctcc tgatctataa  660
tgcatccact ttgcaaagtg gggtcccatc aaggttcagt ggcagtggat ctgggacaga  720
tttcactctc accatcagca gtctgcaacc tgaagatttt gcaacttact actgtcaaca  780
ggatagtgct actccttata cgttcggcca agggaccaag gtggaaatca aacgggcggc  840
cgcacatcat catcaccatc acggggccgc agaacaaaaa ctcatctcag aagaggatct  900
gaatggggcc gc                                                       912
```

```
SEQ ID NO: 2               moltype = AA   length = 287
FEATURE                    Location/Qualifiers
VARIANT                    4
                           note = Any amino acid
VARIANT                    7..8
                           note = Any amino acid
source                     1..287
                           mol_type = protein
                           organism = synthetic construct
SEQUENCE: 2
MKYXLPXXAA GLLLLAAQPA MAEVQLLESG GGLVQPGGSL RLSCAASGFT FSSYAMSWVR  60
QAPGKGLEWV SSISSNGDDT AYADSVKGRF TISRDNSKDT LYLQMNSLRA EDTAVYYCAK  120
ANNSFDYWGQ GTLVTVSSGG GGSGGGGSGG GGSTDIQMTQ SPSSLSASVG DRVTITCRAS  180
QSISSYLNWY QQKPGKAPKL LIYNASTLQS GVPSRFSGSG SGTDFTLTIS SLQPEDFATY  240
YCQQDSATPY TFGQGTKVEI KRAAAHHHHH HGAAEQKLIS EEDLNGA              287
```

```
SEQ ID NO: 3               moltype = DNA   length = 927
FEATURE                    Location/Qualifiers
variation                  6
                           note = a, c, t, g, unknown or other
variation                  25..26
                           note = a, c, t, g, unknown or other
variation                  34..35
                           note = a, c, t, g, unknown or other
variation                  37
                           note = a, c, t, g, unknown or other
variation                  76
                           note = a, c, t, g, unknown or other
variation                  81
                           note = a, c, t, g, unknown or other
variation                  90..91
                           note = a, c, t, g, unknown or other
variation                  112
                           note = a, c, t, g, unknown or other
variation                  141
                           note = a, c, t, g, unknown or other
variation                  220
                           note = a, c, t, g, unknown or other
source                     1..927
                           mol_type = other DNA
                           organism = synthetic construct
SEQUENCE: 3
tatganccat gattacgcca agctnncatg caanntntat tttcaaggag acagtcataa  60
tgaaatacct attgcntacg ncagccgctn ngattgttat tactcgcggc cncagccggc  120
catggccgag gtgcagctgt nggagtctgg gggaggcttg gtacagcctg gggggtccct  180
gagactctcc tgtgcagcct ctggattcac ctttagcagn tatgccatga gctgggtccg  240
ccaggctcca gggaaggggc tggagtgggt ctcatagatt tagcagtcgg gtccggttac  300
atcttacgca gactccgtga agggccggtt caccatctcc agagacaatt ccaagaacac  360
gctgtatctg caaatgaaca gcctgagagc cgaggacacg gccgtatatt actgtgcgaa  420
acgtcagttg atgtttgact actggggcca gggaaccctg gtcaccgtct cgagcggtgg  480
aggcggttca ggcggaggtg gcagcggcgg tggcgggtcg acggacatcc agatgaccca  540
gtctccatcc tccctgtctg catctgtagg agacagagtc accatcactt gccgggcaag  600
tcagagcatt agcagctatt aaattggta tcagcagaaa ccaggaaag ccctaagct  660
cctgatctat gctgcatcca gtttgcaaag tggggtccca tcaaggttca gtggcagtgg  720
atctgggaca gatttcactc tcaccatcag cagtctgcaa cctgaagatt ttgcaactta  780
ctactgtcaa cagagttaca gtaccctaa tacgttcggc caagggacca aggtggaaat  840
caaacgggcg gccgcacatc atcatcacca tcacggggcc gcagaacaaa aactcatctc  900
agaagaggat ctgaatgggc cgcatag                                      927
```

```
SEQ ID NO: 4               moltype = AA   length = 266
FEATURE                    Location/Qualifiers
VARIANT                    7
                           note = Any amino acid
VARIANT                    33
                           note = Any amino acid
source                     1..266
                           mol_type = protein
                           organism = synthetic construct
SEQUENCE: 4
```

```
MAEVQLXESG GGLVQPGGSL RLSCAASGFT FSXYAMSWVR QAPGKGLEWV SIQSGPVTSY    60
ADSVKGRFTI SRDNSKNTLY LQMNSLRAED TAVYYCAKRQ LMFDYWGQGT LVTVSSGGGG   120
SGGGGSGGGG STDIQMTQSP SSLSASVGDR VTITCRASQS ISSYLNWYQQ KPGKAPKLLI   180
YAASSLQSGV PSRFSGSGSG TDFTLTISSL QPEDFATYYC QQSYSTPNTF GQGTKVEIKR   240
AAAHHHHHHG AAEQKLISEE DLNGPH                                       266
```

```
SEQ ID NO: 5            moltype = DNA   length = 833
FEATURE                 Location/Qualifiers
variation               4
                        note = a, c, t, g, unknown or other
variation               14..15
                        note = a, c, t, g, unknown or other
variation               28
                        note = a, c, t, g, unknown or other
variation               34
                        note = a, c, t, g, unknown or other
variation               37
                        note = a, c, t, g, unknown or other
variation               67
                        note = a, c, t, g, unknown or other
variation               71..77
                        note = a, c, t, g, unknown or other
variation               101..102
                        note = a, c, t, g, unknown or other
variation               177
                        note = a, c, t, g, unknown or other
variation               189
                        note = a, c, t, g, unknown or other
variation               221..222
                        note = a, c, t, g, unknown or other
variation               253..258
                        note = a, c, t, g, unknown or other
variation               261
                        note = a, c, t, g, unknown or other
variation               745
                        note = a, c, t, g, unknown or other
variation               771
                        note = a, c, t, g, unknown or other
variation               794
                        note = a, c, t, g, unknown or other
variation               800
                        note = a, c, t, g, unknown or other
variation               810
                        note = a, c, t, g, unknown or other
variation               814..816
                        note = a, c, t, g, unknown or other
source                  1..833
                        mol_type = other DNA
                        organism = synthetic construct
SEQUENCE: 5
attncgccaa gctnncatgc aaaatttnta tttnaangga gacagtcata atgaaatacc    60
tattgcntac nnnnnnncgc tggattgtta ttactcgcgg nncagccggc catggccgag   120
gtgcagctgt tggagtctgg gggaggcttg gtacagcctg gggggtccct gagactntcc   180
tgtgcagcnt ctggattcac ctttagcagc tatgccatga nntgggtccg ccaggctcca   240
gggaaggggc tgnnnnnngt ntcatctatt acgtagacgg gttcgtagac acagtacgca   300
gactccgtga agggcaggtt caccatctcc agagacaatt ccaagaacac gctgtatctg   360
caaatgaaca gcctgagagc cgaggacacg gccgtatatt actgtgcgaa acagcatgat   420
gattttgact actggggcca gggaaccctg gtcaccgtct cgagcggtgg aggcggttca   480
ggcggaggtg gcagcggcgg tggcgggtcg acggacatcc agatgaccca gtctccatcc   540
tccctgtctg catctgtagg agacagagtc accatcactt gccgggcaag tcagagcatt   600
agcagctatt taaattggta tcagcagaaa ccagggaaag cccctaagct cctgatctat   660
actgcatcca atttgcaaag tggggtccca tcaaggttca gtggcagtgg atctgggaca   720
gatttcactc tcaccatcag cagtntgcaa cctgaagatt ttgcaactta ntactgtcaa   780
cagctggatg tgtntccttn gacgttcggn caannnacca aggtggaaat caa           833
```

```
SEQ ID NO: 6            moltype = AA   length = 238
FEATURE                 Location/Qualifiers
VARIANT                 22
                        note = Any amino acid
VARIANT                 26
                        note = Any amino acid
VARIANT                 37
                        note = Any amino acid
VARIANT                 48..50
                        note = Any amino acid
VARIANT                 210
                        note = Any amino acid
VARIANT                 218
                        note = Any amino acid
```

```
VARIANT              226
                     note = Any amino acid
VARIANT              228
                     note = Any amino acid
VARIANT              231
                     note = Any amino acid
VARIANT              233
                     note = Any amino acid
source               1..238
                     mol_type = protein
                     organism = synthetic construct
SEQUENCE: 6
MAEVQLLESG GGLVQPGGSL RXSCAXSGFT FSSYAMXWVR QAPGKGLXXX SSITTGSTQY  60
ADSVKGRFTI SRDNSKNTLY LQMNSLRAED TAVYYCAKQH DDFDYWGQGT LVTVSSGGGG  120
SGGGGSGGGG STDIQMTQSP SSLSASVGDR VTITCRASQS ISSYLNWYQQ KPGKAPKLLI  180
YTASNLQSGV PSRFSGSGSG TDFTLTISSX QPEDFATXYC QQLDVXPXTF XQXTKVEI    238

SEQ ID NO: 7         moltype = DNA  length = 963
FEATURE              Location/Qualifiers
variation            29
                     note = a, c, t, g, unknown or other
variation            660
                     note = a, c, t, g, unknown or other
variation            690
                     note = a, c, t, g, unknown or other
variation            763
                     note = a, c, t, g, unknown or other
variation            853
                     note = a, c, t, g, unknown or other
variation            861..862
                     note = a, c, t, g, unknown or other
variation            872..874
                     note = a, c, t, g, unknown or other
variation            876..877
                     note = a, c, t, g, unknown or other
variation            898
                     note = a, c, t, g, unknown or other
variation            912
                     note = a, c, t, g, unknown or other
variation            914..916
                     note = a, c, t, g, unknown or other
variation            954
                     note = a, c, t, g, unknown or other
variation            957..958
                     note = a, c, t, g, unknown or other
source               1..963
                     mol_type = other DNA
                     organism = synthetic construct
SEQUENCE: 7
gagacagtca tagctagcat gaaaaagant tggctggcgc tggctggttt agttttagcg  60
tttagcgcat cggcggacta caaagaggcc cagccggcca tggacctggg taagaaactg  120
ctggaagctg ctcgtgctgg tcaggacgac gaagttcgta tcctgatggc taacggtgct  180
gacgttaacg ctgacgacta cgaaggttgg actccgctgc acctggctgc tatggttggt  240
cacctggaaa tcgttgaagt tctgctgaag tacggtgctg acgttaacgc tcaggacaaa  300
ttcggtaaga ccgctttcga catctccatc gacaacggta acgaggacct ggctgaaatc  360
ctgcaagcgg ccgcacatca tcatcaccat cacggggccg cagaacaaaa actcatctca  420
gaagaggatc tgaatggggc cgcatagact gttgaaagtt gtttagcaaa acctcataca  480
gaaaattcat ttactaacgt ctggaaagac gacaaaactt tagatcgtta cgctaactat  540
gagggctgtc tgtggaatgc tacaggcgtt gtggtttgta ctggtgacga aactcagtgt  600
tacggtacat gggttcctat tgggcttgct atccctgaaa atgagggtgg tggctctgan  660
ggtggcggtt ctgagggtgg cggttctgan ggtggcggta ctaaacctcc tgagtacggt  720
gatacaccta ttccgggcta tacttatatc aaccctctcg acngcactta tccgcctggt  780
actgagcaaa accccgctaa tcctaatccc ttctcttgag gagtctcagc ctcttaatac  840
tttcatgttt canaataata nnttccgaaa tnnncnnggt gcattaactg tttatacngg  900
cactgttact cnannnactg accccgtttt aaaacttatt accagtacac tccntgnnat  960
cat                                                                963

SEQ ID NO: 8         moltype = AA  length = 142
FEATURE              Location/Qualifiers
VARIANT              4
                     note = Any amino acid
source               1..142
                     mol_type = protein
                     organism = synthetic construct
SEQUENCE: 8
MKKXWLALAG LVLAFSASAD YKEAQPAMDL GKKLLEAARA GQDDEVRILM ANGADVNADD  60
YEGWTPLHLA AMVGHLEIVE VLLKYGADVN AQDKFGKTAF DISIDNGNED LAEILQAAAH  120
HHHHHGAAEQ KLISEEDLNG AA                                          142
```

```
SEQ ID NO: 9           moltype = DNA   length = 890
FEATURE                Location/Qualifiers
variation              10
                       note = a, c, t, g, unknown or other
variation              15
                       note = a, c, t, g, unknown or other
variation              67
                       note = a, c, t, g, unknown or other
variation              778
                       note = a, c, t, g, unknown or other
variation              799
                       note = a, c, t, g, unknown or other
variation              814
                       note = a, c, t, g, unknown or other
variation              822..823
                       note = a, c, t, g, unknown or other
variation              843..844
                       note = a, c, t, g, unknown or other
variation              866..867
                       note = a, c, t, g, unknown or other
source                 1..890
                       mol_type = other DNA
                       organism = synthetic construct
SEQUENCE: 9
ttcaggagan agtcntaatg aaatacctat tgcctacggc agccgctgga ttgttattac  60
tcgcggncca gccggccatg gccgaggtgc agctgttgga gtctggggga ggcttggtac  120
agcctggggg gtccctgaga ctctcctgtg cagcctctgg attcaccttt agcagctatg  180
ccatgagctg ggtccgccag gctccaggga aggggctgga gtgggtctca ggtatttcta  240
ataatggtag taatacaact tacgcagact ccgtgaaggg ccggttcacc atctccagag  300
acaattccaa gaacacgctg tatctgcaaa tgaacagcct gagagccgac gacacggccg  360
tatattactg tgcgaaagct tcttatactt ttgactactg gggccaggga accctggtca  420
ccgtctcgag cggtggaggc ggttcaggcg gaggtggcag cggcggtggc gggtcgacgg  480
acatccagat gacccagtct ccatcctccc tgtctgcatc tgtaggagac agagtcacca  540
tcacttgccg ggcaagtcag agcattagca gctatttaaa ttggtatcag cagaaaccag  600
ggaaagcccc taagctcctg atctatagtg catcctcttt gcaaagtggg gtcccatcaa  660
ggttcagtgg cagtggatct gggacagatt tcactctcac catcagcagt ctgcaacctg  720
aagattttgc aacttactac tgtcaacagt attctggttc tcctgctacg ttcggccnag  780
ggaccaaggt ggaaatcana cgggcggccg cacntcatca tnnccatcac ggggccgcag  840
aannaaaact catctcagaa gagganntga atggggccgc atagactgtt  890

SEQ ID NO: 10          moltype = AA   length = 283
FEATURE                Location/Qualifiers
VARIANT                17
                       note = Any amino acid
VARIANT                254
                       note = Any amino acid
VARIANT                261
                       note = Any amino acid
VARIANT                266
                       note = Any amino acid
VARIANT                269
                       note = Any amino acid
VARIANT                276
                       note = Any amino acid
VARIANT                283
                       note = Any amino acid
source                 1..283
                       mol_type = protein
                       organism = synthetic construct
SEQUENCE: 10
MKYLLPTAAA GLLLLAXQPA MAEVQLLESG GGLVQPGGSL RLSCAASGFT FSSYAMSWVR  60
QAPGKGLEWV SGISNNGSNT TYADSVKGRF TISRDNSKNT LYLQMNSLRA EDTAVYYCAK  120
ASYTFDYWGQ GTLVTVSSGG GGSGGGGSGG GGSTDIQMTQ SPSSLSASVG DRVTITCRAS  180
QSISSYLNWY QQKPGKAPKL LIYSASSLQS GVPSRFSGSG SGTDFTLTIS SLQPEDFATY  240
YCQQYSGSPA TFGXGTKVEI XRAAAXHHXH HGAAEXKLIS EEX  283

SEQ ID NO: 11          moltype = DNA   length = 883
FEATURE                Location/Qualifiers
variation              8
                       note = a, c, t, g, unknown or other
variation              10
                       note = a, c, t, g, unknown or other
variation              23
                       note = a, c, t, g, unknown or other
variation              51
                       note = a, c, t, g, unknown or other
variation              53..54
                       note = a, c, t, g, unknown or other
variation              86
```

-continued

```
                    note = a, c, t, g, unknown or other
variation           154
                    note = a, c, t, g, unknown or other
variation           172
                    note = a, c, t, g, unknown or other
variation           267
                    note = a, c, t, g, unknown or other
variation           434
                    note = a, c, t, g, unknown or other
variation           447
                    note = a, c, t, g, unknown or other
variation           529
                    note = a, c, t, g, unknown or other
variation           546
                    note = a, c, t, g, unknown or other
variation           555..556
                    note = a, c, t, g, unknown or other
variation           581
                    note = a, c, t, g, unknown or other
variation           584
                    note = a, c, t, g, unknown or other
variation           620
                    note = a, c, t, g, unknown or other
variation           639
                    note = a, c, t, g, unknown or other
variation           645
                    note = a, c, t, g, unknown or other
variation           672
                    note = a, c, t, g, unknown or other
variation           700
                    note = a, c, t, g, unknown or other
variation           734
                    note = a, c, t, g, unknown or other
variation           754..755
                    note = a, c, t, g, unknown or other
variation           764
                    note = a, c, t, g, unknown or other
variation           766
                    note = a, c, t, g, unknown or other
variation           785
                    note = a, c, t, g, unknown or other
variation           787..788
                    note = a, c, t, g, unknown or other
variation           797
                    note = a, c, t, g, unknown or other
variation           799
                    note = a, c, t, g, unknown or other
variation           802
                    note = a, c, t, g, unknown or other
variation           815
                    note = a, c, t, g, unknown or other
variation           817
                    note = a, c, t, g, unknown or other
variation           819..823
                    note = a, c, t, g, unknown or other
variation           826
                    note = a, c, t, g, unknown or other
variation           828..830
                    note = a, c, t, g, unknown or other
variation           837
                    note = a, c, t, g, unknown or other
variation           839
                    note = a, c, t, g, unknown or other
variation           854..855
                    note = a, c, t, g, unknown or other
variation           860
                    note = a, c, t, g, unknown or other
variation           868
                    note = a, c, t, g, unknown or other
variation           872..874
                    note = a, c, t, g, unknown or other
variation           876
                    note = a, c, t, g, unknown or other
variation           880
                    note = a, c, t, g, unknown or other
source              1..883
                    mol_type = other DNA
                    organism = synthetic construct
SEQUENCE: 11
```

-continued

```
ttcagganan agtcataatg aantacctat tgcctacggc agccgctgga ntnntattac  60
tcgcggccca gccggccatg gcccangtgc agctggtgga gtctggggga ggcgtggtcc  120
agcctgggag gtccctgaga ctctcctgtg cagnctccgg attcacctttt ancagctatg  180
acatgggctg ggtccgccag gctccaggga aggggctgga gtgggtctca agtattagtg  240
gtagtggtcc taccatgaac tacgcanact ctgtgaaggg ccgattcacc gtctccagag  300
acaattccaa gaacacgctg tatctgcaaa tggacagcct gagagccgag gacacggccg  360
tatattactg tgcgaaaggg ggtacggact ttgactactg gggccagggc accctggtca  420
ccgtctcctc aggnggaggc ggttcangcg gaggtggctc tggcggtggc ggatcgtctg  480
agctgactca ggaccctgct gtgtctgtgg ccttgggaca gacagtcanc atcacatgcc  540
aagganacag cctcnnaacc tattatgcaa gctggtacca ncanaagcca ggacaggccc  600
ctgtacttgt catctatggn aaaaacaacc ggccctcang gatcncagac cgattctctg  660
gctccagctc angaaacaca gcttccttga ccatcactgn ggctcaggcg gaagatgagg  720
ctgactatta ctgnaactcc cgggacagca gtgnnaacca tctnangagt gttcggcgga  780
gggancnngc tgaccgncnt angtgcggcc gcagnancnn nnnctncnnn tcagaanang  840
atctgaatgg ggcnncatan actgttgnaa annngnttan caa            883
```

```
SEQ ID NO: 12          moltype = AA  length = 255
FEATURE                Location/Qualifiers
VARIANT                2
                       note = Any amino acid
VARIANT                12..13
                       note = Any amino acid
VARIANT                23
                       note = Any amino acid
VARIANT                46
                       note = Any amino acid
VARIANT                52
                       note = Any amino acid
VARIANT                84
                       note = Any amino acid
VARIANT                139
                       note = Any amino acid
VARIANT                144
                       note = Any amino acid
VARIANT                171
                       note = Any amino acid
VARIANT                177
                       note = Any amino acid
VARIANT                180
                       note = Any amino acid
VARIANT                188..189
                       note = Any amino acid
VARIANT                201
                       note = Any amino acid
VARIANT                208
                       note = Any amino acid
VARIANT                210
                       note = Any amino acid
VARIANT                219
                       note = Any amino acid
VARIANT                228
                       note = Any amino acid
VARIANT                239
                       note = Any amino acid
VARIANT                246
                       note = Any amino acid
VARIANT                249..250
                       note = Any amino acid
source                 1..255
                       mol_type = protein
                       organism = synthetic construct
SEQUENCE: 12
MXYLLPTAAA GXXLLAAQPA MAXVQLVESG GGVVQPGRSL RLSCAXSGFT FXSYDMGWVR  60
QAPGKGLEWV SSISGSGPTM NYAXSVKGRF TVSRDNSKNT LYLQMDSLRA EDTAVYYCAK  120
GGTDFDYWGQ GTLVTVSSXG GGSXGGGSGG GGSSELTQDP AVSVALGQTV XITCQGXSLX  180
TYYASWYXXK PGQAPVLVIY XKNNRPSXIX DRFSGSSSXN TASLTITXAQ AEDEADYYXN  240
SRDSSXNHXX SVRRR                                             255
```

```
SEQ ID NO: 13          moltype = DNA  length = 854
FEATURE                Location/Qualifiers
variation              10
                       note = a, c, t, g, unknown or other
variation              15
                       note = a, c, t, g, unknown or other
variation              651
                       note = a, c, t, g, unknown or other
variation              751..752
                       note = a, c, t, g, unknown or other
variation              760
```

```
                          note = a, c, t, g, unknown or other
variation                 766..767
                          note = a, c, t, g, unknown or other
variation                 776
                          note = a, c, t, g, unknown or other
variation                 778
                          note = a, c, t, g, unknown or other
variation                 780
                          note = a, c, t, g, unknown or other
variation                 787..789
                          note = a, c, t, g, unknown or other
variation                 791..794
                          note = a, c, t, g, unknown or other
variation                 801..802
                          note = a, c, t, g, unknown or other
variation                 816..817
                          note = a, c, t, g, unknown or other
variation                 821
                          note = a, c, t, g, unknown or other
variation                 824..828
                          note = a, c, t, g, unknown or other
variation                 831
                          note = a, c, t, g, unknown or other
variation                 833
                          note = a, c, t, g, unknown or other
variation                 836..839
                          note = a, c, t, g, unknown or other
source                    1..854
                          mol_type = other DNA
                          organism = synthetic construct
SEQUENCE: 13
ttcaggagan agtcntaatg aaatacctat tgcctacggc agccgctgga ttgttattac   60
tcgcggccca gccggccatg gccgaggtgc agctgttgga gtctggggga ggcttggtac  120
agcctggggg gtccctgaga ctctcctgtg cagcctctgg attcaccttt agcagctatg  180
ccatgagctg ggtccgccag gctccaggga aggggctgga gtgggtctca gctattacta  240
atgatggtgc tggtacaact tacgcagact ccgtgaaggg ccggttcacc atctccagag  300
acaattccaa gaacacgctg tatctgcaaa tgaacagcct gagagccgag gacacggccg  360
tatattactg tgcgaaatct tatactggtt ttgactactg gggccaggga accctggtca  420
ccgtctcgag cggtggaggc ggttcaggcg gaggtggcag cggcggtggc gggtcgacgg  480
acatccagat gacccaatct ccatcctccc tgtctgcatc tgtaggagac agagtcacca  540
tcacttgccg ggcaagtcag agcattagca gctatttaaa ttggtatcag cagaaaccag  600
ggaaagcccc taagctcctg atctatactg catccacttt gcaaagtggg ntcccattaa  660
ggttcagtgg cagtggatct gggacagatt tcactctcac catcagcagt ctgcaacctg  720
aagattttgc aacttactac tgtcaacaga nntatgctan tcctannacg ttcggncnan  780
gggaccnnng nnnnaaatca nncgggcggc cgcacnncat natnnnnnat ncncgnnnnc  840
gcagaacaaa actc                                                    854

SEQ ID NO: 14            moltype = AA  length = 252
FEATURE                  Location/Qualifiers
VARIANT                  212
                         note = Any amino acid
VARIANT                  245
                         note = Any amino acid
VARIANT                  248
                         note = Any amino acid
VARIANT                  250
                         note = Any amino acid
source                   1..252
                         mol_type = protein
                         organism = synthetic construct
SEQUENCE: 14
MKYLLPTAAA GLLLLAAQPA MAEVQLLESG GGLVQPGGSL RLSCAASGFT FSSYAMSWVR   60
QAPGKGLEWV SAITNDGAGT TYADSVKGRF TISRDNSKNT LYLQMNSLRA EDTAVYYCAK  120
SYTGFDYWGQ GTLVTVSSGG GGSGGGGSGG GGSTDIQMTQ SPSSLSASVG DRVTITCRAS  180
QSISSYLNWY QQKPGKAPKL LIYTASTLQS GXPLRFSGSG SGTDFTLTIS SLQPEDFATY  240
YCQQXYAXPX TF                                                       252

SEQ ID NO: 15            moltype = DNA  length = 972
FEATURE                  Location/Qualifiers
variation                4
                         note = a, c, t, g, unknown or other
variation                8
                         note = a, c, t, g, unknown or other
variation                11..12
                         note = a, c, t, g, unknown or other
variation                15
                         note = a, c, t, g, unknown or other
variation                32
                         note = a, c, t, g, unknown or other
```

```
variation              749
                       note = a, c, t, g, unknown or other
variation              850
                       note = a, c, t, g, unknown or other
variation              857
                       note = a, c, t, g, unknown or other
variation              908..909
                       note = a, c, t, g, unknown or other
variation              912..913
                       note = a, c, t, g, unknown or other
variation              918
                       note = a, c, t, g, unknown or other
variation              930
                       note = a, c, t, g, unknown or other
variation              942
                       note = a, c, t, g, unknown or other
variation              944
                       note = a, c, t, g, unknown or other
variation              948
                       note = a, c, t, g, unknown or other
variation              950..951
                       note = a, c, t, g, unknown or other
variation              954
                       note = a, c, t, g, unknown or other
variation              962
                       note = a, c, t, g, unknown or other
variation              968
                       note = a, c, t, g, unknown or other
source                 1..972
                       mol_type = other DNA
                       organism = synthetic construct
SEQUENCE: 15
ctangcgncc nnttnagatc ctcttctgag angagttttt gttctgcggc cccgtgatgg  60
tgatgatgat gtgcggccgc ccgtttgatt tccaccttgg tcccttggcc gaacgtcgca  120
ggagtctgat gagtctgttg acagtagtaa gttgcaaaat cttcaggttg cagactgctg  180
atggtgagag tgaaatctgt cccagatcca ctgccactga accttgatgg gaccccactt  240
tgcaactggg atgccggata gatcaggagc ttaggggctt tccctggttt ctgctgatac  300
caatttaaat agctgctaat gctctgactt gcccggcaag tgatggtgac tctgtctcct  360
acagatgcag acagggagga tggagactgg gtcatctgga tgtccgtcga cccgccaccg  420
ccgctgccac ctccgcctga accgcctcca ccgctcgaga cggtgaccag ggttccctgg  480
ccccagtagt caaaagacca aaactgtttc gcacagtaat atacggccgt gtcctcggct  540
ctcaggctgt tcatttgcag atacagcgtg ttcttggaat tgtctctgga gatggtgaac  600
cggcccttca cggagtctgc gtacgttgtc ggcggaccct gcttcgcaat atctgagacc  660
cactccagcc ccttccctgg agcctggcgg acccagctca tggcatagct gctaaaggtg  720
aatccagagg ctgcacagga gagtctcang gaccccccag gctgtaccaa gcctccccca  780
gactccaaca gctgcacctc ggccatggcc ggctgggccg cgagtaataa caatccagcg  840
gctgccgtan gcaatangta tttcattatg actgtctcct tgaaatagaa tttgcatgca  900
agcttggnnt annatggnca tagctgtttn ctgtgtgaaa tngntatncn ntcncaattc  960
cncacaanat ac                                                     972

SEQ ID NO: 16            moltype = AA  length = 283
FEATURE                  Location/Qualifiers
VARIANT                  4
                         note = Any amino acid
VARIANT                  6
                         note = Any amino acid
VARIANT                  40
                         note = Any amino acid
VARIANT                  279
                         note = Any amino acid
source                   1..283
                         mol_type = protein
                         organism = synthetic construct
SEQUENCE: 16
MKYXLXTAAA GLLLLAAQPA MAEVQLLESG GGLVQPGGSX RLSCAASGFT FSSYAMSWVR  60
QAPGKGLEWV SDIAKQGPPT TYADSVKGRF TISRDNSKNT LYLQMNSLRA EDTAVYYCAK  120
QFWSFDYWGQ GTLVTVSSGG GGSGGGGSGG GGSTDIQMTQ SPSSLSASVG DRVTITCRAS  180
QSISSYLNWY QQKPGKAPKL LIYPASQLQS GVPSRFSGSG SGTDFTLTIS SLQPEDFATY  240
YCQQTHQTPA TFGQGTKVEI KRAAAHHHHH HGAAEQKLXS EED                    283

SEQ ID NO: 17            moltype = DNA  length = 980
FEATURE                  Location/Qualifiers
variation                6
                         note = a, c, t, g, unknown or other
variation                22
                         note = a, c, t, g, unknown or other
variation                739
                         note = a, c, t, g, unknown or other
variation                840
```

-continued

```
                              note = a, c, t, g, unknown or other
variation                     880
                              note = a, c, t, g, unknown or other
variation                     903
                              note = a, c, t, g, unknown or other
variation                     910
                              note = a, c, t, g, unknown or other
variation                     942
                              note = a, c, t, g, unknown or other
variation                     950
                              note = a, c, t, g, unknown or other
variation                     955
                              note = a, c, t, g, unknown or other
variation                     957
                              note = a, c, t, g, unknown or other
variation                     961
                              note = a, c, t, g, unknown or other
variation                     970
                              note = a, c, t, g, unknown or other
variation                     978
                              note = a, c, t, g, unknown or other
source                        1..980
                              mol_type = other DNA
                              organism = synthetic construct
SEQUENCE: 17
cattcngatc ctcttctgag angagttttt gttctgcggc cccgtgatgg tgatgatgat    60
gtgcggccgc ccgtttgatt tccaccttgg tcccttggcc gaacgtaata ggagacggat   120
gcgactgttg acagtagtaa gttgcaaaat cttcaggttg cagactgctg atggtgagag   180
tgaaatctgt cccagatcca ctgccactga accttgatgg gacccctt  tgcaaattgg    240
atgccctata gatcaggagc ttaggggctt tccctggttt ctgctgatac caatttaaat   300
agctgctaat gctctgactt gcccggcaag tgatggtgac tctgtctcct acagatgcag   360
acagggagga tggagactgg gtcatctgga tgtccgtcga cccgccaccg ccgctgccac   420
ctccgcctga accgcctcca ccgctcgaga cggtgaccag ggttccctgg ccccagtagt   480
caaacgccgt ccaacgtttc gcacagtaat atacggccgt gtcctcggct ctcaggctgt   540
tcatttgcag atacagcgtg ttcttggaat tgtctctgga gatggtgaac cggcccttca   600
cggagtctgc gtaaattgtc ggactaccac ccccagcaat cgatgagacc cactccagcc   660
ccttccctgg agcctggcgg acccagctca tggcatagct gctaaaggtg aatccagagg   720
ctgcacagga gagtctcang gaccccccag gctgtaccaa gcctcccca  gactccaaca   780
gctgcacctc ggccatggcc ggctgggccg cgagtaataa caatccagcg gctgccgtan   840
gcaataggta tttcattatg actgtctcct tgaaatagan tttgcatgca agcttggcgt   900
aantcatggn catagctgtt tcctgtgtga aattgttatc cnctcacaan ttccncncaa   960
ncatacgaan cccggaangc                                              980
```

```
SEQ ID NO: 18                 moltype = AA   length = 302
FEATURE                       Location/Qualifiers
VARIANT                       2
                              note = Any amino acid
VARIANT                       4
                              note = Any amino acid
VARIANT                       12
                              note = Any amino acid
VARIANT                       25
                              note = Any amino acid
VARIANT                       59
                              note = Any amino acid
VARIANT                       298
                              note = Any amino acid
source                        1..302
                              mol_type = protein
                              organism = synthetic construct
SEQUENCE: 18
MXMXYAKLAC KXYFKETVIM KYLLXTAAAG LLLLAAQPAM AEVQLLESGG GLVQPGGSXR    60
LSCAASGFTF SSYAMSWVRQ APGKGLEWVS SIAGGGSPTI YADSVKGRFT ISRDNSKNTL   120
YLQMNSLRAE DTAVYYCAKR WTAFDYWGQG TLVTVSSGGG GSGGGGSGGG GSTDIQMTQS   180
PSSLSASVGD RVTITCRASQ SISSYLNWYQ QKPGKAPKLL IYRASNLQSG VPSRFSGSGS   240
GTDFTLTISS LQPEDFATYY CQQSHPSPIT FGQGTKVEIK RAAAHHHHHH GAAEQKLXSE   300
ED                                                                 302
```

```
SEQ ID NO: 19                 moltype = DNA   length = 980
FEATURE                       Location/Qualifiers
variation                     8..11
                              note = a, c, t, g, unknown or other
variation                     850
                              note = a, c, t, g, unknown or other
variation                     912
                              note = a, c, t, g, unknown or other
variation                     937
                              note = a, c, t, g, unknown or other
variation                     957..958
```

-continued

```
                                note = a, c, t, g, unknown or other
variation                       965
                                note = a, c, t, g, unknown or other
variation                       976
                                note = a, c, t, g, unknown or other
source                          1..980
                                mol_type = other DNA
                                organism = synthetic construct
SEQUENCE: 19
ctatgcgnnn nattcagatc ctcttctgag atgagttttt gttctgcggc cccgtgatgg   60
tgatgatgat gtgcggccgc ccgtttgatt tccaccttgg tcccttggcc gaacgtagga  120
ggcgaagtct gaacctgttg acagtagtaa gttgcaaaat cttcaggttg cagactgctg  180
atggtgagag tgaaatctgt cccagatcca ctgccactga accttgatgg gaccccactt  240
tgcaacaggg atgcacgata gatcaggagc ttaggggctt tccctggttt ctgctgatac  300
caatttaaat agctgctaat gctctggctt gcccggcaag tgatggtgac tctgtctcct  360
acagatgcag acagggagga tggagactgg gtcatctgga tgtccgtcga cccgccaccg  420
ccgctgccac ctccgcctga accgcctcca ccgctcgaga cggtgaccag ggttccctgg  480
ccccagtagt caaactgctt accacgtttc gcacagtaat atacggccgt gtcctcggct  540
ctcaggctgt tcatttgcag atacagcgtg ttcttggaat tgtctctgga gatggtgaac  600
cggcccttca cggagtctgc gtaatgtgtc acagtaccat ccggccaaat acctgagacc  660
cactccagcc ccttccctgg agcctggcgg acccagctca tggcatagct gctaaaggtg  720
aatccagagg ctgcacagga gagtctcagg gacccccag gctgtaccaa gcctccccca  780
gactccaaca gctgcacctc ggccatggcc ggctgggccg cgagtaataa caatccagcg  840
gctgccgtan gcaataggta tttcattatg actgtctcct tgaaatagaa tttgcatgca  900
agcttggcgt antcatggtc atagctgttt cctgtgngaa attgttatcc gctcacnntt  960
ccacncaaca tacganccgg                                              980

SEQ ID NO: 20                   moltype = AA  length = 289
FEATURE                         Location/Qualifiers
VARIANT                         6
                                note = Any amino acid
VARIANT                         286..287
                                note = Any amino acid
source                          1..289
                                mol_type = protein
                                organism = synthetic construct
SEQUENCE: 20
MKYLLXTAAA GLLLLAAQPA MAEVQLLESG GGLVQPGGSL RLSCAASGFT FSSYAMSWVR   60
QAPGKGLEWV SGIWPDGTVT HYADSVKGRF TISRDNSKNT LYLQMNSLRA EDTAVYYCAK  120
RGKQFDYWGQ GTLVTVSSGG GGSGGGGSGG GGSTDIQMTQ SPSSLSASVG DRVTITCRAS  180
QSISSYLNWY QQKPGKAPKL LIYRASLLQS GVPSRFSGSG SGTDFTLTIS SLQPEDFATY  240
YCQQVQTSPP TFGQGTKVEI KRAAAHHHHH HGAAEQKLIS EEDLNXXHR              289

SEQ ID NO: 21                   moltype = DNA  length = 973
FEATURE                         Location/Qualifiers
variation                       4
                                note = a, c, t, g, unknown or other
variation                       8..13
                                note = a, c, t, g, unknown or other
variation                       849..851
                                note = a, c, t, g, unknown or other
variation                       856
                                note = a, c, t, g, unknown or other
variation                       904
                                note = a, c, t, g, unknown or other
variation                       907..908
                                note = a, c, t, g, unknown or other
source                          1..973
                                mol_type = other DNA
                                organism = synthetic construct
SEQUENCE: 21
ctangcgnnn nnntcagatc ctcttctgag atgagttttt gttctgcggc cccgtgatgg   60
tgatgatgat gtgcggccgc ccgtttgatt tccaccttgg tcccttggcc gaacgtagaa  120
ggattatcat cattctgttg acagtagtaa gttgcaaaat cttcaggttg cagactgctg  180
atggtgagag tgaaatctgt cccagatcca ctgccactga accttgatgg gaccccactt  240
tgcaaagtgg atgcatcata aatcaggagc ttaggggctt tccctggttt ctgctgatac  300
caatttaaat agctgctaat gctctgactt gcccggcaag tgatggtgac tctgtctcct  360
acagatgcag acagggagga tggagactgg gtcatctgga tgtccgtcga cccgccaccg  420
ccgctgccac ctccgcctga accgcctcca ccgctcgaga cggtgaccag ggttccctgg  480
ccccagtagt caaaaccatt agaagttttc gcacagtaat atacggccgt gtcctcggct  540
ctcaggctgt tcatttgcag atacagcgtg ttcttggaat tgtctctgga gatggtgaac  600
cggcccttca cggagtctgc gtaatatgta gtactaccag tagcatcaat agttgagacc  660
cactccagcc ccttccctgg agcctggcgg acccagctca tggcatagct gctaaaggtg  720
aatccagagg ctgcacagga gagtctcagg gacccccag gctgtaccaa gcctccccca  780
gactccaaca gctgcacctc ggccatggcc ggctgggccg cgagtaataa caatccagcg  840
gctgccgtnn naatangtat ttcattatga ctgtctcctt gaaatagaat ttgcatgcaa  900
gctnggnnta atcatggtca tagctgtttc ctgtgtgaaa ttgttatccg ctcacaattc  960
cacacaacat acg                                                     973
```

-continued

```
SEQ ID NO: 22            moltype = AA   length = 294
FEATURE                  Location/Qualifiers
VARIANT                  14
                         note = Any amino acid
VARIANT                  16
                         note = Any amino acid
source                   1..294
                         mol_type = protein
                         organism = synthetic construct
SEQUENCE: 22
MQILFQGDSH NEIXIXTAAA GLLLLAAQPA MAEVQLLESG GGLVQPGGSL RLSCAASGFT   60
FSSYAMSWVR QAPGKGLEWV STIDATGSTT YYADSVKGRF TISRDNSKNT LYLQMNSLRA   120
EDTAVYYCAK TSNGFDYWGQ GTLVTVSSGG GGSGGGGSGG GGSTDIQMTQ SPSSLSASVG   180
DRVTITCRAS QSISSYLNWY QQKPGKAPKL LIYDASTLQS GVPSRFSGSG SGTDFTLTIS   240
SLQPEDFATY YCQQNDDNPS TFGQGTKVEI KRAAAHHHHH HGAAEQKLIS EEDL         294

SEQ ID NO: 23            moltype = DNA   length = 959
FEATURE                  Location/Qualifiers
variation                20
                         note = a, c, t, g, unknown or other
variation                55
                         note = a, c, t, g, unknown or other
variation                837..838
                         note = a, c, t, g, unknown or other
variation                875
                         note = a, c, t, g, unknown or other
variation                895
                         note = a, c, t, g, unknown or other
variation                906
                         note = a, c, t, g, unknown or other
variation                922
                         note = a, c, t, g, unknown or other
variation                944
                         note = a, c, t, g, unknown or other
variation                950
                         note = a, c, t, g, unknown or other
variation                954
                         note = a, c, t, g, unknown or other
source                   1..959
                         mol_type = other DNA
                         organism = synthetic construct
SEQUENCE: 23
ttcagatcct cttctgagan gagtttttgt tctgcggccc cgtgatggtg atgangatgt   60
gcggccgccc gtttgatttc caccttggtc ccttggccga acgtagtagg actagcataa   120
ctctgttgac agtagtaagt tgcaaaatct tcaggttgca gaccgctgat ggtgagagtg   180
aaatctgtcc cagatccact gccactgaac cttgatggga ccccactttg caaagaggat   240
gcaccataga tcaggagctt aggggctttc cctggtttct cctgatacca atttaaatag   300
ctgctaatgc tctgacttgc ccggcaagtg atggtgactc tgtctcctac agatgcagac   360
agggaggatg gagactgggt catctggatg tccgtcgacc cgccaccgcc gctgccacct   420
ccgcctgaac cgcctccacc gctcgagacg gtgaccaggg ttccctggcc ccagtagtca   480
aaagcagtag cagttttcgc acagtaatat acggccgtgt cctcggctct caggctgttc   540
atttgcagat acagcgtgtt cttggaattg tctctggaga tggtgaaccg gcccttcacg   600
gagtctgcgt aacttgtagc atcaccatta gaataaatag atgagaccca ctccagcccc   660
ttccctggag cctggcggac ccagctcatg gcatagctgc taaaggtgaa tccagaggct   720
gcacaggaga gtctcaggga cccccccaggc tgtaccaagc ctccccaga ctccaacagc    780
tgcacctcgg ccatggccgg ctgggccgcg agtaataaca atccagcggc tgccgtnnca   840
ataggtattt cattatgact gtctccttga aatanaattt gcatgcaagc ttggngtaat   900
catggncata gctgtttcct gngtgaaatt gttatccgct cacnattccn cacnacata    959

SEQ ID NO: 24            moltype = AA   length = 295
FEATURE                  Location/Qualifiers
VARIANT                  4
                         note = Any amino acid
VARIANT                  16
                         note = Any amino acid
VARIANT                  277
                         note = Any amino acid
VARIANT                  289
                         note = Any amino acid
source                   1..295
                         mol_type = protein
                         organism = synthetic construct
SEQUENCE: 24
MQIXFQGDSH NEIPIXTAAA GLLLLAAQPA MAEVQLLESG GGLVQPGGSL RLSCAASGFT   60
FSSYAMSWVR QAPGKGLEWV SSIYSNGDAT SYADSVKGRF TISRDNSKNT LYLQMNSLRA   120
EDTAVYYCAK TATAFDYWGQ GTLVTVSSGG GGSGGGGSGG GGSTDIQMTQ SPSSLSASVG   180
DRVTITCRAS QSISSYLNWY QQKPGKAPKL LIYDASSLQS GVPSRFSGSG SGTDFTLTIS   240
GLQPEDFATY YCQQSYASPT TFGQGTKVEI KRAAAHXHHH HGAAEQKLXS EEDLK        295
```

```
SEQ ID NO: 25          moltype = DNA   length = 971
FEATURE                Location/Qualifiers
variation              8
                       note = a, c, t, g, unknown or other
variation              33
                       note = a, c, t, g, unknown or other
variation              851
                       note = a, c, t, g, unknown or other
variation              914
                       note = a, c, t, g, unknown or other
variation              938
                       note = a, c, t, g, unknown or other
variation              952
                       note = a, c, t, g, unknown or other
variation              965..966
                       note = a, c, t, g, unknown or other
source                 1..971
                       mol_type = other DNA
                       organism = synthetic construct SEQUENCE: 25
ctatgcgncc ccattcagat cctcttctga gangagtttt tgttctgcgg ccccgtgatg   60
gtgatgatga tgtgcggccg cccgtttgat ttccaccttg gtcccttggc cgaacgtagg   120
aggcgaagtc tgaacctgtt gacagtagta agttgcaaaa tcttcaggtt gcagactgct   180
gatggtgaga gtgaaatctg tcccagatcc actgccactg aaccttgatg ggaccccact   240
ttgcaacagg gatgcacgat agatcaggag cttaggggct ttccctggtt tctgctgata   300
ccaatttaaa tagctgctaa tgctctggct tgcccggcaa gtgatggtga ctctgtctcc   360
tacagatgca gacagggagg atggagactg ggtcatctgg atgtccgtcg acccgccacc   420
gccgctgcca cctccgcctg aaccgcctcc accgctcgag acggtgacca gggttccctg   480
gccccagtag tcaaactgct taccacgttt cgcacagtaa tatacggccg tgtcctcggc   540
tctcaggctg ttcatttgca gatacagcgt gttcttggaa ttgtctctgg agatggtgaa   600
ccggcccttc acggagtctg cgtaatgtgt cacagtacca tccggccaaa tacctgagac   660
ccactccagc cccttccctg gagcctggcg gacccagctc atggcatagc tgctaaaggt   720
gaatccagag gctgcacagg agagtctcag ggacccccca ggctgtacca gcctcccccc   780
agactccaac agctgcacct cggccatggc cggctgggcc gcgagtaata acaatccagc   840
ggctgccgta ngcaataggt atttcattat gactgtctcc ttgaaataga atttgcatgc   900
aagcttggcg taancatggt catagctgtt tcctgtgnga aattgttatc cngctcacaa   960
ttccnncaca a                                                        971

SEQ ID NO: 26          moltype = AA   length = 288
FEATURE                Location/Qualifiers
VARIANT                6
                       note = Any amino acid
VARIANT                279
                       note = Any amino acid
VARIANT                287
                       note = Any amino acid
source                 1..288
                       mol_type = protein
                       organism = synthetic construct SEQUENCE: 26
MKYLLXTAAA GLLLLAAQPA MAEVQLLESG GGLVQPGGSL RLSCAASGFT FSSYAMSWVR   60
QAPGKGLEWV SGIWPDGTVT HYADSVKGRF TISRDNSKNT LYLQMNSLRA EDTAVYYCAK   120
RGKQFDYWGQ GTLVTVSSGG GGSGGGGSGG GGSTDIQMTQ SPSSLSASVG DRVTITCRAS   180
QSISSYLNWY QQKPGKAPKL LIYRASLLQS GVPSRFSGSG SGTDFTLTIS SLQPEDFATY   240
YCQQVQTSPP TFGQGTKVEI KRAAAHHHHH HGAAEQKLXS EEDLNGXA                288

SEQ ID NO: 27          moltype = DNA   length = 965
FEATURE                Location/Qualifiers
variation              7..9
                       note = a, c, t, g, unknown or other
variation              14
                       note = a, c, t, g, unknown or other
variation              30
                       note = a, c, t, g, unknown or other
variation              67..69
                       note = a, c, t, g, unknown or other
variation              747
                       note = a, c, t, g, unknown or other
variation              848
                       note = a, c, t, g, unknown or other
variation              855
                       note = a, c, t, g, unknown or other
variation              889
                       note = a, c, t, g, unknown or other
variation              907..908
                       note = a, c, t, g, unknown or other
variation              918..919
                       note = a, c, t, g, unknown or other
variation              960
```

-continued

```
                        note = a, c, t, g, unknown or other
variation               962
                        note = a, c, t, g, unknown or other
source                  1..965
                        mol_type = other DNA
                        organism = synthetic construct
SEQUENCE: 27
tatgcgnnna ttcngatcct cttctgagan gagtttttgt tctgcggccc cgtgatggtg    60
atgatgnnnt gcggccgccc gtttgatttc caccttggtc ccttggccga acgtattagg   120
acaatcagta gtctgttgac agtagtaagt tgcaaaatct tcaggttgca gactgctgat   180
ggtgagagtg aaatctgtcc cagatccact gccactgaac cttgatggga ccccactttg   240
caaagtggat gcattataga tcaggagctt aggggctttc cctggtttct gctgatacca   300
atttaaatag ctgctaatgc tctgacttgc ccggcaagtg atggtgactc tgtctcctac   360
agatgcagac agggaggatg gagactgggt catctggatg tccgtcgacc cgccaccgcc   420
gctgccacct ccgcctgaac cgcctccacc gctcgagacg gtgaccaggg ttccctggcc   480
ccagtagtca aaattagcac cagatttcgc acagtaatat acggccgtgt cctcggctct   540
caggctgttc atttgcagat acagcgtgtt cttggaattg tctctggaga tggtgaacct   600
gcccttcacg gagtctgcgt aagatgtagc ataaccacta gcagtaatac ctgagaccca   660
ctccagcccc ttccctggag cctggccggac ccagctcatg gcatagctgc taaaggtgaa   720
tccagaggct gcacaggaga gtctcangga ccccccaggc tgtaccaagc ctcccccaga   780
ctccaacagc tgcacctcgg ccatggccgg ctgggccgcg agtaataaca atccagcggc   840
tgccgtangc aatangtatt tcattatgac tgtctccttg aaatagaant ttgcatgcaa   900
gcttggnnta atcatggnna tagctgtttc ctgtgtgaaa ttgttatccg ctcacaattn   960
cncac                                                              965

SEQ ID NO: 28          moltype = AA  length = 305
FEATURE                Location/Qualifiers
VARIANT                3
                       note = Any amino acid
VARIANT                9
                       note = Any amino acid
VARIANT                21
                       note = Any amino acid
VARIANT                23
                       note = Any amino acid
VARIANT                57
                       note = Any amino acid
VARIANT                283
                       note = Any amino acid
VARIANT                296
                       note = Any amino acid
VARIANT                301
                       note = Any amino acid
VARIANT                303
                       note = Any amino acid
source                 1..305
                       mol_type = protein
                       organism = synthetic construct
SEQUENCE: 28
MIXPSLHAXF YFKETVIMKY XLXTAAAGLL LLAAQPAMAE VQLLESGGGL VQPGGSXRLS    60
CAASGFTFSS YAMSWVRQAP GKGLEWVSGI TASGYATSYA DSVKGRFTIS RDNSKNTLYL   120
QMNSLRAEDT AVYYCAKSGA NFDYWGQGTL VTVSSGGGGS GGGGSGGGGS TDIQMTQSPS   180
SLSASVGDRV TITCRASQSI SSYLNWYQQK PGKAPKLLIY NASTLQSGVP SRFSGSGSGT   240
DFTLTISSLQ PEDFATYYCQ QTTDCPNTFG QGTKVEIKRA AAXHHHHHGA AEQKLXSEED   300
XNXRI                                                              305

SEQ ID NO: 29          moltype = DNA  length = 963
FEATURE                Location/Qualifiers
variation              6..8
                       note = a, c, t, g, unknown or other
variation              12
                       note = a, c, t, g, unknown or other
variation              15
                       note = a, c, t, g, unknown or other
variation              28
                       note = a, c, t, g, unknown or other
variation              53..54
                       note = a, c, t, g, unknown or other
variation              62..66
                       note = a, c, t, g, unknown or other
variation              610
                       note = a, c, t, g, unknown or other
variation              839
                       note = a, c, t, g, unknown or other
variation              841
                       note = a, c, t, g, unknown or other
variation              846..847
                       note = a, c, t, g, unknown or other
variation              884..885
```

|            |                                                |     |
|------------|------------------------------------------------|-----|
|            | note = a, c, t, g, unknown or other            |     |
| variation  | 904                                            |     |
|            | note = a, c, t, g, unknown or other            |     |
| variation  | 908                                            |     |
|            | note = a, c, t, g, unknown or other            |     |
| variation  | 915                                            |     |
|            | note = a, c, t, g, unknown or other            |     |
| variation  | 927                                            |     |
|            | note = a, c, t, g, unknown or other            |     |
| variation  | 931                                            |     |
|            | note = a, c, t, g, unknown or other            |     |
| variation  | 935                                            |     |
|            | note = a, c, t, g, unknown or other            |     |
| variation  | 952..954                                       |     |
|            | note = a, c, t, g, unknown or other            |     |
| source     | 1..963                                         |     |
|            | mol_type = other DNA                           |     |
|            | organism = synthetic construct                 |     |

SEQUENCE: 29

```
gcggcnnntt cngancctct tctgaganga gtttttgttc tgcggccccg tgnnggtgat   60
gnnnnngtgc ggccgcccgt ttgatttcca ccttggtccc ttggccgaac gtattagggg  120
tactgtaact ctgttgacag tagtaagttg caaaatcttc aggttgcaga ctgctgatgg  180
tgagagtgaa atctgtccca gatccactgc cactgaacct tgatgggacc ccactttgca  240
aactggatgc agcatagatc aggagcttag gggctttccc tggtttctgc tgataccaat  300
ttaaatagct gctaatgctc tgacttgccc ggcaagtgat ggtgactctg tctcctacag  360
atgcagacag ggaggatgga gactgggtca tctggatgtc cgtcgacccg ccaccgccgc  420
tgccacctcc gcctgaaccg cctccaccgc tcgagacggt gaccagggtt ccctggcccc  480
agtagtcaaa cgccggatga tatttcgcac agtaatatac ggccgtgtcc tcggctctca  540
ggctgttcat ttgcagatac agcgtgttct tggaattgtc tctggagatg gtgaaccggc  600
ccttcacggn gtctgcgtac tctgtcggca gaccctgcgg cgcaatcgat gagacccact  660
ccagcccctt ccctggagcc tggcggaccc agctcatggc atagctgcta aaggtgaatc  720
cagaggctgc acaggagagt ctcagggacc ccccaggctg taccaagcct cccccagact  780
ccaacagctg cacctcggcc atggccggct gggccgcgag taataacaat ccagcggcng  840
ncgtanncaa taggtatttc attatgactg tctccttgaa atannatttg catgcaagct  900
tggngtgantc atggncatag ctgtttnctg ngtgnaaatt gttatccgct cnnnaatttc  960
cac                                                               963
```

| SEQ ID NO: 30 | moltype = AA  length = 283      |     |
|---------------|----------------------------------|-----|
| FEATURE       | Location/Qualifiers              |     |
| VARIANT       | 6                                |     |
|               | note = Any amino acid            |     |
| VARIANT       | 8                                |     |
|               | note = Any amino acid            |     |
| VARIANT       | 85                               |     |
|               | note = Any amino acid            |     |
| VARIANT       | 266..267                         |     |
|               | note = Any amino acid            |     |
| VARIANT       | 270                              |     |
|               | note = Any amino acid            |     |
| VARIANT       | 279                              |     |
|               | note = Any amino acid            |     |
| source        | 1..283                           |     |
|               | mol_type = protein               |     |
|               | organism = synthetic construct   |     |

SEQUENCE: 30

```
MKYLLXTXAA GLLLLAAQPA MAEVQLLESG GGLVQPGGSL RLSCAASGFT FSSYAMSWVR   60
QAPGKGLEWV SSIAPQGLPT EYADXVKGRF TISRDNSKNT LYLQMNSLRA EDTAVYYCAK  120
YHPAFDYWGQ GTLVTVSSGG GGSGGGGSGG GGSTDIQMTQ SPSSLSASVG DRVTITCRAS  180
QSISSYLNWY QQKPGKAPKL LIYAASSLQS GVPSRFSGSG SGTDFTLTIS SLQPEDFATY  240
YCQQSYSTPN TFGQGTKVEI KRAAAXXHHX HGAAEQKLXS EED                    283
```

| SEQ ID NO: 31 | moltype = DNA  length = 953     |     |
|---------------|----------------------------------|-----|
| FEATURE       | Location/Qualifiers              |     |
| variation     | 4                                |     |
|               | note = a, c, t, g, unknown or other |  |
| variation     | 7..8                             |     |
|               | note = a, c, t, g, unknown or other |  |
| variation     | 63..67                           |     |
|               | note = a, c, t, g, unknown or other |  |
| variation     | 688                              |     |
|               | note = a, c, t, g, unknown or other |  |
| variation     | 846                              |     |
|               | note = a, c, t, g, unknown or other |  |
| variation     | 853                              |     |
|               | note = a, c, t, g, unknown or other |  |
| variation     | 908                              |     |
|               | note = a, c, t, g, unknown or other |  |
| variation     | 915                              |     |
|               | note = a, c, t, g, unknown or other |  |

-continued

```
variation              924
                       note = a, c, t, g, unknown or other
variation              941
                       note = a, c, t, g, unknown or other
variation              943
                       note = a, c, t, g, unknown or other
source                 1..953
                       mol_type = other DNA
                       organism = synthetic construct
SEQUENCE: 31
gcgnccnntt cagatcctct tctgagatga gtttttgttc tgcggccccg tgatggtgat    60
gannnnntgc ggccgcccgt ttgatttcca ccttggtccc ttggccgaac gtagaaggag   120
aattaccagt ctgttgacag tagtaagttg caaaatcttc aggttgcaga ctgctgatgg   180
tgagagtgaa atctgtccca gatccactgc cactgaacct tgatgggacc ccactttgca   240
aagcggatgc agtatagatc aggagcttag gggctttccc tggtttctgc tgataccaat   300
ttaaatagct gctaatgctc tgacttgccc ggcaagtgat ggtgactctg tctcctacag   360
atgcagacag ggaggatgga gactgggtca tctggatgtc cgtcgacccg ccaccgccgc   420
tgccacctcc gcctgaaccg cctccaccgc tcgagacggt gaccagggtt ccctggcccc   480
agtagtcaaa agtactataa gatttcgcac agtaatatac ggccgtgtcc tcggctctca   540
ggctgttcat ttgcagatac agcgtgttct tggaattgtc tctggagatg gtgaaccggc   600
ccttcacgga gtctgcgtaa gctgtactag cactactagc agcaatacct gagacccact   660
ccagcccctt ccctggagcc tggcggancc agctcatggc atagctgcta aaggtgaatc   720
cagaggctgc acaggagagt ctcagggacc ccccaggctg taccaagcct cccccggact   780
ccaacagctg cacctcggcc atggccggct gggccgcgag taataacaat ccagcggctg   840
ccgtangcaa tangtatttc attatgactg tctccttgaa atagaatttg catgcaagct   900
tggcgtantc atggncatag ctgnttcctg tgtgaaattg ntnatccgct cac           953

SEQ ID NO: 32           moltype = AA  length = 284
FEATURE                 Location/Qualifiers
VARIANT                 4
                        note = Any amino acid
VARIANT                 6
                        note = Any amino acid
VARIANT                 59
                        note = Any amino acid
VARIANT                 266..267
                        note = Any amino acid
source                  1..284
                        mol_type = protein
                        organism = synthetic construct
SEQUENCE: 32
MKYXLXTAAA GLLLLAAQPA MAEVQLLESG GGLVQPGGSL RLSCAASGFT FSSYAMSWXR    60
QAPGKGLEWV SGIAASSAST AYADSVKGRF TISRDNSKNT LYLQMNSLRA EDTAVYYCAK   120
SYSTFDYWGQ GTLVTVSSGG GGSGGGGSGG GGSTDIQMTQ SPSSLSASVG DRVTITCRAS   180
QSISSYLNWY QQKPGKAPKL LIYTASALQS GVPSRFSGSG SGTDFTLTIS SLQPEDFATY   240
YCQQTGNSPS TFGQGTKVEI KRAAAXXHHH HGAAEQKLIS EEDL                    284

SEQ ID NO: 33           moltype = DNA  length = 696
FEATURE                 Location/Qualifiers
source                  1..696
                        mol_type = other DNA
                        organism = synthetic construct
SEQUENCE: 33
atggccgagg tgcagctgtc ggagtctggg ggaggcttgg tacagcctgg ggggtccctg    60
agactctcct gtgcagcctc tggattcacc tttagcagct atgccatgag ctgggtcgtg   120
caggctccag ggaaggggct ggagtgggtc tcaggtatta atagtaatgg tacttctaca   180
tcttacgcag actccgtgaa gggccggttc accatctcca gagacaattc caagaacacg   240
ctgtatctgc aaatgaacag cctgagagcc gaggacacgg ccgtatatta ctgtgcgaaa   300
tctgcttctg attttgacta ctggggccag ggaaccctgg tcaccgtctc gagcggtgga   360
ggcggttcag gcggaggtgg cagcggcggt ggcgggtcga cggacatcca gatgacccag   420
tctccatcct ccctgtctgc atctgtagga gacagagtca ccatcacttg ccgggcaagt   480
cagagcatta gcagctattt aaattggtat cagcagaaac agggaaagc ccctaagctc    540
ctgatctata atgcatccac tttgcaaagt ggggtcccat caaggttcag tggcagtgga   600
tctgggacag atttcactct caccatcagc agtctgcaac ctgaagattt tgcaacttac   660
tactgtcaac agaatactta tagtcctact acgttc                             696

SEQ ID NO: 34           moltype = AA  length = 264
FEATURE                 Location/Qualifiers
source                  1..264
                        mol_type = protein
                        organism = synthetic construct
SEQUENCE: 34
MKYLLPTNAA GLLLLAANPA MAEVQLSESG GGLVQPGGSL RLSCAASGFT FSSYAMSWVR    60
QAPGKGLEWV SGINSNGTST SYADSVKGRF TISRDNSKNT LYLQMNSLRA EDTAVYYCAK   120
SASDFDYWGQ GTLVTVSSGG GGSGGGGSGG GGSTDIQMTQ SPSSLSASVG DRVTITCRAS   180
QSISSYLNWY QQKPGKAPKL LIYNASTLQS GVPSRFSGSG SGTDFTLTIS SLQPEDFATY   240
YCQQNTYSPT TFGNNNKVEI KRAA                                         264

SEQ ID NO: 35           moltype = DNA  length = 732
```

```
FEATURE              Location/Qualifiers
variation            706
                     note = a, c, t, g, unknown or other
source               1..732
                     mol_type = other DNA
                     organism = synthetic construct
SEQUENCE: 35
atggccgaga tgcagctgtt ggagtctggg ggaggcttgg tacagcctgg ggggtccctg   60
agactctcct gtgcagcctc tggattcacc tttagcagct atgccatgag ctgggtccgc  120
caggctccag ggaaggggct ggagtgggtc tcatatatta ctgctaatgg tgatagtaca  180
acttacgcag actccgtgaa gggccggttc accatctcca gagacaattc caagaacacg  240
ctgtatctgc aaatgaacag cctgagagcc gaggacacgg ccgtatatta ctgtgcgaaa  300
agtactactg attttgacta ctggggccag ggaaccctgg tcaccgtctc gagcggtgga  360
ggcggttcag gcggaggtgg cagcggcggt ggcgggtcag gacatcca gatgacccag  420
tctccatcct ccctgtctgc atctgtagga gacagagtca ccatcacttg ccgggcaagt  480
cagagcatta gcagctattt aaattggtat cagcagaaac cagggaaagc ccctaagctc  540
ctgatctata gtgcatccaa tttgcaaagt ggggtcccat caaggttcag tggcagtgga  600
tctgggacag atttcactct caccatcagc agtctgcaac ctgaagattt tgcaacttac  660
tactgtcaac agacttctta tagtccttct acgttcggcc aagggnccaa ggtggaaatc  720
aaacgggcgg cc                                                      732

SEQ ID NO: 36         moltype = AA   length = 245
FEATURE              Location/Qualifiers
VARIANT              236
                     note = Any amino acid
source               1..245
                     mol_type = protein
                     organism = synthetic construct
SEQUENCE: 36
MAEMQLLESG GGLVQPGGSL RLSCAASGFT FSSYAMSWVR QAPGKGLEWV SYITANGDST   60
TYADSVKGRF TISRDNSKNT LYLQMNSLRA EDTAVYYCAK STTDFDYWGQ GTLVTVSSGG  120
GGSGGGGSGG GGSTDIQMTQ SPSSLSASVG DRVTITCRAS QSISSYLNWY QQKPGKAPKL  180
LIYSASNLQS GVPSRFSGSG SGTDFTLTIS SLQPEDFATY YCQQTSYSPS TFGQGXKVEI  240
KRAAA                                                              245

SEQ ID NO: 37         moltype = DNA   length = 735
FEATURE              Location/Qualifiers
variation            54
                     note = a, c, t, g, unknown or other
source               1..735
                     mol_type = other DNA
                     organism = synthetic construct
SEQUENCE: 37
atggccgagg tgcagctgtt ggagtctggg ggaggcttgg tacagcctgg gggntccctg   60
agactctcct gtgcagcctc tggattcacc tttagcagct atgccatgag ctgggtccgc  120
caggctccag ggaaggggct ggagtgggtc tcaactatta atgctagtgg tggtagtaca  180
ggttacgcag actccgtgaa gggccggttc accatctcca gagacaattc caagaacacg  240
ctgtatctgc aaatgaacag cctgagagcc gaggacacgg ccgtatatta ctgtgcgaaa  300
gctgatgctt attttgacta ctggggccag ggaaccctgg tcaccgtctc gagcggtgga  360
ggcggttcag gcggaggtgg cagcggcggt ggcgggtcga cggacatcca gatgacccag  420
tctccatcct ccctgtctgc atctgtagga gacagagtca ccatcacttg ccgggcaagt  480
cagagcatta gcagctattt aaattggtat cagcagaaac cagggaaagc ccctaagctc  540
ctgatctatt ctgcatcctc gttgcaaagt ggggtcccat caaggttcag tggcagtgga  600
tctgggacag atttcactct caccatcagc agtctgcaac ctgaagattt tgcaacttac  660
tactgtcaac aggatgctag tggtccttct acgttcggcc aagggaccaa ggtggaaatc  720
aaacgggcgg ccgca                                                   735

SEQ ID NO: 38         moltype = AA   length = 244
FEATURE              Location/Qualifiers
source               1..244
                     mol_type = protein
                     organism = synthetic construct
SEQUENCE: 38
MAEVQLLESG GGLVQPGGSL RLSCAASGFT FSSYAMSWVR QAPGKGLEWV STINASGGST   60
GYADSVKGRF TISRDNSKNT LYLQMNSLRA EDTAVYYCAK ADAYFDYWGQ GTLVTVSSGG  120
GGSGGGGSGG GGSTDIQMTQ SPSSLSASVG DRVTITCRAS QSISSYLNWY QQKPGKAPKL  180
LIYSASSLQS GVPSRFSGSG SGTDFTLTIS SLQPEDFATY YCQQDASGPS TFGQGTKVEI  240
KRAA                                                               244

SEQ ID NO: 39         moltype = DNA   length = 736
FEATURE              Location/Qualifiers
variation            706
                     note = a, c, t, g, unknown or other
variation            731
                     note = a, c, t, g, unknown or other
source               1..736
                     mol_type = other DNA
                     organism = synthetic construct
SEQUENCE: 39
```

-continued

```
atggccgagg tgcagctgtt ggagtctggg ggaggcttgg tacagcctgg ggggtccctg  60
agactctcct gtgcagcctc tggattcacc tttagcagct atgccatgag ctgggtccgc  120
caggctccag ggaaggggct ggagtgggtc tcatatattg ctgatgatgg tgctaataca  180
gcttacgcag actccgtgaa gggccggttc accatctcca gagacaattc caagaacacg  240
ctgtatctgc aaatgaacag cctgagagcc gaggacacgg ccgtatatta ctgtgcgaaa  300
aataatgatg gttttgacta ctggggccag ggaaccctgg tcaccgtctc gagcggtgga  360
ggcggttcag gcggaggtgg cagcggcggt ggcgggtcga cgaacatcca gatgacccag  420
tctccatcct ccctgtctgc atctgtagga gacagagtca ccatcacttg ccgggcaagt  480
cagagcatta gcagctattt aaattggtat cagcagaaac cagggaaagc ccctaagctc  540
ctgatctatt ctgcatccac tttgcaaagt ggggtcccat caaggttcag tggcagtgga  600
tctgggacag atttcactct caccatcagc agtctgcaac ctgaagattt tgcaacttac  660
tactgtcaac aggctgctac tagtccttct acgttcggcc aagggnccaa ggtggaaatc  720
aaacgggcgg ncgcac  736
```

SEQ ID NO: 40          moltype = AA  length = 245
FEATURE                Location/Qualifiers
VARIANT                236
                       note = Any amino acid
VARIANT                244
                       note = Any amino acid
source                 1..245
                       mol_type = protein
                       organism = synthetic construct
SEQUENCE: 40
```
MAEVQLLESG GGLVQPGGSL RLSCAASGFT FSSYAMSWVR QAPGKGLEWV SYIADDGANT  60
AYADSVKGRF TISRDNSKNT LYLQMNSLRA EDTAVYYCAK NNDGFDYWGQ GTLVTVSSGG  120
GGSGGGGSGG GGSTNIQMTQ SPSSLSASVG DRVTITCRAS QSISSYLNWY QQKPGKAPKL  180
LIYSASTLQS GVPSRFSGSG SGTDFTLTIS SLQPEDFATY YCQQAATSPS TFGQGXKVEI  240
KRAXA  245
```

SEQ ID NO: 41          moltype = DNA  length = 886
FEATURE                Location/Qualifiers
variation              27
                       note = a, c, t, g, unknown or other
variation              36
                       note = a, c, t, g, unknown or other
variation              44..45
                       note = a, c, t, g, unknown or other
variation              76
                       note = a, c, t, g, unknown or other
variation              78
                       note = a, c, t, g, unknown or other
variation              852
                       note = a, c, t, g, unknown or other
variation              875..876
                       note = a, c, t, g, unknown or other
variation              885
                       note = a, c, t, g, unknown or other
source                 1..886
                       mol_type = other DNA
                       organism = synthetic construct
SEQUENCE: 41
```
ttcaaggaga cagtcataat gaaatanect attgcntacg gcanncgctg gattgttatt  60
actcgcggcc cagccngncc atggccgagg tgcagctgtt ggagtctggg ggaggcttgg  120
tacagcctgg ggggtccctg agactctcct gtgcagcctc tggattcacc tttagcagct  180
atgccatgag ctgggtccgc caggctccag ggaaggggct ggagtgggtc tcaaatatta  240
gttctgatgg tgattctaca gcttacgcag actccgtgaa gggccggttc accatctcca  300
gagacaattc caagaacacg ctgtatctgc aaatgaacag cctgagagcc gaggacacgg  360
ccgtatatta ctgtgcgaaa gcttctagta attttgacta ctggggccag ggaaccctgg  420
tcaccgtctc gagcggtgga ggcggttcag gcggaggtgg cagcggcggt ggcgggtcga  480
cggacatcca gatgacccag tctccatcct ccctgtctgc atctgtagga gacagagtca  540
ccatcacttg ccgggcaagt cagagcatta gcagctattt aaattggtat cagcagaaac  600
cagggaaagc ccctaagctc ctgatctatg ctgcatccaa tttgcaaagt ggggtcccat  660
caaggttcag tggcagtgga tctgggacag atttcactct caccatcagc agtctgcaac  720
ctgaagattt tgcaacttac tactgtcaac agtctaattc tgatcctact acgttcggcc  780
aagggaccaa ggtaatcaaa cgggcggccg cacatcatca tcaccatcac ggggccgcag  840
aacaaaaact cntctcagaa gaggatctga atggnnccgc atagnc  886
```

SEQ ID NO: 42          moltype = AA  length = 267
FEATURE                Location/Qualifiers
VARIANT                258
                       note = Any amino acid
VARIANT                265..266
                       note = Any amino acid
source                 1..267
                       mol_type = protein
                       organism = synthetic construct
SEQUENCE: 42
```
MAEVQLLESG GGLVQPGGSL RLSCAASGFT FSSYAMSWVR QAPGKGLEWV SNISSDGDST  60
```

```
AYADSVKGRF TISRDNSKNT LYLQMNSLRA EDTAVYYCAK ASSNFDYWGQ GTLVTVSSGG   120
GGSGGGGSGG GGSTDIQMTQ SPSSLSASVG DRVTITCRAS QSISSYLNWY QQKPGKAPKL   180
LIYAASNLQS GVPSRFSGSG SGTDFTLTIS SLQPEDFATY YCQQSNSDPT TFGQGTKVIK   240
RAAAHHHHHH GAAEQKLXSE EDLNXXA                                      267

SEQ ID NO: 43           moltype = DNA   length = 909
FEATURE                 Location/Qualifiers
variation               13
                        note = a, c, t, g, unknown or other
variation               21
                        note = a, c, t, g, unknown or other
variation               907
                        note = a, c, t, g, unknown or other
source                  1..909
                        mol_type = other DNA
                        organism = synthetic construct
SEQUENCE: 43
caggggggc ggngcctatg naaaaaacgc cagcaacgcg gccttttacg gttcctggcc    60
ctttgctggc cttttgctca catgttcttt cctgcgttat cccctgattc tgtggataac   120
cgtattaccg cctttgagtg agctgatacc gctcgccgca gccgaacgac cgagcgcagc   180
gagtcagtga gcgaggaagc ggaagagcgc ccaatacgaa aaccgcctct ccccgcgcgt   240
tggccgattc attaatgcag ctggcacgac aggtttcccg actggaaagc gggcagtgag   300
cgcaacgcaa ttaatgtgag ttagctcact cattaggcac cccaggcttt acactttatg   360
ctccggctc gtatgttgtg tggaattgtg agcggataac aatttcacac aggaaacagc    420
tatgaccatg attacgccaa gcttgcatgc aaattctatt tcaaggagac agtcatagct   480
agcatgaaaa agatttggct ggcgctggct ggtttagttt tagcgtttag cgcatcggcg   540
gactacaaag aggcccagcc ggccatggac ctgggtaaga aactgctgga agctgctcgt   600
gctggtcagg acgacgaagt tcgtatcctg atggctaacg gtgctgacgt taacgctcat   660
gacgaacagg gtactactcc gctgcacctg gctgctaaag aaggtcacct ggaaatcgtt   720
gaagttctgc tgaagtacgg tgctgacgtt aacgctcaag acaaattcgg taagaccgct   780
ttcgacatct ccatcgacaa cggtaacgag gacctggctg aaatcctgca agcggccgca   840
catcatcatc accatcacgg ggccgcagaa caaaaactca tctcagaaga ggatctgaat   900
ggccgcnta                                                          909

SEQ ID NO: 44           moltype = AA   length = 183
FEATURE                 Location/Qualifiers
VARIANT                 183
                        note = Any amino acid
source                  1..183
                        mol_type = protein
                        organism = synthetic construct
SEQUENCE: 44
MLPARMLCGI VSGQFHTGNS YDHDYAKLAC KFYFKETVIA SMKKIWLALA GLVLAFSASA    60
DYKEAQPAMD LGKKLLEAAR AGQDDEVRIL MANGADVNAH DEQGTTPLHL AAKEGHLEIV   120
EVLLKYGADV NAQDKFGKTA FDISIDNGNE DLAEILQAAA HHHHHHGAAE QKLISEEDLN   180
GRX                                                                183

SEQ ID NO: 45           moltype = DNA   length = 930
FEATURE                 Location/Qualifiers
variation               12..17
                        note = a, c, t, g, unknown or other
variation               30
                        note = a, c, t, g, unknown or other
variation               64
                        note = a, c, t, g, unknown or other
variation               98..99
                        note = a, c, t, g, unknown or other
variation               101
                        note = a, c, t, g, unknown or other
variation               139..140
                        note = a, c, t, g, unknown or other
variation               898
                        note = a, c, t, g, unknown or other
variation               914
                        note = a, c, t, g, unknown or other
variation               918..922
                        note = a, c, t, g, unknown or other
variation               926
                        note = a, c, t, g, unknown or other
source                  1..930
                        mol_type = other DNA
                        organism = synthetic construct
SEQUENCE: 45
gagctatgag annnnnncca cgcttccccn aagggagaaa ggcggacagg tatcccggta    60
agcnggcagg gtcggaacag gagagcgcac gagggagnnt ncaggggaa acgcctggta    120
tctttatagt cctgtcggnn tttcgccacc tctgacttga gcgtcgattt tttgtgatgc   180
tcgtcagggg ggcggagcct atggaaaaac gccagcaacg cggccttttt acggttcctg   240
gccttttgct ggccttttgc tcacatgttc tttcctgcgt tatcccctga ttctgtggat   300
aaccgtatta ccgcctttga gtgagctgat accgctcgcc gcagccgaac gaccgagcgc   360
```

```
agcgagtcag tgagcgagga agcggaagag cgcccaatac gcaaaccgcc tctccccgcg   420
cgttggccga ttcattaatg cagctggcac gacaggtttc ccgactggaa agcgggcagt   480
gagcgcaacg caattaatgt gagttagctc actcattagg cacccaggc tttacacttt     540
atgctcccgg ctcgtatgtt gtgtggaatt gtgagcggat aacaatttca cacaggaaac   600
agctatgacc atgattacgc caagcttgca tgcaaattct atttcaagga gacagtcata   660
gctagcatga aaaagatttg gctggcgctg gctggtttag ttttagcgtt tagcgcatcg   720
gcggactaca aagaggccca gccggccatg gtaggaagac ctgacgttaa cgctcaggac   780
aaaattcggta agaccgcttt cgacatctcc atcgacaacg gtaacgagga cctggctgaa   840
atcctgcaag cggccgcaca tcatcatcac catcacgggg ccgcagaaca aaaactcntc   900
tcagaagagg atcngaannn nncgcntaga                                     930
```

```
SEQ ID NO: 46              moltype = AA  length = 211
FEATURE                    Location/Qualifiers
VARIANT                    207
                           note = Any amino acid
source                     1..211
                           mol_type = protein
                           organism = synthetic construct
SEQUENCE: 46
MFFPALSPDS VDNRITAFEA DTARRSRTTE RSESVSEEAE ERPIRKPPLP ARWPIHCSWH     60
DRFPDWKAGS ERNAINVSLT HAPQALHFML PARMLCGIVS GQFHTGNSYD HDYAKLACKF    120
YFKETVIASM KKIWLALAGL VLAFSASADY KEAQPAMVGR PDVNAQDKFG KTAFDISIDN    180
GNEDLAEILQ AAAHHHHHHG AAEQKLXSEE D                                   211
```

```
SEQ ID NO: 47              moltype = DNA  length = 915
FEATURE                    Location/Qualifiers
variation                  13
                           note = a, c, t, g, unknown or other
variation                  17
                           note = a, c, t, g, unknown or other
variation                  35..36
                           note = a, c, t, g, unknown or other
variation                  44
                           note = a, c, t, g, unknown or other
variation                  46
                           note = a, c, t, g, unknown or other
variation                  48
                           note = a, c, t, g, unknown or other
variation                  58..61
                           note = a, c, t, g, unknown or other
variation                  77
                           note = a, c, t, g, unknown or other
variation                  104..105
                           note = a, c, t, g, unknown or other
variation                  124
                           note = a, c, t, g, unknown or other
variation                  141
                           note = a, c, t, g, unknown or other
variation                  158
                           note = a, c, t, g, unknown or other
variation                  901..902
                           note = a, c, t, g, unknown or other
variation                  906
                           note = a, c, t, g, unknown or other
variation                  908..910
                           note = a, c, t, g, unknown or other
source                     1..915
                           mol_type = other DNA
                           organism = synthetic construct
SEQUENCE: 47
tcgtcagggg ggncggnagc ctatggaaaa aacgnnagca acgngncntt tttacggnnn     60
ntggcctttt gctggcnttt gctcacatgt tctttcctgc gttnnccct gattctgtgg     120
atanccgtat taccgccttt ngagtgagct gataccgntc gccgcagccg aacgaccgag    180
cgcagcgagt cagtgagcga ggaagcgaa gagcgcccaa tacgcaaacc gcctctcccc     240
gcgcgttggc cgattcatta atgcagctgg cacgacaggt ttcccgactg gaaagcgggc    300
agtgagcgca acgcaattaa tgtgagttag ctcactcatt aggcacccca ggctttacac    360
tttatgctcc cggctcgtat gttgtgtgga attgtgagcg ataacaatt tcacacagga     420
aacagctatg accatgatta cgccaagctt gcatgcaaat tctatttcaa ggagacagtc    480
atagctagca tgaaaaagat ttggctggcg ctggctggtt tagtttttagc gtttagcgc    540
tcggcggact acaaagaggc ccagccggcc atggacctgg gtaagaaact gctggaagct    600
gctcgtgctg tcaggacga cgaagttcgt atcctgatgg ctaacggtgc tgacgttaac    660
gcttgggaca tgactggtca tactccgctg cacctggctg ctcagttcgg tcacctggaa    720
atcgttgaag ttctgctgaa gcacggtgct gacgttaacg ctcaggacaa attcggtaag    780
accgctttcg acatctccat cgacaacggt aacgaggacc tggctgaaat cctgcaagcg    840
gccgcacatc atcatcacca tcacgggggcc gcagaacaaa aactcatctc agaagaggat    900
nngaangnnn ccgca                                                      915
```

```
SEQ ID NO: 48              moltype = AA  length = 178
FEATURE                    Location/Qualifiers
```

```
source                  1..178
                        mol_type = protein
                        organism = synthetic construct
SEQUENCE: 48
MLPARMLCGI VSGQFHTGNS YDHDYAKLAC KFYFKETVIA SMKKIWLALA GLVLAFSASA  60
DYKEAQPAMD LGKKLLEAAR AGQDDEVRIL MANGADVNAW DMTGHTPLHL AAQFGHLEIV  120
EVLLKHGADV NAQDKFGKTA FDISIDNGNE DLAEILQAAA HHHHHHGAAE QKLISEED     178

SEQ ID NO: 49          moltype = DNA  length = 848
FEATURE                Location/Qualifiers
variation              9
                       note = a, c, t, g, unknown or other
variation              11
                       note = a, c, t, g, unknown or other
variation              23
                       note = a, c, t, g, unknown or other
variation              28
                       note = a, c, t, g, unknown or other
variation              30
                       note = a, c, t, g, unknown or other
variation              35
                       note = a, c, t, g, unknown or other
variation              41
                       note = a, c, t, g, unknown or other
variation              47
                       note = a, c, t, g, unknown or other
variation              51..54
                       note = a, c, t, g, unknown or other
variation              60..61
                       note = a, c, t, g, unknown or other
variation              89
                       note = a, c, t, g, unknown or other
variation              100
                       note = a, c, t, g, unknown or other
variation              102
                       note = a, c, t, g, unknown or other
variation              106
                       note = a, c, t, g, unknown or other
variation              108
                       note = a, c, t, g, unknown or other
variation              114..115
                       note = a, c, t, g, unknown or other
variation              118
                       note = a, c, t, g, unknown or other
variation              120
                       note = a, c, t, g, unknown or other
variation              152
                       note = a, c, t, g, unknown or other
variation              164
                       note = a, c, t, g, unknown or other
variation              170
                       note = a, c, t, g, unknown or other
variation              179
                       note = a, c, t, g, unknown or other
variation              221..222
                       note = a, c, t, g, unknown or other
variation              240
                       note = a, c, t, g, unknown or other
variation              292
                       note = a, c, t, g, unknown or other
variation              337..339
                       note = a, c, t, g, unknown or other
variation              480
                       note = a, c, t, g, unknown or other
variation              603
                       note = a, c, t, g, unknown or other
variation              645
                       note = a, c, t, g, unknown or other
variation              707
                       note = a, c, t, g, unknown or other
variation              719
                       note = a, c, t, g, unknown or other
variation              753
                       note = a, c, t, g, unknown or other
source                 1..848
                       mol_type = other DNA
                       organism = synthetic construct
SEQUENCE: 49
tttatagtnc ntgtcgggtt tcnccacntn tgacntgagc ntcgatnttt nnnntgctcn  60
```

```
ncaggggggc ggagcctatg gaaaaacgnc agcaacgcgn cntttntncg gttnntgncn   120
ttttgctggc cttttgctca catgttcttt cntgcgttat cccntgattn tgtggatanc   180
cgtattaccg cctttgagtg agctgatacc gctcgccgca nncgaacgac cgagcgcagn   240
gagtcagtga gcgaggaagc ggaagagcgc ccaatacgca aaccgcctct cnccgcgcgt   300
tggccgattc attaatgcag ctggcacgac aggtttnnng actggaaagc gggcagtgag   360
cgcaacgcaa ttaatgtgag ttagctcact cattaggcac cccaggcttt acactttatg   420
ctcccggctc gtatgttgtg tggaattgtg agcggataac aatttcacac aggaaacagn   480
tatgaccatg attacgccaa gcttgcatgc aaattctatt tcaaggagac agtcatagct   540
agcatgaaaa agatttggct ggcgctggct ggtttagttt tagcgtttag cgcatcggcg   600
gantacaaag aggcccagcc ggccatgggc ggaaccagca gtttnttacc caggtccatg   660
gacctgggtc acctggaaat cgttgaagtt ctgctgaagt acggtgntga cgttaacgnt   720
caggacaaat tcggtaagac cgctttcgac atntccatcg acaacggtaa cgaggacctg   780
gctgaaatcc tgcaagcggc cgcacatcat catcaccatc atcgggctcg cagaacaaaa   840
atcatctc                                                             848
```

```
SEQ ID NO: 50              moltype = AA  length = 230
FEATURE                    Location/Qualifiers
VARIANT                    4
                           note = Any amino acid
VARIANT                    8
                           note = Any amino acid
VARIANT                    10
                           note = Any amino acid
VARIANT                    13
                           note = Any amino acid
VARIANT                    26
                           note = Any amino acid
VARIANT                    32
                           note = Any amino acid
VARIANT                    50
                           note = Any amino acid
VARIANT                    64
                           note = Any amino acid
VARIANT                    108
                           note = Any amino acid
VARIANT                    149
                           note = Any amino acid
VARIANT                    163
                           note = Any amino acid
VARIANT                    184
                           note = Any amino acid
VARIANT                    188
                           note = Any amino acid
VARIANT                    199
                           note = Any amino acid
source                     1..230
                           mol_type = protein
                           organism = synthetic construct
SEQUENCE: 50
MFFXALSXDX VDXRITAFEA DTARRXRTTE RXESVSEEEA ERPIRKPPLX ARWPIHCSWH    60
DRFXDWKAGS ERNAINVSLT HAPQALHFML PARMLCGIVS GQFHTGNXYD HDYAKLACKF   120
YFKETVIASM KKIWLALAGL VLAFSASAXY KEAQPAMGGT SSXLPRSMDL GHLEIVEVLL   180
KYGXDVNXQD KFGKTAFDXS IDNGNEDLAE ILQAAHHHH HHRARRTKII              230
```

```
SEQ ID NO: 51              moltype = DNA  length = 900
FEATURE                    Location/Qualifiers
variation                  33
                           note = a, c, t, g, unknown or other
variation                  59
                           note = a, c, t, g, unknown or other
variation                  61
                           note = a, c, t, g, unknown or other
variation                  63
                           note = a, c, t, g, unknown or other
variation                  69
                           note = a, c, t, g, unknown or other
variation                  133..136
                           note = a, c, t, g, unknown or other
variation                  833..838
                           note = a, c, t, g, unknown or other
variation                  872..874
                           note = a, c, t, g, unknown or other
variation                  886..887
                           note = a, c, t, g, unknown or other
variation                  891..894
                           note = a, c, t, g, unknown or other
source                     1..900
                           mol_type = other DNA
                           organism = synthetic construct
```

-continued

```
SEQUENCE: 51
gagcctatgg aaaaaacgcc cagcaacgcg gcnttttttac ggttcctggc cttttgctng   60
ncnttttgnt cacatgttct ttcctgcgtt atcccctgat tctgtggata accgtattac   120
cgcctttgag tgnnnngata ccgctcgccg cagccgaacg accgagcgca gcgagtcagt   180
gagcgaggaa gcggaagagc gcccaatacg caaaccgcct ctccccgcgc gttggccgat   240
tcattaatgc agctggcacg acaggtttcc cgactggaaa gcgggcagtg agcgcaacgc   300
aattaatgtg agttagctca ctcattaggc accccaggct ttacacttta tgctcccggc   360
tcgtatgttg tgtggaattg tgagcggata acaatttcac acaggaaaca gctatgacca   420
tgattacgcc aagcttgcat gcaaattcta tttcaaggag acagtcatag ctagcatgaa   480
aaagatttgg ctggcgctgg ctggtttagt tttagcgttt agcgcatcgg cggactacaa   540
agaggcccag ccggccatgg acctgggtaa gaaactgctg gaagctgctc gtgctggtca   600
ggacgacgaa gttcgtatcc tgatggctaa cggtgctgac gttaacgctg acgacttctc   660
tggtactact ccgctgcacc tggctgctca tcatggtcac ctggaaatcg ttgaagttct   720
gctgaagtac ggtgctgacg ttaacgctca ggacaaattc ggtaagaccg ctttcgacat   780
ctccatcgac aacggtaacg aggacctggc tgaaatcctg caagcggccg cannnnnnca   840
tcaccatcac ggggccgcag aacaaaaact cnnncagaag aggatnngaa nnnncgcata   900

SEQ ID NO: 52          moltype = AA   length = 263
FEATURE                Location/Qualifiers
VARIANT                20..21
                       note = Any amino acid
VARIANT                250..251
                       note = Any amino acid
VARIANT                263
                       note = Any amino acid
source                 1..263
                       mol_type = protein
                       organism = synthetic construct
SEQUENCE: 52
MFFPALSPDS VDNRITAFEX XDTARRSRTT ERSESVSEEA EERPIRKPPL PARWPIHCSW   60
HDRFPDWKAG SERNAINVSL THAPQALHFM LPARMLCGIV SGQFHTGNSY DHDYAKLACK   120
FYFKETVIAS MKKIWLALAG LVLAFSASAD YKEAQPAMDL GKKLLEAARA GQDDEVRILM   180
ANGADVNADD FSGTTPLHLA AHHGHLEIVE VLLKYGADVN AQDKFGKTAF DISIDNGNED   240
LAEILQAAAX XHHHHGAAEQ KLX                                          263

SEQ ID NO: 53          moltype = DNA   length = 919
FEATURE                Location/Qualifiers
variation              3
                       note = a, c, t, g, unknown or other
variation              5
                       note = a, c, t, g, unknown or other
variation              8..9
                       note = a, c, t, g, unknown or other
variation              29
                       note = a, c, t, g, unknown or other
variation              52
                       note = a, c, t, g, unknown or other
variation              130
                       note = a, c, t, g, unknown or other
variation              910..912
                       note = a, c, t, g, unknown or other
variation              916
                       note = a, c, t, g, unknown or other
source                 1..919
                       mol_type = other DNA
                       organism = synthetic construct
SEQUENCE: 53
gangntcnnc agggggggcg gagcctatng aaaaaacgcc agcaacgcgg cnttttttac   60
ggttcctggc cttttgctgg cctttttgctc acatgttctt tcctgcgtta tcccctgatt   120
ctgtggatan ccgtattacc gcctttgagt gagctgatac cgctcgccgc agccgaacga   180
ccgagcgcag cgagtcagtg agcgaggaag cggaagagcg cccaatacgc aaaccgcctc   240
tccccgcgcg ttggccgatt cattaatgca gctggcacga caggtttccc gactggaaag   300
cgggcagtga gcgcaacgca attaatgtga gttagctcac tcattaggca ccccaggctt   360
tacactttat gctcccggct cgtatgttgt gtggaattgt gagcggataa caatttcaca   420
caggaaacag ctatgaccat gattacgcca agcttgcatg caaattctat ttcaaggaga   480
cagtcatagc tagcatgaaa aagatttggc tggcgctggc tggtttagtt ttagcgttta   540
gcgcatcggc ggactacaaa gaggcccagc cggccatgga cctgggtaag aaactgctgg   600
aagctgctcg tgctggtcag gacgacgaag ttcgtatcct gatggctaac ggtgctgacg   660
ttaacgctct ggacgaagtt ggttctactc cgctgcacct ggctgctatg ggtggtcacc   720
tggaaatcgt tgaagtgctg aagcacggtg ctgacgttaa cgctcaggac aaattcggta   780
agaccgcttt cgacatctcc atcgacaacg gtaacgagga cctggctgaa atcctgcaag   840
cggccgcaca tcatcatcac catcacgggg ccgcagaaca aaaactcatc tcagaagagg   900
atctgaatgn nncgcntag                                              919

SEQ ID NO: 54          moltype = AA   length = 177
FEATURE                Location/Qualifiers
source                 1..177
                       mol_type = protein
                       organism = synthetic construct
```

-continued

```
SEQUENCE: 54
MLPARMLCGI VSGQFHTGNS YDHDYAKLAC KFYFKETVIA SMKKIWLALA GLVLAFSASA  60
DYKEAQPAMD LGKKLLEAAR AGQDDEVRIL MANGADVNAL DEVGSTPLHL AAMAGHLEIV  120
EVLKHGADVN AQDKFGKTAF DISIDNGNED LAEILQAAAH HHHHHGAAEQ KLISEED      177

SEQ ID NO: 55          moltype = DNA  length = 934
FEATURE                Location/Qualifiers
variation              8
                       note = a, c, t, g, unknown or other
variation              34
                       note = a, c, t, g, unknown or other
variation              37..38
                       note = a, c, t, g, unknown or other
variation              58..59
                       note = a, c, t, g, unknown or other
variation              97
                       note = a, c, t, g, unknown or other
variation              923..927
                       note = a, c, t, g, unknown or other
variation              931
                       note = a, c, t, g, unknown or other
source                 1..934
                       mol_type = other DNA
                       organism = synthetic construct
SEQUENCE: 55
ggacaggnta tccggtaaag cggcagggtc ggancannag agcgcacgag ggagcttnnc  60
agggggaaac gcctggtatc tttatagtcc tgtcggnttt cgcccacctc tgacttgagc  120
gtcgattttt gtgatgctcg tcagggggg cggagcctat ggaaaaacgc cagcaacgcg  180
gccttttac ggttcctggc cttttgctgg ccttttgctc acatgttctt tcctgcgtta  240
tcccctgatt ctgtggataa ccgtattacc gcctttgagt gagctgatac cgctcgccgc  300
agccgaacga ccgagcgcag cgagtcagtg agcgaggaag cggaagagcg cccaatacgc  360
aaaccgcctc tccccgcgcg ttggccgatt cattaatgca gctggcacga caggtttccc  420
gactggaaag cgggcagtga gcgcaacgca attaatgtga gttagctcac tcattaggca  480
ccccaggctt tacactttat gctcccggct cgtatgttgt gtggaattgt gagcggataa  540
caatttcaca caggaaacag ctatgaccat gattacgcca agcttgcatg caaattctat  600
ttcaaggaga cagtcatagc tagcatgaaa aagatttggc tggcgctggc tggtttagtt  660
ttagcgttta gcgcatcggc ggactacaaa gaggcccagc cggccatgga cctggctgct  720
catgttggtc acctggaaat cgttgaagtt ctgctgaagt acggtgctga cgttaacgct  780
caggacaaat tcggtaagac cgctttcgac atctccatcg acaacggtaa cgaggacctg  840
gctgaaatcc tgcaagcggc cgcacatcat catcaccatc acgggccgc agaacaaaaa  900
ctcatctcag aagaggatct gannnnncgc ntag                             934

SEQ ID NO: 56          moltype = AA  length = 228
FEATURE                Location/Qualifiers
source                 1..228
                       mol_type = protein
                       organism = synthetic construct
SEQUENCE: 56
MFFPALSPDS VDNRITAFEA DTARRSRTTE RSESVSEEAE ERPIRKPPLP ARWPIHCSWH  60
DRFPDWKAGS ERNAINVSLT HAPQALHFML PARMLCGIVS GQFHTGNSYD HDYAKLACKF  120
YFKETVIASM KKIWLALAGL VLAFSASADY KEAQPAMDLA AHVGHLEIVE VLLKYGADVN  180
AQDKFGKTAF DISIDNGNED LAEILQAAAH HHHHHGAAEQ KLISEEDL               228

SEQ ID NO: 57          moltype = AA  length = 201
FEATURE                Location/Qualifiers
VARIANT                1..100
                       note = This region may encompass 3-100 residues
VARIANT                102..201
                       note = This region may encompass 3-100 residues
source                 1..201
                       mol_type = protein
                       organism = synthetic construct
SEQUENCE: 57
GGGGGGGGGG GGGGGGGGGG GGGGGGGGGG GGGGGGGGGG GGGGGGGGGG GGGGGGGGGG  60
GGGGGGGGGG GGGGGGGGGG GGGGGGGGGG GGGGGGGGGG PGGGGGGGGG GGGGGGGGGG  120
GGGGGGGGGG GGGGGGGGGG GGGGGGGGGG GGGGGGGGGG GGGGGGGGGG GGGGGGGGGG  180
GGGGGGGGGG GGGGGGGGGG G                                            201
```

BINDING MOLECULE BINDING TO TRAUMATIC BRAIN INJURY-ASSOCIATED TAU AND METHODS OF USE THEREOF

CROSS-REFERENCE TO RELATED APPLICATIONS

This application is a continuation of U.S. application Ser. No. 16/712,652 filed on Dec. 12, 2019, which is a continuation application of U.S. application Ser. No. 16/400,894 filed May 1, 2019, which is a continuation application of U.S. application Ser. No. 16/060,880, filed on Jun. 8, 2018, which is a 35 U.S.C. § 371 application of International Application No. PCT/US2016/065908, filed on Dec. 9, 2016, which claims the benefit of U.S. Provisional Application Ser. No. 62/266,461, filed on Dec. 11, 2015. The entire content of the applications referenced above are hereby incorporated by reference herein.

STATEMENT REGARDING FEDERALLY SPONSORED RESEARCH

This invention was made with government support under W81XWH-14-1-0467 awarded by the Department of Defense and R21 AG041472 awarded by the National Institutes of Health. The government has certain rights in the invention.

SEQUENCE LISTING

The instant application contains a Sequence Listing which has been filed electronically in Xml format and is hereby incorporated by reference in its entirety. Said Xml copy, created on Jan. 4, 2023, is named G8118-02905_SL.xml and is 248,746 bytes in size.

BACKGROUND

Numerous studies have implicated small soluble oligomeric aggregates of Aβ as toxic species in Alzheimer's disease (AD), and increasing evidence also implicates oligomeric forms of tau as having a direct role in disease pathogenesis of AD and other tauopathies such as Frontotemporal Dementia (FTD). As the focus of Aβ studies has slowly shifted toward soluble Aβ species and mechanisms, new reagents were needed that could specifically identify the variety of different aggregate species present. Indeed, many contradictory studies on the role of Aβ aggregation in AD were reported and progress impeded because suitably selective reagents were not available to characterize the aggregate species present. Increasing evidence from cell and animal models indicate that oligomeric rather than fibrillar forms of tau are toxic and correlate with neuronal degeneration, therefore well characterized reagents that can specifically recognize the diversity of tau morphologies present in the human brain are critically needed to facilitate studies to identify the most promising tau species for use as biomarkers of disease and to study toxic mechanisms.

The microtubule associating protein tau is a major component of the neurofibrillary tangles associated with AD and tauopathies that are characterized by hyperphosphorylation and aggregation of tau. Tau plays an important role in assembly and stabilization of microtubules. Tau is a natively unfolded protein, and similar to a number of other natively unfolded proteins, it can aberrantly fold into various aggregate morphologies including β-sheet rich fibrillar forms. The different types of post-translational modifications of tau in AD include phosphorylation, glycosylation, glycation, prolyl-isomerization, cleavage or truncation, nitration, polyamination, ubiquitination, sumoylation, oxidation and aggregation. Tau has 85 putative phosphorylation sites, and excess phosphorylation can interfere with microtubule assembly. Tau can be modified by phosphorylation or by reactive nitrogen and oxygen species among others. Elevated total tau concentration in CSF has been correlated with AD, as has the presence of various phosphorylated tau forms, and the ratio of tau to Aβ42. Reactive nitrogen and oxygen can modify tau facilitating formation of aggregate forms including oligomeric species. Levels of oligomeric tau have also been implicated as a potential early diagnostic for AD. Therefore, while determination of total tau and phosphorylated tau levels has demonstrated value for diagnosis of AD and other tauopathies, reagents that can selectively recognize the tau species that are most selectively involved in AD would have particular value in diagnostics for neurodegenerative diseases including tauopathies and AD.

Tau is an intrinsically unstructured protein due to its very low hydrophobic content containing a projection domain, a basic proline-rich region, and an assembly domain. Hexapeptide motifs in repeat regions of tau give the protein a propensity to form β-sheet structures which facilitate interaction with tubulin to form microtubules as well as self-interaction to form pathological aggregates such as paired helical filaments (PHF). Hyperphosphorylation of tau, particularly in the assembly domain, decreases the affinity of tau to the microtubules and impairs its ability to regulate microtubule dynamics and axonal transport. In addition, parts of the basic proline-rich domain and the pseudo-repeat also stabilize microtubules by interacting with its negatively charged surface. Alternative splicing of the second, third and tenth exons of tau results in six tau isoforms of varying length in the CNS. The assembly domain in the carboxyl-terminal portion of the protein contains either three or four repeats (3R or 4R) of a conserved tubulin-binding motif depending on alternative splicing of exon 10. Tau 4R isoforms have greater microtubule binding and stabilizing ability than the 3R isoforms. Human adult brains have similar levels of 3R and 4R isoforms, while only 3R tau is expressed at the fetal stage. Mutations altering splicing of tau transcript and the ratio of 3R to 4R tau isoforms are sufficient to cause neurodegenerative disease. Therefore tau in human brain tissue can exist in a variety of different lengths and morphologies and with multiple post-translational modifications.

Tau plays a critical role in the pathogenesis of AD and studies show that reduction of tau levels in AD animal models reverses disease phenotypes and that tau is necessary for the development of cognitive deficits in AD models caused by over-expression of AD. While NFTs have been implicated in mediating neurodegeneration in AD and tauopathies, animal models of tauopathy have shown that memory impairment and neuron loss do not associate well with accumulation of NFT. Animal studies showed improvement in memory and reduction in neuron loss despite the accumulation of NFTs, a regional dissociation of neuron loss and NFT pathology, and hippocampal synapse loss and dysfunction and microglial activation months before the accumulation of filamentous tau inclusions. The pathological structures of tau most closely associated with AD progression are tau oligomers. All these studies suggest that tau tangles are not acutely neurotoxic, but rather that pretangle oligomeric tau species are responsible for the neurodegenerative phenotype, similar to toxic role of oligomeric Aβ species.

Numerous studies suggest that extracellular tau species contribute to neurotoxicity through an "infectious" model of disease progression. For example, tau pathology spreads contiguously throughout the brain from early to late stage disease, extracellular tau aggregates can propagate tau mis- folding from the outside to the inside of a cell, brain extract from a transgenic mouse with aggregated mutant human tau transmits tau pathology throughout the brain in mice expressing normal human tau, induction of pro-aggregation human tau induces formation of tau aggregates and tangles composed of both human and normal murine tau (co- aggregation), and levels of tau rise in CSF in AD, whereas Aβ levels decrease. A receptor-mediated mechanism for the spread of tau pathology by extracellular tau has been described.

Collectively, these studies all indicate that a variety of different tau forms including splice variants, post-transla- tional modifications and different aggregated forms, both intracellular and extracellular, are vitally important in AD and other tauopathies. In order to more clearly define the role of individual tau forms in disease, there is a critical need to develop a series of well-defined reagents that selectively recognize individual tau species, and to use these reagents to identify which tau forms are the best biomarkers for AD, which forms are involved in toxicity, and which forms can distinguish between healthy and AD patients in brain tissue and CSF samples.

SUMMARY

Methods have been developed that enable generation of reagents that selectively bind disease related protein vari- ants. The inventors have developed methods and reagents to assess neuronal damage following traumatic brain injury (TBI). The inventors have also developed methods and reagents to assess the staging of Alzheimer's Disease (AD). Phage display antibody libraries are used as a source to isolate the protein variant specific reagents.

The present invention discloses an antibody or antibody fragment that preferentially recognizes human traumatic brain injury (TBI)-associated tau and other antibody or antibody fragments that preferentially recognize different stages of AD. As used herein, the phrase "preferentially recognizes" indicates that it does not bind to or recognize non-TBI associated forms of tau or non-specific proteins. As used herein, the term "antibody" includes scFv (also called a "nanobody"), humanized, fully human or chimeric anti- bodies, single-chain antibodies, diabodies, and antigen- binding fragments of antibodies (e.g., Fab fragments).

In certain embodiments, the antibody is an antibody fragment that does not contain the constant domain region of an antibody.

In certain embodiments, the antibody fragment is less than 500 amino acids in length, such as between 200-450 amino acids in length, or less than 400 amino acids in length.

In certain embodiments, the antibody has an amino acid sequence having at least 80% sequence identity of any one of SEQ ID NO: 42, 44, 46, or 48. In certain embodiments, the amino acid sequence has at least 90% sequence identity of any one of SEQ ID NO: 42, 44, 46, or 48. In certain embodiments, the amino acid sequence has at least 95% sequence identity of any one of SEQ ID NO: 42, 44, 46, or 48. In certain embodiments, the amino acid sequence has 100% sequence identity of any one of SEQ ID NO: 42, 44, 46, or 48. In certain embodiments, the present invention discloses a nucleic acid that encodes an antibody that preferentially recognizes human traumatic brain injury (TBI)-associated tau. In certain embodiments, the present invention provides a nucleic acid encoding an antibody that preferentially recognizes TBI-associated tau, wherein the nucleic acid has at least 80% sequence identity of any one of SEQ ID NO: 41, 43, 45, or 47. In certain embodiments, the nucleic acid sequence has at least 90% sequence identity of any one of SEQ ID NO: 41, 43, 45, or 47. In certain embodiments, the nucleic acid sequence has at least 95% sequence identity of any one of SEQ ID NO: 41, 43, 45, or 47. In certain embodiments, the nucleic acid sequence has 100% sequence identity of any one of SEQ ID NO: 41, 43, 45, or 47.

In certain embodiments, the present invention provides an antibody that preferentially recognizes a human Alzheimer's Disease (AD)-associated Tau.

In certain embodiments, the antibody is an antibody fragment that does not contain the constant domain region of an antibody.

In certain embodiments, the antibody fragment is less than 500 amino acids in length, such as between 200-450 amino acids in length, or less than 400 amino acids in length. In certain embodiments, the antibody has an amino acid sequence having at least 80% sequence identity of any one of SEQ ID NO: 2, 4, 6, 8, 10, 12, 14, 16, 18, 20, 22, 24, 26, 28, 30, 32, 34, 36, 38, or 40. In certain embodiments, the amino acid sequence has at least 90% sequence identity of any one of SEQ ID NO: 2, 4, 6, 8, 10, 12, 14, 16, 18, 20, 22, 24, 26, 28, 30, 32, 34, 36, 38, or 40. In certain embodiments, the amino acid sequence has at least 95% sequence identity of any one of SEQ ID NO: 2, 4, 6, 8, 10, 12, 14, 16, 18, 20, 22, 24, 26, 28, 30, 32, 34, 36, 38, or 40. In certain embodiments, the amino acid sequence has 100% sequence identity of any one of SEQ ID NO: 2, 4, 6, 8, 10, 12, 14, 16, 18, 20, 22, 24, 26, 28, 30, 32, 34, 36, 38, or 40.

In certain embodiments, the present invention discloses a nucleic acid that encodes an antibody that preferentially recognizes human AD-associated tau. In certain embodi- ments, the present invention provides a nucleic acid encod- ing an antibody that preferentially recognizes a human AD-associated tau, wherein the nucleic acid has at least 80% sequence identity of any one of SEQ ID NO: 1, 3, 5, 7, 9, 11, 13, 15, 17, 19, 21, 23, 25, 27, 29, 31, 33, 35, 37, or 39. In certain embodiments, the nucleic acid has at least 90% sequence identity of any one of SEQ ID NO: 1, 3, 5, 7, 9, 11, 13, 15, 17, 19, 21, 23, 25, 27, 29, 31, 33, 35, 37, or 39. In certain embodiments, the nucleic acid has at least 95% sequence identity of any one of SEQ ID NO: 1, 3, 5, 7, 9, 11, 13, 15, 17, 19, 21, 23, 25, 27, 29, 31, 33, 35, 37, or 39. In certain embodiments, the nucleic acid has 100% sequence identity of any one of SEQ ID NO: 1, 3, 5, 7, 9, 11, 13, 15, 17, 19, 21, 23, 25, 27, 29, 31, 33, 35, 37, or 39.

In certain embodiments, the present invention provides a vector comprising a nucleic acid described above.

In certain embodiments, the present invention provides a phage comprising the vector described above.

In certain embodiments, the present invention provides a method for determining risk of traumatic brain injury (TBI), assessment of the amount of neuronal damage, and/or sus- ceptibility to neurodegenerative disease in a human, com- prising the steps of:

(A) providing a sample obtained from a subject post- injury;

(B) detecting levels of human TBI-associated tau in the sample;

(C) comparing the TBI-associated tau protein level in the sample with TBI-associated tau protein level in a normal control; and (D) determining whether the human has a risk of TBI in accordance with the result of step (C);

wherein a subject having elevated TBI-associated tau protein has a high risk of TBI.

In certain embodiments, the present invention provides a method for determining the stage of Alzheimer's disease (AD) in a human, comprising the steps of:

(A) providing a sample obtained from a human;

(B) detecting levels of stage-specific human AD-associated tau in the sample;

(C) comparing the AD-associated tau protein level in the sample with AD-associated tau protein level in a normal control; and (D) determining whether the subject has a risk of AD in accordance with the result of step (C);

wherein a subject having elevated AD-associated tau protein has a high risk of AD.

In certain embodiments, the samples and the normal control are blood product samples or cerebrospinal fluid (CSF) samples.

In certain embodiments, the blood product is serum.

In certain embodiments, the detecting in step (B) is by means of a ligand specific for the protein.

In certain embodiments, the ligand is an antibody.

In certain embodiments, the ligand is a scFv.

In certain embodiments, the protein levels are detected by means of ELISA.

BRIEF DESCRIPTION OF THE FIGURES

FIG. 3a: Western blot of human AD and control brain tissue homogenates. Staining with polyclonal tau antibody shows presence of increased molecular weight tau species in AD patient sample compared to ND sample. Staining with the anti-phosphorylated tau antibody, AT8 shows presence of high molecular weight phosphorylated tau species in the AD sample with no phosphorylated tau species in the ND sample. FIG. 3b: Western blot of human AD and control brain tissue homogenates after immunoprecipitation with polyclonal anti-tau antibody. Staining with anti-phosphorylated tau antibody AT8, shows presence of high molecular weight phosphorylated tau species in AD sample with its absence in the ND sample.

DETAILED DESCRIPTION

Figure 1:
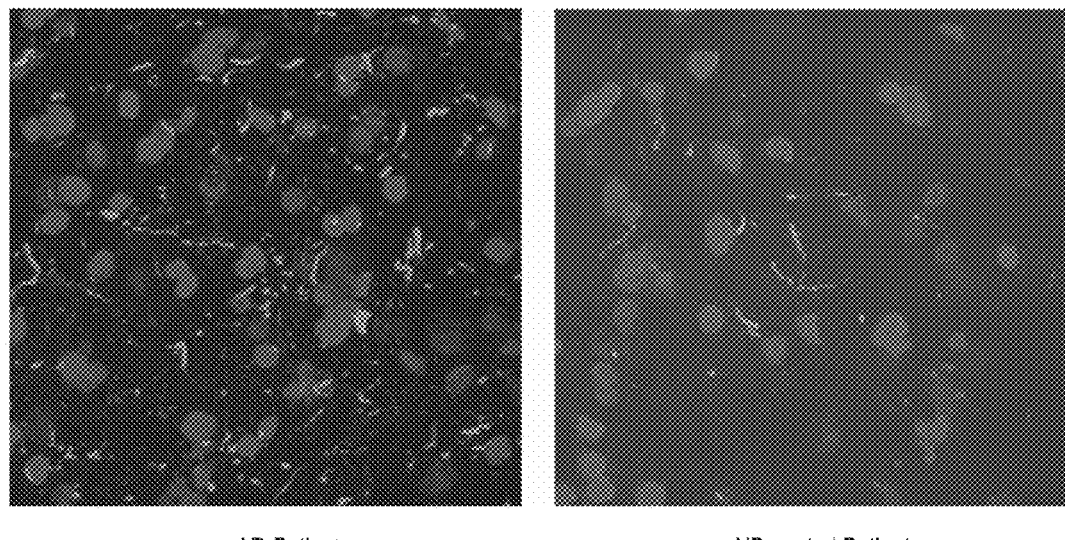
FIG. 1: Immunohistochemistry stain of human AD and control brain tissue slices showing increased presence of phosphorylated tau fibrils in the human AD tissue compared to the age matched cognitively normal sample. Tau was stained using the commercially available anti-phospho-tau antibody AT8.

A vast number of studies have correlated protein aggregation with neurodegenerative diseases including AD, Parkinson's and Dementia with Lewy Bodies. Numerous recent studies suggest that specific protein variants including selected oligomeric forms of these proteins are involved in neuronal toxicity and can interfere with important functions including long term potentiation. Various soluble oligomeric species of Aβ and a-syn have been shown to occur early during the course of AD and PD, and increasing evidence implicates oligomeric forms of tau in AD and other tauopathies.

A novel biopanning technology has been developed that combines the imaging capability of Atomic Force Microscopy (AFM) with the diversity of antibody libraries. This unique combination of antibody diversity and imaging capability allows for the isolation of single chain antibody variable domain fragment (scFv or nanobody) reagents to an array of morphologies of key proteins involved in neurodegenerative diseases including Aβ and alpha-synuclein (a-syn). Nanobodies have been isolated that specifically recognize monomeric, fibrillar, and two different oligomeric a-syn morphologies. The anti-oligomeric a-syn nanobodies do not cross react with oligomeric AD, and specifically label PD brain tissue but not AD or healthy tissue. In addition, nanobodies were isolated to different regions of full length Aβ and to three distinct naturally occurring oligomeric Aβ morphologies. One, A4, specifically recognizes a larger oligomeric Aβ species, inhibits aggregation and extracellular toxicity of AD, does not cross react with oligomeric a-syn, and specifically labels Aβ aggregates in human AD brain samples, but not PD or healthy brain tissue. A second nanobody, E1, recognizes a smaller trimeric or tetrameric Aβ species, and similar to A4 inhibits aggregation and extracellular toxicity of Aβ, does not cross react with oligomeric a-syn, and labels Aβ aggregates in human AD but not healthy brain tissue. Utilizing an AD brain derived oligomeric Aβ preparation, a third nanobody, C6, was isolated that specifically recognizes oligomeric Aβ species derived from human AD brain tissue, but does not recognize Aβ aggregates generated in vitro. The different specificities of each nanobody can be readily observed when each nanobody is expressed on the surface of a filamentous bacteriophage and antibody/antigen complexes are imaged by AFM. Therefore, the combination of antibody libraries and AFM imaging technologies enables the isolation and characterization of reagents that recognize specific protein variants including a variety of different naturally occurring aggregated forms of both a-syn and Aβ.

Another powerful advantage of this AFM panning protocol is that not only is it possible to isolate and characterize reagents to specific protein morphologies, but it is possible to do so using only picograms or less of material. In addition the sample does not need to be purified, and the protein does not need to be chemically modified in any way. It is possible to actually isolate nanobodies against a single molecule of the target antigen. This unique ability to generate and characterize reagents that specifically recognize individual protein variants provides the means to generate reagents that selectively recognize an array of different tau variants present in human AD brain.

While several reagents already exist that can recognize monomeric and phosphorylated tau, these reagents cannot distinguish between different aggregated states of tau. Reagents that can detect specific forms of tau can provide very powerful tools to facilitate diagnosis of AD and other tauopathies and to follow progression of these diseases or to evaluate therapeutic strategies. While many neurodegenerative diseases have overlapping clinical symptoms and cellular and biochemical mechanisms such as an increase in inflammatory markers, and aggregation of similar proteins, the reagents presently developed have well defined specificities and selectivities for selected tau forms and facilitate specific diagnoses of AD and other tauopathies. In combination with other protein and morphology specific reagents against Aβ and a-syn species, these reagents can be used to detect the presence of biomarkers which can readily detect and distinguish many related neurodegenerative diseases including AD, PD, FTD and LBD.

In addition to the unique reagents and ELISA protocol, other advantages of this proposal over previous studies include the use of postmortem tissue and CSF from cases with neuropathologically confirmed AD; the use of control subjects who have had standardized neuromotor assessment and postmortem neuropathologic examination, ensuring that they are not in preclinical stages of AD or other neurodegenerative disease, and the use of a significant number of cases, compensating for individual variation as well as allowing stratification for possible significant influences on disease severity.

Traumatic Brain Injury

It is well established that chronic stress and especially traumatic brain injury (TBI) can disrupt cognitive functioning. The brain is very sensitive to stress and injury and responds by expressing a variety of neuromorphological and neurochemical changes. Stress induces increases in expression levels in the hippocampus of the Amyloid Precursor Protein (APP) and BACE-1, a protease which cleaves APP. These increases are of particular relevance for soldiers suffering TBI since similar increases in hippocampal expression of APP and BACE-1 are strongly linked with the onset and progression of Alzheimer's disease (AD). BACE-1 cleavage of APP results in generation of the beta-amyloid (Aβ) protein, the primary component of the hallmark amyloid plaques associated with AD. Numerous studies have indicated that patients suffering brain trauma are at greater risk of developing AD and at an earlier age. The brain experiences very high sheer forces and mechanical deformation following TBI, and neuronal axons, particularly in the white matter are very susceptible to injury. Resulting damage to the neuronal axons can impair protein transport leading to accumulation of proteins and swelling causing the typical axon pathology observed with TBI. Various forms of stress induce memory deficits in mice and rats, with accompanying increases in APP, BACE-1 and Aβ levels.

Increased expression of APP and BACE-1 results in increased production of Aβ, which in turn can promote aggregation of this natively unstructured protein into a variety of soluble aggregate species some of which are potent neurotoxins that inhibit long term potentiation and other neuronal functions. Aβ can also self-assemble into much larger aggregates which eventually form the distinctive insoluble amyloid fibrils which are a hallmark of AD brain tissue. A vast amount of literature implicates Aβ accumulation as being central to the progression of AD, leading to formation of the Aβ hypothesis. The major weakness of the Aβ hypothesis however, is that the presence of amyloid plaques does not correlate well with the progression of AD. While Aβ can form amyloid plaques, it also forms a number of soluble intermediate or metastable structures which may contribute to toxicity. Cortical levels of soluble Aβ correlated well with the cognitive impairment and loss of synaptic function. Small, soluble aggregates of Aβ termed Aβ-derived diffusible ligands and spherical or annular aggregates termed protofibrils are neurotoxic. Oligomeric forms of Aβ, created in vitro or derived from cell cultures inhibit long term potentiation. The concentration of oligomeric forms of Aβ is also elevated in transgenic mouse models of AD and in human AD brain and CSF samples. Disruption of neural connections near Aβ plaques was also attributed to oligomeric Aβ species. A halo of oligomeric Aβ surrounds Aβ plaques causing synapse loss, and oligomeric Aβ was shown to disrupt cognitive function in transgenic animal models of AD. Different size oligomers of Aβ have been correlated with AD, including a 56 kD aggregate and smaller trimeric and tetrameric species. Therefore, the presence of oligomeric Aβ is strongly correlated with neuronal dysfunction and memory deficits following neuronal damage and plays a critical role in progression of AD.

Given the critical role of APP and BACE-1 in cognitive deficits associated with AD, it is likely that similar increases in APP and BACE-1 levels induced by stress and injury to the brain also lead to elevated Aβ levels, promoting formation of neurotoxic aggregate species, and subsequent memory loss and neuronal dysfunction. Following induced trauma to the brain, substantial deposition of non-fibrillar Aβ aggregates has been observed throughout the brain, even after only a single event. Significantly, when TBI is induced in animal models of AD, there is a substantial increase in neuronal death, memory disorders, and Aβ accumulation, but no corresponding increase in Aβ plaque deposition, there was even a decrease in observed plaques. A preponderance of studies now indicate that various soluble oligomeric Aβ aggregates play a very critical role in neuronal dysfunction rather than the hallmark fibrillar Aβ plaques that have long been associated with AD. An observed increase in Aβ levels in CSF samples from TBI patients suggests that detection of specific Aβ species in CSF and serum represents a promising route for early detection of AD like brain injury in soldiers suffering TBI.

Since TBI also induces axonal injury and damage to protein transport mechanisms, neurofilament proteins may also play a role in TBI and AD. Neurofilament proteins accumulate in axons following TBI, and several studies have implicated the neurofilament protein tau in this process. The second major pathological feature of AD brains is the presence of neurofibrillary tangles that contain aggregates of the microtubule associated protein, tau. Tau is also a natively unfolded protein similar to AD, and can aberrantly fold into various aggregate morphologies including β-sheet containing fibrillar forms and different oligomeric species. Tau plays an important role in assembly and stabilization of microtubules and can undergo numerous post-translational modifications including phosphorylation, glycosylation, glycation, prolyl-isomerization, cleavage or truncation, nitration, polyamination, ubiquitination, sumoylation, oxidation and aggregation. Tau has 85 putative phosphorylation sites, and excess phosphorylation can interfere with microtubule assembly. Elevated total tau concentration in CSF has been correlated with AD, as has the presence of various phosphorylated tau forms and the ratio of tau to Aβ42. In addition to phosphorylation, tau can be modified by reactive nitrogen and oxygen species, leading to modified tau forms that are prone to assemble into aggregate species including different oligomeric forms. Levels of oligomeric tau have also been implicated as a potential early diagnostic for AD. Therefore, determination of total tau, phosphorylated tau and oligomeric tau concentrations all have potential value as diagnostics for neurodegenerative disorders including tauopathies, AD and TBI.

Tau is a very complex protein in vivo as alternative splicing of the second, third and tenth exons of tau result in generation of six tau isoforms of varying length in the CNS. The assembly domain in the carboxyl-terminal portion of the protein contains either three or four repeats (3R or 4R) of a conserved tubulin-binding motif depending on alternative splicing of exon 10. Tau 4R isoforms have greater microtubule binding and stabilizing ability than the 3R isoforms. Human adult brains have similar levels of 3R and 4R isoforms, whereas only 3R tau is expressed at the fetal stage. In tauopathies, mutations altering the splicing of tau transcript and the ratio of 3R to 4R tau isoforms are sufficient to cause neurodegenerative disease. Therefore tau in human brain tissue can exist in a variety of different lengths and morphologies and with multiple post-translational modifications.

Tau plays a critical role in the pathogenesis of AD and studies show that reduction of tau levels in AD animal models reverses disease phenotypes and that tau is necessary for the development of cognitive deficits in AD models caused by over-expression of Aβ. While NFTs have been implicated in mediating neurodegeneration in AD and tauopathies, animal models of tauopathy have shown that memory impairment and neuron loss do not associate well with accumulation of NFT. In animal models expressing human tau, neurodegeneration-related phenotypes including behavioral impairments, neuronal loss, and synapse lesions correlate better with the presence of soluble tau oligomers and pre-filament species than with fibrillar NFT levels. Neuronal loss also precedes NFT formation suggesting involvement of other species such as oligomeric tau variants. In addition, animal studies showed that hippocampal synapse loss and dysfunction and microglial activation occurred months before the accumulation of filamentous tau inclusions. Both brain derived and recombinant oligomeric tau aggregate species disrupt intracellular calcium levels and are toxic to cultured human neuronal cells when added extracellularly. The pathological structures of tau most closely associated with AD progression were shown to be tau oligomers. In postmortem human brains, high oligomeric tau levels were detected in the frontal lobe cortex at early stages of AD before the presence of NFTs. Oligomeric tau may also be responsible for transmission of pathology with a prion-like mechanism as NFT tau pathology spreads from brain regions seeded with oligomeric tau into other regions resulting in aggregation of endogenous tau. It has been previously shown using recombinant human tau (rhTau) that extracellular trimeric, but not monomeric or dimeric species are toxic to human neuronal cells.

All these studies suggest that tau tangles are not acutely neurotoxic, but rather that pretangle oligomeric tau species are responsible for the neurodegenerative phenotype, similar to toxic role of oligomeric Aβ species. Therefore both toxic oligomeric Aβ and tau species in CSF and serum have promise as early biomarkers for AD and for AD like damage in TBI patients.

Similar to the role of Aβ and tau in AD, aggregation of alpha-synuclein (a-syn) plays a critical role in PD and synucleinopathies. A-syn is a major component of Lewy bodies and neurites. Wild-type a-syn along with the three mutant forms, A30P, E46K and A53T can assemble into Lewy body like fibrils in vitro. Since all of the mutations increase the total rate of oligomerization compared to the wild-type form of a-syn, it has been postulated that the intermediate oligomeric morphologies of a-syn are the toxic structures in PD rather than fibrils. A partially folded intermediate of a-syn helps to promote fibril formation in vitro and a protofibrillar form of a-syn is stabilized by formation of a dopamine adduct complex, suggesting a possible connection between this morphology of a-syn and dopaminergic cell death. The different morphologies of a-syn also have different affinities for various membranes, and both the oligomeric forms and fibrillar forms have been shown to disrupt membrane permeability and integrity. Aggregated forms of a-syn were shown to induce toxicity in dopaminergic neurons in vivo and several different oligomeric morphologies were shown to each have different toxic mechanisms and effects on cells. We have shown that oligomeric but not fibrillar forms of a-syn are toxic to neuronal cells. Toxic oligomeric a-syn forms were identified in living cells, in human plasma from PD patients, and in human PD brain tissue indicating that oligomeric a-syn is also a good biomarker for neuronal damage.

Clearly protein misfolding and aggregation is critically important in many devastating neurodegenerative diseases. Therefore, determining how concentration profiles of selected key forms and morphologies of Aβ, tau and a-syn vary in AD, TBI and cognitively normal patients will facilitate development of an effective diagnostic assay for these diseases. In order to assess the value of these protein aggregates as biomarkers in neuronal disease, highly specific reagents are needed that can selectively identify the different toxic protein species. Our lab has developed unique technology that enables us to isolate reagents that bind specific morphologies of a target protein. We have combined the imaging capabilities of AFM with the binding diversity of phage display antibody technology to allow us to identify the presence of specific protein morphologies and then isolate reagents that bind a target morphology. These morphology specific reagents have promise for assessing whether the specific toxic aggregate species in human samples such as serum, plasma or CSF are useful biomarkers for neuronal damage. CSF levels of Aβ and tau have been useful to predict AD, however biomarker studies of TBI patients have been less successful, where S100B has been the only marker to consistently predict TBI and outcome. S100B is a calcium binding protein that has been implicated in various diseases including AD, diabetes, melanoma and epilepsy, so its use in predicting TBI may be limited. We have developed a series of morphology specific nanobodies that have great promise for distinguishing between different neurodegenerative diseases. These nanobodies selectively recognize toxic protein aggregate biomarkers that are associated with specific diseases, therefore these nanobodies are recognizing biomarkers that are associated with the onset and progression of specific diseases, rather than recognizing a more generic secondary effect such as inflammatory signals, microglial activation or apoptotic markers. We have shown that three different nanobodies against different oligomeric Aβ species all selectively distinguish between AD and PD or healthy samples in post-mortem human tissue and CSF samples. We have similarly shown that two different nanobodies against different toxic oligomeric a-syn species both selectively distinguish between PD and AD or healthy post-mortem human tissue and CSF samples. When we assayed post-mortem tissue, CSF and serum samples from AD, PD and cognitively normal patients with our anti-oligomeric Aβ, a-syn and tau nanobodies, we can not only readily distinguish AD, PD and normal samples but we can also stage progression of these different diseases. Also in the preliminary data section and of direct relevance to this proposal, we show that we can not only detect the presence of toxic oligomeric morphologies of AD, tau and a-syn in ante-mortem human serum samples, but that there is a very distinct spike in oligomeric Aβ species in serum many years prior to diagnosis of AD, and even several years prior to diagnosis of mild-cognitive impairment (MCI) suggesting that we can presymptomatically diagnose AD by analysis of serum samples many years before symptoms of AD occur. Since early, even presymptomatic diagnosis of AD is critical so that preventative and treatment therapies can begin before extensive neuronal damage has occurred, the studies proposed here have very high potential impact. The morphology specific nanobodies we have developed and other nanobodies that have been developed are powerful tools to characterize human tissue, CSF and serum samples and to distinguish between different neurodegenerative diseases. Since the nanobodies recognize toxic species that should be present at early stages of disease progression, these nanobodies should be useful as early presymptomatic biomarkers for different neurodegenerative diseases, and to identify soldiers who are susceptible to AD following TBI.

The following human AD-associated Tau clone sequences were identified:

```
Clone 32B:
                                    (SEQ ID NO: 1)
GATTACNGCCAAGCTTGCATGCAAATTNTTTCAAGGAG

NCAGTCATAATGAAATACNTATTGCCTNCGNCAGCCGCTG

GATTGTTATTACTCGCGGCCCAGCCGGCCATGGCCGAGGT

GCAGCTGTTGGAGTCTGGGGGAGGCTTGGTACAGCCTGGG

GGGTCCCTGAGACTCTCCTGTGCAGCCTCTGGATTCACCT

TTAGCAGCTATGCCATGAGCTGGGTCCGCCAGGCTCCAGG

GAAGGGGCTGGAGTGGGTCTCATCTATTTCTTCTAATGGT

GATGATACAGCTTACGCAGACTCCGTGAAGGGCCGGTTCA
```

```
CCATCTCCAGAGACAATTCCAAGGACACGCTGTATCTGCA

AATGAACAGCCTGAGAGCCGAGGACACGGCCGTATATTAC

TGTGCGAAAGCTAATAATTCTTTTGACTACTGGGGCCAGG

GAACCCTGGTCACCGTCTCGAGCGGTGGAGGCGGTTCAGG

CGGAGGTGGCAGCGGCGGTGGCGGGTCGACGGACATCCAG

ATGACCCAGTCTCCATCCTCCCTGTCTGCATCTGTAGGAG

ACAGAGTCACCATCACTTGCCGGGCAAGTCAGAGCATTAG

CAGCTATTTAAATTGGTATCAGCAGAAACCAGGGAAAGCC

CCTAAGCTCCTGATCTATAATGCATCCACTTTGCAAAGTG

GGGTCCCATCAAGGTTCAGTGGCAGTGGATCTGGGACAGA

TTTCACTCTCACCATCAGCAGTCTGCAACCTGAAGATTTT

GCAACTTACTACTGTCAACAGGATAGTGCTACTCCTTATA

CGTTCGGCCAAGGGACCAAGGTGGAAATCAAACGGGCGGC

CGCACATCATCATCACCATCACGGGGCCGCAGAACAAAAA

CTCATCTCAGAAGAGGATCTGAATGGGGCCGC

32B AA sequence:
                                    (SEQ ID NO: 2)
MKYXLPXXAAGLLLLAAQPAMAEVQLLESGGGLVQPGGSL

RLSCAASGFTFSSYAMSWVRQAPGKGLEWVSSISSNGDDT

AYADSVKGRFTISRDNSKDTLYLQMNSLRAEDTAVYYCAK

ANNSFDYWGQGTLVTVSSGGGGSGGGGSGGGGSTDIQMTQ

SPSSLSASVGDRVTITCRASQSISSYLNWYQQKPGKAPKL

LIYNASTLQSGVPSRFSGSGSGTDFTLTISSLQPEDFATY

YCQQDSATPYTFGQGTKVEIKRAAAHHHHHHGAAEQKLIS

EEDLNGA

Clone 51A:
                                    (SEQ ID NO: 3)
TATGANCCATGATTACGCCAAGCTNNCATGCAANNTNTATTT

TCAAGGAGACAGTCATAATGAAATACCTATTGCNTACGNC

AGCCGCTNNGATTGTTATTACTCGCGGCCNCAGCCGGCCA

TGGCCGAGGTGCAGCTGTNGGAGTCTGGGGGAGGCTTGGT

ACAGCCTGGGGGGTCCCTGAGACTCTCCTGTGCAGCCTCT

GGATTCACCTTTAGCAGNTATGCCATGAGCTGGGTCCGCC

AGGCTCCAGGGAAGGGGCTGGAGTGGGTCTCATAGATTTA

GCAGTCGGGTCCGGTTACATCTTACGCAGACTCCGTGAAG

GGCCGGTTCACCATCTCCAGAGACAATTCCAAGAACACGC

TGTATCTGCAAATGAACAGCCTGAGAGCCGAGGACACGGC

CGTATATTACTGTGCGAAACGTCAGTTGATGTTTGACTAC

TGGGGCCAGGGAACCCTGGTCACCGTCTCGAGCGGTGGAG

GCGGTTCAGGCGGAGGTGGCAGCGGCGGTGGCGGGTCGAC

GGACATCCAGATGACCCAGTCTCCATCCTCCCTGTCTGCA

TCTGTAGGAGACAGAGTCACCATCACTTGCCGGGCAAGTC
```

-continued

```
AGAGCATTAGCAGCTATTTAAATTGGTATCAGCAGAAACC

AGGGAAAGCCCCTAAGCTCCTGATCTATGCTGCATCCAGT

TTGCAAAGTGGGGTCCCATCAAGGTTCAGTGGCAGTGGAT

CTGGGACAGATTTCACTCTCACCATCAGCAGTCTGCAACC

TGAAGATTTTGCAACTTACTACTGTCAACAGAGTTACAGT

ACCCCTAATACGTTCGGCCAAGGGACCAAGGTGGAAATCA

AACGGGCGGCCGCACATCATCATCACCATCACGGGGCCGC

AGAACAAAAACTCATCTCAGAAGAGGATCTGAATGGGCCG

CATAG
```

51A AA sequence:
(SEQ ID NO: 4)
```
MAEVQLXESGGGLVQPGGSLRLSCAASGFTFSXYAMSWVR

QAPGKGLEWVSIQSGPVTSYADSVKGRFTISRDNSKNTLY

LQMNSLRAEDTAVYYCAKRQLMFDYWGQGTLVTVSSGGGG

SGGGGSGGGGSTDIQMTQSPSSLSASVGDRVTITCRASQS

ISSYLNWYQQKPGKAPKLLIYAASSLQSGVPSRFSGSGSG

TDFTLTISSLQPEDFATYYCQQSYSTPNTFGQGTKVEIKR

AAAHHHHHHGAAEQKLISEEDLNGPH
```

Clone 51F:
(SEQ ID NO: 5)
```
ATTNCGCCAAGCTNNCATGCAAAATTTNTATTTNAANGGA

GACAGTCATAATGAAATACCTATTGCNTACNNNNNNNCGC

TGGATTGTTATTACTCGCGGNNCAGCCGGCCATGGCCGAG

GTGCAGCTGTTGGAGTCTGGGGGAGGCTTGGTACAGCCTG

GGGGGTCCCTGAGACTNTCCTGTGCAGCNTCTGGATTCAC

CTTTAGCAGCTATGCCATGANNTGGGTCCGCCAGGCTCCA

GGGAAGGGGCTGNNNNNNGTNTCATCTATTACGTAGACGG

GTTCGTAGACACAGTACGCAGACTCCGTGAAGGGCAGGTT

CACCATCTCCAGAGACAATTCCAAGAACACGCTGTATCTG

CAAATGAACAGCCTGAGAGCCGAGGACACGGCCGTATATT

ACTGTGCGAAACAGCATGATGATTTTGACTACTGGGGCCA

GGGAACCCTGGTCACCGTCTCGAGCGGTGGAGGCGGTTCA

GGCGGAGGTGGCAGCGGCGGTGGCGGGTCGACGGACATCC

AGATGACCCAGTCTCCATCCTCCCTGTCTGCATCTGTAGG

AGACAGAGTCACCATCACTTGCCGGGCAAGTCAGAGCATT

AGCAGCTATTTAAATTGGTATCAGCAGAAACCAGGGAAAG

CCCCTAAGCTCCTGATCTATACTGCATCCAATTTGCAAAG

TGGGGTCCCATCAAGGTTCAGTGGCAGTGGATCTGGGACA

GATTTCACTCTCACCATCAGCAGTNTGCAACCTGAAGATT

TTGCAACTTANTACTGTCAACAGCTGGATGTGTNTCCTTN

GACGTTCGGNCAANNNACCAAGGTGGAAATCAA
```

-continued

51F AA sequence:
(SEQ ID NO: 6)
```
MAEVQLLESGGGLVQPGGSLRXSCAXSGFTFSSYAMXWVR

QAPGKGLXXXSSITTGSTQYADSVKGRFTISRDNSKNTLY

LQMNSLRAEDTAVYYCAKQHDDFDYWGQGTLVTVSSGGGG

SGGGGSGGGGSTDIQMTQSPSSLSASVGDRVTITCRASQS

ISSYLNWYQQKPGKAPKLLIYTASNLQSGVPSRFSGSGSG

TDFTLTISSXQPEDFATXYCQQLDVXPXTFXQXTKVEI
```

Clone 52H:
(SEQ ID NO: 7)
```
GAGACAGTCATAGCTAGCATGAAAAAGANTTGGCTGGCGC

TGGCTGGTTTAGTTTTagCGTTTAGCGCATCGGCGGACTA

CAAAGAGGCCCAGCCGGCCATGGACCTGGGTAAGAAACTG

CTGGAAGCTGCTCGTGCTGGTCAGGACGACGAAGTTCGTA

TCCTGATGGCTAACGGTGCTGACGTTAACGCTGACGACTA

CGAAGGTTGGACTCCGCTGCACCTGGCTGCTATGGTTGGT

CACCTGGAAATCGTTGAAGTTCTGCTGAAGTACGGTGCTG

ACGTTAACGCTCAGGACAAATTCGGTAAGACCGCTTTCGA

CATCTCCATCGACAACGGTAACGAGGACCTGGCTGAAATC

CTGCAAGCGGCCGCACATCATCATCACCATCACGGGGCCG

CAGAACAAAAACTCATCTCAGAAGAGGATCTGAATGGGGC

CGCATAGACTGTTGAAAGTTGTTTAGCAAAACCTCATACA

GAAAATTCATTTACTAACGTCTGGAAAGACGACAAAACTT

TAGATCGTTACGCTAACTATGAGGGCTGTCTGTGGAATGC

TACAGGCGTTGTGGTTTGTACTGGTGACGAAACTCAGTGT

TACGGTACATGGGTTCCTATTGGGCTTGCTATCCCTGAAA

ATGAGGGTGGTGGCTCTGANGGTGGCGGTTCTGAGGGTGG

CGGTTCTGANGGTGGCGGTACTAAACCTCCTGAGTACGGT

GATACACCTATTCCGGGCTATACTTATATCAACCCTCTCG

ACNGCACTTATCCGCCTGGTACTGAGCAAAACCCCGCTAA

TCCTAATCCCTTCTCTTGAGGAGTCTCAGCCTCTTAATAC

TTTCATGTTTCANAATAATANNTTCCGAAATNNNCNNGGT

GCATTAACTGTTTATACNGGCACTGTTACTCNANNNACTG

ACCCCCGTTTAAAACTTATTACCAGTACACTCCNTGNNAT

CAT
```

52H AA sequence:
(SEQ ID NO: 8)
```
MKKXWLALAGLVLAFSASADYKEAQPAMDLGKKLLEAARA

GQDDEVRILMANGADVNADDYEGWTPLHLAAMVGHLEIVE

VLLKYGADVNAQDKFGKTAFDISIDNGNEDLAEILQAAAH

HHHHHGAAEQKLISEEDLNGAA
```

Clone M32B:
(SEQ ID NO: 9)
```
TTCAGGAGANAGTCNTAATGAAATACCTATTGCCTACGGC

AGCCGCTGGAtTGTTATTACTCGCGGNCCAGCCGGCCATG
```

-continued

```
GCCGAGGTGCAGCTGTTGGAGTCTGGGGGAGGCTTGGTAC

AGCCTGGGGGGTCCCTGAGACTCTCCTGTGCAGCCTCTGG

ATTCACCTTTAGCAGCTATGCCATGAGCTGGGTCCGCCAG

GCTCCAGGGAAGGGGCTGGAGTGGGTCTCAGGTATTTCTA

ATAATGGTAGTAATACAACTTACGCAGACTCCGTGAAGGG

CCGGTTCACCATCTCCAGAGACAATTCCAAGAACACGCTG

TATCTGCAAATGAACAGCCTGAGAGCCGAGGACACGGCCG

TATATTACTGTGCGAAAGCTTCTTATACTTTTGACTACTG

GGGCCAGGGAACCCTGGTCACCGTCTCGAGCGGTGGAGGC

GGTTCAGGCGGAGGTGGCAGCGGCGGTGGCGGGTCGACGG

ACATCCAGATGACCCAGTCTCCATCCTCCCTGTCTGCATC

TGTAGGAGACAGAGTCACCATCACTTGCCGGGCAAGTCAG

AGCATTAGCAGCTATTTAAATTGGTATCAGCAGAAACCAG

GGAAAGCCCCTAAGCTCCTGATCTATAGTGCATCCTCTTT

GCAAAGTGGGGTCCCATCAAGGTTCAGTGGCAGTGGATCT

GGGACAGATTTCACTCTCACCATCAGCAGTCTGCAACCTG

AAGATTTTGCAACTTACTACTGTCAACAGTATTCTGGTTC

TCCTGCTACGTTCGGCCNAGGGACCAAGGTGGAAATCANA

CGGGCGGCCGCACNTCATCATNNCCATCACGGGGCCGCAG

AANNAAAACTCATCTCAGAAGAGGANNTGAATGGGGCCGC

ATAGACTGTT
```

M32B AA sequence:

(SEQ ID NO: 10)
```
MKYLLPTAAAGLLLLAXQPAMAEVQLLESGGGLVQPGGSL

RLSCAASGFTFSSYAMSWVRQAPGKGLEWVSGISNNGSNT

TYADSVKGRFTISRDNSKNTLYLQMNSLRAEDTAVYYCAK

ASYTFDYWGQGTLVTVSSGGGGSGGGGSGGGGSTDIQMTQ

SPSSLSASVGDRVTITCRASQSISSYLNWYQQKPGKAPKL

LIYSASSLQSGVPSRFSGSGSGTDFTLTISSLQPEDFATY

YCQQYSGSPATFGXGTKVEIXRAAAXHHXHHGAAEXKLIS

EEX
```

Clone M32E:

(SEQ ID NO: 11)
```
TTCAGGANANAGTCATAATGAANTACCTATTGCCTACGGC

AGCCGCTGGANTNNTATTACTCGCGGCCCAgCCGGCCATG

GCCCANGTGCAGCTGGTGGAGTCTGGGGGAGGCGTGGTCC

AGCCTGGGAGGTCCCTGAGACTCTCCTGTGCAGNCTCCGG

ATTCACCTTTANCAGCTATGACATGGGCTGGGTCCGCCAG

GCTCCAGGGAAGGGGCTGGAGTGGGTCTCAAGTATTAGTG

GTAGTGGTCCTACCATGAACTACGCANACTCTGTGAAGGG

CCGATTCACCGTCTCCAGAGACAATTCCAAGAACACGCTG

TATCTGCAAATGGACAGCCTGAGAGCCGAGGACACGGCCG
```

-continued
```
TATATTACTGTGCGAAAGGGGGTACGGACTTTGACTACTG

GGGCCAGGGCACCCTGGTCACCGTCTCCTCAGGNGGAGGC

GGTTCANGCGGAGGTGGCTCTGGCGGTGGCGGATCGTCTG

AGCTGACTCAGGACCCTGCTGTGTCTGTGGCCTTGGGACA

GACAGTCANCATCACATGCCAAGGANACAGCCTCNNAACC

TATTATGCAAGCTGGTACCANCANAAGCCAGGACAGGCCC

CTGTACTTGTCATCTATGGNAAAAACAACCGGCCCTCANG

GATCNCAGACCGATTCTCTGGCTCCAGCTCANGAAACACA

GCTTCCTTGACCATCACTGNGGCTCAGGCGGAAGATGAGG

CTGACTATTACTGNAACTCCCGGGACAGCAGTGNNAACCA

TCTNANGAGTGTTCGGCGGAGGGANCNNGCTGACCGNCNT

ANGTGCGGCCGCAGNANCNNNNNCTNCNNNTCAGAANANG

ATCTGAATGGGGCNNCATANACTGTTGNAAANNNGNTTAN

CAA
```

M32E AA sequence:

(SEQ ID NO: 12)
```
MXYLLPTAAAGXXLLAAQPAMAXVQLVESGGGVVQPGRSL

RLSCAXSGFTFXSYDMGWVRQAPGKGLEWVSSISGSGPTM

NYAXSVKGRFTVSRDNSKNTLYLQMDSLRAEDTAVYYCAK

GGTDFDYWGQGTLVTVSSXGGGSXGGGSGGGGSSELTQDP

AVSVALGQTVXITCQGXSLXTYYASWYXXKPGQAPVLVIY

XKNNRPSXIXDRFSGSSSXNTASLTITXAQAEDEADYYXN

SRDSSXNHXXSVRRR
```

Clone M33F:

(SEQ ID NO: 13)
```
TTCAGGAGANAGTCNTAATGAAATACCTATTGCCTACGGC

AGCCGCTGGATTGTTATTACTCGCGGCCCAGCCGGCCATG

GCCGAGGTGCAGCTGTTGGAGTCTGGGGGAGGCTTGGTAC

AGCCTGGGGGGTCCCTGAGACTCTCCTGTGCAGCCTCTGG

ATTCACCTTTAGCAGCTATGCCATGAGCTGGGTCCGCCAG

GCTCCAGGGAAGGGGCTGGAGTGGGTCTCAGCTATTACTA

ATGATGGTGCTGGTACAACTTACGCAGACTCCGTGAAGGG

CCGGTTCACCATCTCCAGAGACAATTCCAAGAACACGCTG

TATCTGCAAATGAACAGCCTGAGAGCCGAGGACACGGCCG

TATATTACTGTGCGAAATCTTATACTGGTTTTGACTACTG

GGGCCAGGGAACCCTGGTCACCGTCTCGAGCGGTGGAGGC

GGTTCAGGCGGAGGTGGCAGCGGCGGTGGCGGGTCGACGG

ACATCCAGATGACCCAATCTCCATCCTCCCTGTCTGCATC

TGTAGGAGACAGAGTCACCATCACTTGCCGGGCAAGTCAG

AGCATTAGCAGCTATTTAAATTGGTATCAGCAGAAACCAG

GGAAAGCCCCTAAGCTCCTGATCTATACTGCATCCACTTT

GCAAAGTGGGGTCCCATTAAGGTTCAGTGGCAGTGGATCT

GGGACAGATTTCACTCTCACCATCAGCAGTCTGCAACCTG
```

-continued

```
AAGATTTTGCAACTTACTACTGTCAACAGANNTATGCTAN

TCCTANNACGTTCGGNCNANGGGACCNNNGNNNNNAAATCA

NNCGGGCGGCCGCACNNCATNATNNNNNATNCNCGNNNNC

GCAGAACAAAACTC
```

M33F AA sequence:

```
                                    (SEQ ID NO: 14)
MKYLLPTAAAGLLLLAAQPAMAEVQLLESGGGLVQPGGSL

RLSCAASGFTFSSYAMSWVRQAPGKGLEWVSAITNDGAGT

TYADSVKGRFTISRDNSKNTLYLQMNSLRAEDTAVYYCAK

SYTGFDYWGQGTLVTVSSGGGGSGGGGSGGGGSTDIQMTQ

SPSSLSASVGDRVTITCRASQSISSYLNWYQQKPGKAPKL

LIYTASTLQSGXPLRFSGSGSGTDFTLTISSLQPEDFATY

YCQQXYAXPXTF
```

Clone M34C:

```
                                    (SEQ ID NO: 15)
CTANGCGNCCNNTTNAGATCCTCTTCTGAGANGAGTTTTT

GTTCTGCGGCCCCGTGATGGTGATGATGATGTGCGGCCGC

CCGTTTGATTTCCACCTTGGTCCCTTGGCCGAACGTCGCA

GGAGTCTGATGAGTCTGTTGACAGTAGTAAGTTGCAAAAT

CTTCAGGTTGCAGACTGCTGATGGTGAGAGTGAAATCTGT

CCCAGATCCACTGCCACTGAACCTTGATGGGACCCCACTT

TGCAACTGGGATGCCGGATAGATCAGGAGCTTAGGGGCTT

TCCCTGGTTTCTGCTGATACCAATTTAAATAGCTGCTAAT

GCTCTGACTTGCCCGGCAAGTGATGGTGACTCTGTCTCCT

ACAGATGCAGACAGGGAGGATGGAGACTGGGTCATCTGGA

TGTCCGTCGACCCGCCACCGCCGCTGCCACCTCCGCCTGA

ACCGCCTCCACCGCTCGAGACGGTGACCAGGGTTCCCTGG

CCCCAGTAGTCAAAAGACCAAAACTGTTTCGCACAGTAAT

ATACGGCCGTGTCCTCGGCTCTCAGGCTGTTCATTTGCAG

ATACAGCGTGTTCTTGGAATTGTCTCTGGAGATGGTGAAC

CGGCCCTTCACGGAGTCTGCGTACGTTGTCGGCGGACCCT

GCTTCGCAATATCTGAGACCCACTCCAGCCCCTTCCCTGG

AGCCTGGCGGACCCAGCTCATGGCATAGCTGCTAAAGGTG

AATCCAGAGGCTGCACAGGAGAGTCTCANGGACCCCCCAG

GCTGTACCAAGCCTCCCCCAGACTCCAACAGCTGCACCTC

GGCCATGGCCGGCTGGGCCGCGAGTAATAACAATCCAGCG

GCTGCCGTANGCAATANGTATTTCATTATGACTGTCTCCT

TGAAATAGAATTTGCATGCAAGCTTGGNNTANNATGGNCA

TAGCTGTTTNCTGTGTGAAATGNTATNCNNTCNCAATTC

CNCACAANATAC
```

-continued

M34C AA sequence:

```
                                    (SEQ ID NO: 16)
MKYXLXTAAAGLLLLAAQPAMAEVQLLESGGGLVQPGGSX

RLSCAASGFTFSSYAMSWVRQAPGKGLEWVSDIAKQGPPT

TYADSVKGRFTISRDNSKNTLYLQMNSLRAEDTAVYYCAK

QFWSFDYWGQGTLVTVSSGGGGSGGGGSGGGGSTDIQMTQ

SPSSLSASVGDRVTITCRASQSISSYLNWYQQKPGKAPKL

LIYPASQLQSGVPSRFSGSGSGTDFTLTISSLQPEDFATY

YCQQTHQTPATFGQGTKVEIKRAAAHHHHHHGAAEQKLXS

EED
```

Clone M34F:

```
                                    (SEQ ID NO: 17)
CATTCNGATCCTCTTCTGAGANGAGTTTTTGTTCTGCGGC

CCCGTGATGGTGATGATGATGTGCGGCCGCCCGTTTGATT

TCCACCTTGGTCCCTTGGCCGAACGTAATAGGAGACGGAT

GCGACTGTTGACAGTAGTAAGTTGCAAAATCTTCAGGTTG

CAGACTGCTGATGGTGAGAGTGAAATCTGTCCCAGATCCA

CTGCCACTGAACCTTGATGGGACCCCACTTTGCAAATTGG

ATGCCCTATAGATCAGGAGCTTAGGGGCTTTCCCTGGTTT

CTGCTGATACCAATTTAAATAGCTGCTAATGCTCTGACTT

GCCCGGCAAGTGATGGTGACTCTGTCTCCTACAGATGCAG

ACAGGGAGGATGGAGACTGGGTCATCTGGATGTCCGTCGA

CCCGCCACCGCCGCTGCCACCTCCGCCTGAACCGCCTCCA

CCGCTCGAGACGGTGACCAGGGTTCCCTGGCCCCAGTAGT

CAAACGCCGTCCAACGTTTCGCACAGTAATATACGGCCGT

GTCCTCGGCTCTCAGGCTGTTCATTTGCAGATACAGCGTG

TTCTTGGAATTGTCTCTGGAGATGGTGAACCGGCCCTTCA

CGGAGTCTGCGTAAATTGTCGGACTACCACCCCCAGCAAT

CGATGAGACCCACTCCAGCCCCTTCCCTGGAGCCTGGCGG

ACCCAGCTCATGGCATAGCTGCTAAAGGTGAATCCAGAGG

CTGCACAGGAGAGTCTCANGGACCCCCCAGGCTGTACCAA

GCCTCCCCCAGACTCCAACAGCTGCACCTCGGCCATGGCC

GGCTGGGCCGCGAGTAATAACAATCCAGCGGCTGCCGTAN

GCAATAGGTATTTCATTATGACTGTCTCCTTGAAATAGAN

TTTGCATGCAAGCTTGGCGTAANTCATGGNCATAGCTGTT

TCCTGTGTGAAATTGTTATCCNCTCACAANTTCCNCNCAA

NCATACGAANCCCGGAANGC
```

M34F AA sequence:

```
                                    (SEQ ID NO: 18)
MXMXYAKLACKXYFKETVIMKYLLXTAAAGLLLLAAQPAM

AEVQLLESGGGLVQPGGSXRLSCAASGFTFSSYAMSWVRQ

APGKGLEWVSSIAGGGSPTIYADSVKGRFTISRDNSKNTL

YLQMNSLRAEDTAVYYCAKRWTAFDYWGQGTLVTVSSGGG

GSGGGGSGGGGSTDIQMTQSPSSLSASVGDRVTITCRASQ
```

-continued

SISSYLNWYQQKPGKAPKLLIYRASNLQSGVPSRFSGSGS

GTDFTLTISSLQPEDFATYYCQQSHPSPITFGQGTKVEIK

RAAAHHHHHGAAEQKLXSEED

Clone M34G:

(SEQ ID NO: 19)

CTATGCGNNNNATTCAGATCCTCTTCTGAGATGAGTTTTT

GTTCTGCGGCCCCGTGATGGTGATGATGATGTGCGGCCGC

CCGTTTGATTTCCACCTTGGTCCCTTGGCCGAACGTAGGA

GGCGAAGTCTGAACCTGTTGACAGTAGTAAGTTGCAAAAT

CTTCAGGTTGCAGACTGCTGATGGTGAGAGTGAAATCTGT

CCCAGATCCACTGCCACTGAACCTTGATGGGACCCCACTT

TGCAACAGGGATGCACGATAGATCAGGAGCTTAGGGGCTT

TCCCTGGTTTCTGCTGATACCAATTTAAATAGCTGCTAAT

GCTCTGGCTTGCCCGGCAAGTGATGGTGACTCTGTCTCCT

ACAGATGCAGACAGGGAGGATGGAGACTGGGTCATCTGGA

TGTCCGTCGACCCGCCACCGCCGCTGCCACCTCCGCCTGA

ACCGCCTCCACCGCTCGAGACGGTGACCAGGGTTCCCTGG

CCCCAGTAGTCAAACTGCTTACCACGTTTCGCACAGTAAT

ATACGGCCGTGTCCTCGGCTCTCAGGCTGTTCATTTGCAG

ATACAGCGTGTTCTTGGAATTGTCTCTGGAGATGGTGAAC

CGGCCCTTCACGGAGTCTGCGTAATGTGTCACAGTACCAT

CCGGCCAAATACCTGAGACCCACTCCAGCCCCTTCCCTGG

AGCCTGGCGGACCCAGCTCATGGCATAGCTGCTAAAGGTG

AATCCAGAGGCTGCACAGGAGAGTCTCAGGGACCCCCCAG

GCTGTACCAAGCCTCCCCCAGACTCCAACAGCTGCACCTC

GGCCATGGCCGGCTGGGCCGCGAGTAATAACAATCCAGCG

GCTGCCGTANGCAATAGGTATTTCATTATGACTGTCTCCT

TGAAATAGAATTTGCATGCAAGCTTGGCGTANTCATGGTC

ATAGCTGTTTCCTGTGNGAAATTGTTATCCGCTCACNNTT

CCACNCAACATACGANCCGG

M34G AA sequence:

(SEQ ID NO: 20)

MKYLLXTAAAGLLLLAAQPAMAEVQLLESGGGLVQPGGSL

RLSCAASGFTFSSYAMSWVRQAPGKGLEWVSGIWPDGTVT

HYADSVKGRFTISRDNSKNTLYLQMNSLRAEDTAVYYCAK

RGKQFDYWGQGTLVTVSSGGGGSGGGGSGGGGSTDIQMTQ

SPSSLSASVGDRVTITCRASQSISSYLNWYQQKPGKAPKL

LIYRASLLQSGVPSRFSGSGSGTDFTLTISSLQPEDFATY

YCQQVQTSPPTFGQGTKVEIKRAAAHHHHHGAAEQKLIS

EEDLNXXHR

-continued

Clone M35A:

(SEQ ID NO: 21)

CTANGCGNNNNNNNTCAGATCCTCTTCTGAGATGAGTTTTT

GTTCTGCGGCCCCGTGATGGTGATGATGATGTGCGGCCGC

CCGTTTGATTTCCACCTTGGTCCCTTGGCCGAACGTAGAA

GGATTATCATCATTCTGTTGACAGTAGTAAGTTGCAAAAT

CTTCAGGTTGCAGACTGCTGATGGTGAGAGTGAAATCTGT

CCCAGATCCACTGCCACTGAACCTTGATGGGACCCCACTT

TGCAAAGTGGATGCATCATAAATCAGGAGCTTAGGGGCTT

TCCCTGGTTTCTGCTGATACCAATTTAAATAGCTGCTAAT

GCTCTGACTTGCCCGGCAAGTGATGGTGACTCTGTCTCCT

ACAGATGCAGACAGGGAGGATGGAGACTGGGTCATCTGGA

TGTCCGTCGACCCGCCACCGCCGCTGCCACCTCCGCCTGA

ACCGCCTCCACCGCTCGAGACGGTGACCAGGGTTCCCTGG

CCCCAGTAGTCAAAACCATTAGAAGTTTTCGCACAGTAAT

ATACGGCCGTGTCCTCGGCTCTCAGGCTGTTCATTTGCAG

ATACAGCGTGTTCTTGGAATTGTCTCTGGAGATGGTGAAC

CGGCCCTTCACGGAGTCTGCGTAATATGTAGTACTACCAG

TAGCATCAATAGTTGAGACCCACTCCAGCCCCTTCCCTGG

AGCCTGGCGGACCCAGCTCATGGCATAGCTGCTAAAGGTG

AATCCAGAGGCTGCACAGGAGAGTCTCAGGGACCCCCCAG

GCTGTACCAAGCCTCCCCCAGACTCCAACAGCTGCACCTC

GGCCATGGCCGGCTGGGCCGCGAGTAATAACAATCCAGCG

GCTGCCGTNNNAATANGTATTTCATTATGACTGTCTCCTT

GAAATAGAATTTGCATGCAAGCTNGGNNTAATCATGGTCA

TAGCTGTTTCCTGTGTGAAATTGTTATCCGCTCACAATTC

CACACAACATACG

M35A AA sequence:

(SEQ ID NO: 22)

MQILFQGDSHNEIXIXTAAAGLLLLLAAQPAMAEVQLLESG

GGLVQPGGSLRLSCAASGFTFSSYAMSWVRQAPGKGLEWV

STIDATGSTTYYADSVKGRFTISRDNSKNTLYLQMNSLRA

EDTAVYYCAKTSNGFDYWGQGTLVTVSSGGGGSGGGGSGG

GGSTDIQMTQSPSSLSASVGDRVTITCRASQSISSYLNWY

QQKPGKAPKLLIYDASTLQSGVPSRFSGSGSGTDFTLTIS

SLQPEDFATYYCQQNDDNPSTFGQGTKVEIKRAAAHHHHH

HGAAEQKLISEEDL

Clone M35F:

(SEQ ID NO: 23)

TTCAGATCCTCTTCTGAGANGAGTTTTTGTTCTGCGGCCC

CGTGATGGTGATGANGATGTGCGGCCGCCCGTTTGATTTC

CACCTTGGTCCCTTGGCCGAACGTAGTAGGACTAGCATAA

CTCTGTTGACAGTAGTAAGTTGCAAAATCTTCAGGTTGCA

GACCGCTGATGGTGAGAGTGAAATCTGTCCCAGATCCACT

-continued

```
GCCACTGAACCTTGATGGGACCCCACTTTGCAAAGAGGAT

GCACCATAGATCAGGAGCTTAGGGGCTTTCCCTGGTTTCT

GCTGATACCAATTTAAATAGCTGCTAATGCTCTGACTTGC

CCGGCAAGTGATGGTGACTCTGTCTCCTACAGATGCAGAC

AGGGAGGATGGAGACTGGGTCATCTGGATGTCCGTCGACC

CGCCACCGCCGCTGCCACCTCCGCCTGAACCGCCTCCACC

GCTCGAGACGGTGACCAGGGTTCCCTGGCCCCAGTAGTCA

AAAGCAGTAGCAGTTTTCGCACAGTAATATACGGCCGTGT

CCTCGGCTCTCAGGCTGTTCATTTGCAGATACAGCGTGTT

CTTGGAATTGTCTCTGGAGATGGTGAACCGGCCCTTCACG

GAGTCTGCGTAACTTGTAGCATCACCATTAGAATAAATAG

ATGAGACCCACTCCAGCCCCTTCCCTGGAGCCTGGCGGAC

CCAGCTCATGGCATAGCTGCTAAAGGTGAATCCAGAGGCT

GCACAGGAGAGTCTCAGGGACCCCCCAGGCTGTACCAAGC

CTCCCCCAGACTCCAACAGCTGCACCTCGGCCATGGCCGG

CTGGGCCGCGAGTAATAACAATCCAGCGGCTGCCGTNNCA

ATAGGTATTTCATTATGACTGTCTCCTTGAAATANAATTT

GCATGCAAGCTTGGNGTAATCATGGNCATAGCTGTTTCCT

GNGTGAAATTGTTATCCGCTCACNATTCCNCACNACATA
```

M35F AA sequence:
                                        (SEQ ID NO: 24)
```
MQIXFQGDSHNEIPIXTAAAGLLLLAAQPAMAEVQLLESG

GGLVQPGGSLRLSCAASGFTFSSYAMSWVRQAPGKGLEWV

SSIYSNGDATSYADSVKGRFTISRDNSKNTLYLQMNSLRA

EDTAVYYCAKTATAFDYWGQGTLVTVSSGGGGSGGGGSGG

GGSTDIQMTQSPSSLSASVGDRVTITCRASQSISSYLNWY

QQKPGKAPKLLIYGASSLQSGVPSRFSGSGSGTDFTLTIS

GLQPEDFATYYCQQSYASPTTFGQGTKVEIKRAAAHXHHH

HGAAEQKLXSEEDLK
```

Clone M35G:
                                        (SEQ ID NO: 25)
```
CTATGCGNCCCATTCAGATCCTCTTCTGAGANGAGTTTT

TGTTCTGCGGCCCCGTGATGGTGATGATGATGTGCGGCCG

CCCGTTTGATTTCCACCTTGGTCCCTTGGCCGAACGTAGG

AGGCGAAGTCTGAACCTGTTGACAGTAGTAAGTTGCAAAA

TCTTCAGGTTGCAGACTGCTGATGGTGAGAGTGAAATCTG

TCCCAGATCCACTGCCACTGAACCTTGATGGGACCCCACT

TTGCAACAGGGATGCACGATAGATCAGGAGCTTAGGGGCT

TTCCCTGGTTTCTGCTGATACCAATTTAAATAGCTGCTAA

TGCTCTGGCTTGCCCGGCAAGTGATGGTGACTCTGTCTCC

TACAGATGCAGACAGGGAGGATGGAGACTGGGTCATCTGG

ATGTCCGTCGACCCGCCACCGCCGCTGCCACCTCCGCCTG
```

-continued

```
AACCGCCTCCACCGCTCGAGACGGTGACCAGGGTTCCCTG

GCCCCAGTAGTCAAACTGCTTACCACGTTTCGCACAGTAA

TATACGGCCGTGTCCTCGGCTCTCAGGCTGTTCATTTGCA

GATACAGCGTGTTCTTGGAATTGTCTCTGGAGATGGTGAA

CCGGCCCTTCACGGAGTCTGCGTAATGTGTCACAGTACCA

TCCGGCCAAATACCTGAGACCCACTCCAGCCCCTTCCCTG

GAGCCTGGCGGACCCAGCTCATGGCATAGCTGCTAAAGGT

GAATCCAGAGGCTGCACAGGAGAGTCTCAGGGACCCCCCA

GGCTGTACCAAGCCTCCCCCAGACTCCAACAGCTGCACCT

CGGCCATGGCCGGCTGGGCCGCGAGTAATAACAATCCAGC

GGCTGCCGTANGCAATAGGTATTTCATTATGACTGTCTCC

TTGAAATAGAATTTGCATGCAAGCTTGGCGTAANCATGGT

CATAGCTGTTTCCTGTGNGAAATTGTTATCCNGCTCACAA

TTCCNNCACAA
```

M35G AA sequence:
                                        (SEQ ID NO: 26)
```
MKYLLXTAAAGLLLLAAQPAMAEVQLLESGGGLVQPGGSL

RLSCAASGFTFSSYAMSWVRQAPGKGLEWVSGIWPDGTVT

HYADSVKGRFTISRDNSKNTLYLQMNSLRAEDTAVYYCAK

RGKQFDYWGQGTLVTVSSGGGGSGGGGSGGGGSTDIQMTQ

SPSSLSASVGDRVTITCRASQSISSYLNWYQQKPGKAPKL

LIYRASLLQSGVPSRFSGSGSGTDFTLTISSLQPEDFATY

YCQQVQTSPPTFGQGTKVEIKRAAAHHHHHHGAAEQKLXS

EEDLNGXA
```

Clone M58A:
                                        (SEQ ID NO: 27)
```
TATGCGNNNATTCNGATCCTCTTCTGAGANGAGTTTTTGT

TCTGCGGCCCCGTGATGGTGATGATGNNNTGCGGCCGCCC

GTTTGATTTCCACCTTGGTCCCTTGGCCGAACGTATTAGG

ACAATCAGTAGTCTGTTGACAGTAGTAAGTTGCAAAATCT

TCAGGTTGCAGACTGCTGATGGTGAGAGTGAAATCTGTCC

CAGATCCACTGCCACTGAACCTTGATGGGACCCCACTTTG

CAAAGTGGATGCATTATAGATCAGGAGCTTAGGGGCTTTC

CCTGGTTTCTGCTGATACCAATTTAAATAGCTGCTAATGC

TCTGACTTGCCCGGCAAGTGATGGTGACTCTGTCTCCTAC

AGATGCAGACAGGGAGGATGGAGACTGGGTCATCTGGATG

TCCGTCGACCCGCCACCGCCGCTGCCACCTCCGCCTGAAC

CGCCTCCACCGCTCGAGACGGTGACCAGGGTTCCCTGGCC

CCAGTAGTCAAAATTAGCACCAGATTTCGCACAGTAATAT

ACGGCCGTGTCCTCGGCTCTCAGGCTGTTCATTTGCAGAT

ACAGCGTGTTCTTGGAATTGTCTCTGGAGATGGTGAACCT

GCCCTTCACGGAGTCTGCGTAAGATGTAGCATAACCACTA

GCAGTAATACCTGAGACCCACTCCAGCCCCTTCCCTGGAG
```

-continued

CCTGGCGGACCCAGCTCATGGCATAGCTGCTAAAGGTGAA

TCCAGAGGCTGCACAGGAGAGTCTCANGGACCCCCCAGGC

TGTACCAAGCCTCCCCCAGACTCCAACAGCTGCACCTCGG

CCATGGCCGGCTGGGCCGCGAGTAATAACAATCCAGCGGC

TGCCGTANGCAATANGTATTTCATTATGACTGTCTCCTTG

AAATAGAANTTTGCATGCAAGCTTGGNNTAATCATGGNNA

TAGCTGTTTCCTGTGTGAAATTGTTATCCGCTCACAATTN

CNCAC

M58A AA sequence:
(SEQ ID NO: 28)
MIXPSLHAXFYFKETVIMKYXLXTAAAGLLLLAAQPAMAE

VQLLESGGGLVQPGGSXRLSCAASGFTFSSYAMSWVRQAP

GKGLEWVSGITASGYATSYADSVKGRFTISRDNSKNTLYL

QMNSLRAEDTAVYYCAKSGANFDYWGQGTLVTVSSGGGGS

GGGGSGGGGSTDIQMTQSPSSLSASVGDRVTITCRASQSI

SSYLNWYQQKPGKAPKLLIYNASTLQSGVPSRFSGSGSGT

DFTLTISSLQPEDFATYYCQQTTDCPNTFGQGTKVEIKRA

AAXHHHHHGAAEQKLXSEEDXNXRI

Clone M58C:
(SEQ ID NO: 29)
GCGGCNNNTTCNGANCCTCTTCTGAGANGAGTTTTTGTTC

TGCGGCCCCGTGNNGGTGATGNNNNNGTGCGGCCGCCCGT

TTGATTTCCACCTTGGTCCCTTGGCCGAACGTATTAGGGG

TACTGTAACTCTGTTGACAGTAGTAAGTTGCAAAATCTTC

AGGTTGCAGACTGCTGATGGTGAGAGTGAAATCTGTCCCA

GATCCACTGCCACTGAACCTTGATGGGACCCCACTTTGCA

AACTGGATGCAGCATAGATCAGGAGCTTAGGGGCTTTCCC

TGGTTTCTGCTGATACCAATTTAAATAGCTGCTAATGCTC

TGACTTGCCCGGCAAGTGATGGTGACTCTGTCTCCTACAG

ATGCAGACAGGGAGGATGGAGACTGGGTCATCTGGATGTC

CGTCGACCCGCCACCGCCGCTGCCACCTCCGCCTGAACCG

CCTCCACCGCTCGAGACGGTGACCAGGGTTCCCTGGCCCC

AGTAGTCAAACGCCGGATGATATTTCGCACAGTAATATAC

GGCCGTGTCCTCGGCTCTCAGGCTGTTCATTTGCAGATAC

AGCGTGTTCTTGGAATTGTCTCTGGAGATGGTGAACCGGC

CCTTCACGGNGTCTGCGTACTCTGTCGGCAGACCCTGCGG

CGCAATCGATGAGACCCACTCCAGCCCCTTCCCTGGAGCC

TGGCGGACCCAGCTCATGGCATAGCTGCTAAAGGTGAATC

CAGAGGCTGCACAGGAGAGTCTCAGGGACCCCCCAGGCTG

TACCAAGCCTCCCCCAGACTCCAACAGCTGCACCTCGGCC

ATGGCCGGCTGGGCCGCGAGTAATAACAATCCAGCGGCNG

NCGTANNCAATAGGTATTTCATTATGACTGTCTCCTTGAA

-continued

ATANNATTTGCATGCAAGCTTGGNGTANTCATGGNCATAG

CTGTTTNCTGNGTGNAAATTGTTATCCGCTCNNNAATTTC

CAC

M58C AA sequence:
(SEQ ID NO: 30)
MKYLLXTXAAGLLLLAAQPAMAEVQLLESGGGLVQPGGSL

RLSCAASGFTFSSYAMSWVRQAPGKGLEWVSSIAPQGLPT

EYADXVKGRFTISRDNSKNTLYLQMNSLRAEDTAVYYCAK

YHPAFDYWGQGTLVTVSSGGGGSGGGGSGGGGSTDIQMTQ

SPSSLSASVGDRVTITCRASQSISSYLNWYQQKPGKAPKL

LIYAASSLQSGVPSRFSGSGSGTDFTLTISSLQPEDFATY

YCQQSYSTPNTFGQGTKVEIKRAAAXXHHXHGAAEQKLXS

EED

Clone M59F:
(SEQ ID NO: 31)
GCGNCCNNTTCAGATCCTCTTCTGAGATGAGTTTTTGTTCT

GCGGCCCCGTGATGGTGATGANNNNNNTGCGGCCGCCCGTT

TGATTTCCACCTTGGTCCCTTGGCCGAACGTAGAAGGAGA

ATTACCAGTCTGTTGACAGTAGTAAGTTGCAAAATCTTCA

GGTTGCAGACTGCTGATGGTGAGAGTGAAATCTGTCCCAG

ATCCACTGCCACTGAACCTTGATGGGACCCCACTTTGCAA

AGCGGATGCAGTATAGATCAGGAGCTTAGGGGCTTTCCCT

GGTTTCTGCTGATACCAATTTAAATAGCTGCTAATGCTCT

GACTTGCCCGGCAAGTGATGGTGACTCTGTCTCCTACAGA

TGCAGACAGGGAGGATGGAGACTGGGTCATCTGGATGTCC

GTCGACCCGCCACCGCCGCTGCCACCTCCGCCTGAACCGC

CTCCACCGCTCGAGACGGTGACCAGGGTTCCCTGGCCCCA

GTAGTCAAAAGTACTATAAGATTTCGCACAGTAATATACG

GCCGTGTCCTCGGCTCTCAGGCTGTTCATTTGCAGATACA

GCGTGTTCTTGGAATTGTCTCTGGAGATGGTGAACCGGCC

CTTCACGGAGTCTGCGTAAGCTGTACTAGCACTACTAGCA

GCAATACCTGAGACCCACTCCAGCCCCTTCCCTGGAGCCT

GGCGGANCCAGCTCATGGCATAGCTGCTAAAGGTGAATCC

AGAGGCTGCACAGGAGAGTCTCAGGGACCCCCCAGGCTGT

ACCAAGCCTCCCCCGGACTCCAACAGCTGCACCTCGGCCA

TGGCCGGCTGGGCCGCGAGTAATAACAATCCAGCGGCTGC

CGTANGCAATANGTATTTCATTATGACTGTCTCCTTGAAA

TAGAATTTGCATGCAAGCTTGGCGTANTCATGGNCATAGC

TGNTTCCTGTGTGAAATTGNTNATCCGCTCAC

M59F AA sequence:
(SEQ ID NO: 32)
MKYXLXTAAAGLLLLAAQPAMAEVQLLESGGGLVQPGGSL

RLSCAASGFTFSSYAMSWXRQAPGKGLEWVSGIAASSAST

AYADSVKGRFTISRDNSKNTLYLQMNSLRAEDTAVYYCAK

-continued

SYSTFDYWGQGTLVTVSSGGGGSGGGGSGGGGSTDIQMTQ

SPSSLSASVGDRVTITCRASQSISSYLNWYQQKPGKAPKL

LIYTASALQSGVPSRFSGSGSGTDFTLTISSLQPEDFATY

YCQQTGNSPSTFGQGTKVEIKRAAAXXHHHHGAAEQKLIS

EEDL

Clone 4E1:
(SEQ ID NO: 33)
ATGGCCGAGGTGCAGCTGTCGGAGTCTGGGGGAGGCTTGG

TACAGCCTGGGGGGTCCCTGAGACTCTCCTGTGCAGCCTC

TGGATTCACCTTTAGCAGCTATGCCATGAGCTGGGTCCGC

CAGGCTCCAGGGAAGGGGCTGGAGTGGGTCTCAGGTATTA

ATAGTAATGGTACTTCTACATCTTACGCAGACTCCGTGAA

GGGCCGGTTCACCATCTCCAGAGACAATTCCAAGAACACG

CTGTATCTGCAAATGAACAGCCTGAGAGCCGAGGACACGG

CCGTATATTACTGTGCGAAATCTGCTTCTGATTTTGACTA

CTGGGGCCAGGGAACCCTGGTCACCGTCTCGAGCGGTGGA

GGCGGTTCAGGCGGAGGTGGCAGCGGCGGTGGCGGGTCGA

CGGACATCCAGATGACCCAGTCTCCATCCTCCCTGTCTGC

ATCTGTAGGAGACAGAGTCACCATCACTTGCCGGGCAAGT

CAGAGCATTAGCAGCTATTTAAATTGGTATCAGCAGAAAC

CAGGGAAAGCCCCTAAGCTCCTGATCTATAATGCATCCAC

TTTGCAAAGTGGGGTCCCATCAAGGTTCAGTGGCAGTGGA

TCTGGGACAGATTTCACTCTCACCATCAGCAGTCTGCAAC

CTGAAGATTTTGCAACTTACTACTGTCAACAGAATACTTA

TAGTCCTACTACGTTC

4E1 AA sequence:
(SEQ ID NO: 34)
MKYLLPTNAAGLLLLAANPAMAEVQLSESGGGLVQPGGSL

RLSCAASGFTFSSYAMSWVRQAPGKGLEWVSGINSNGTST

SYADSVKGRFTISRDNSKNTLYLQMNSLRAEDTAVYYCAK

SASDFDYWGQGTLVTVSSGGGGSGGGGSGGGGSTDIQMTQ

SPSSLSASVGDRVTITCRASQSISSYLNWYQQKPGKAPKL

LIYNASTLQSGVPSRFSGSGSGTDFTLTISSLQPEDFATY

YCQQNTYSPTTFGNNNKVEIKRAA

Clone 4H3:
(SEQ ID NO: 35)
ATGGCCGAGATGCAGCTGTTGGAGTCTGGGGGAGGCTTGG

TACAGCCTGGGGGGTCCCTGAGACTCTCCTGTGCAGCCTC

TGGATTCACCTTTAGCAGCTATGCCATGAGCTGGGTCCGC

CAGGCTCCAGGGAAGGGGCTGGAGTGGGTCTCATATATTA

CTGCTAATGGTGATAGTACAACTTACGCAGACTCCGTGAA

GGGCCGGTTCACCATCTCCAGAGACAATTCCAAGAACACG

CTGTATCTGCAAATGAACAGCCTGAGAGCCGAGGACACGG

-continued

CCGTATATTACTGTGCGAAAAGTACTACTGATTTTGACTA

CTGGGGCCAGGGAACCCTGGTCACCGTCTCGAGCGGTGGA

GGCGGTTCAGGCGGAGGTGGCAGCGGCGGTGGCGGGTCGA

CGGACATCCAGATGACCCAGTCTCCATCCTCCCTGTCTGC

ATCTGTAGGAGACAGAGTCACCATCACTTGCCGGGCAAGT

CAGAGCATTAGCAGCTATTTAAATTGGTATCAGCAGAAAC

CAGGGAAAGCCCCTAAGCTCCTGATCTATAGTGCATCCAA

TTTGCAAAGTGGGGTCCCATCAAGGTTCAGTGGCAGTGGA

TCTGGGACAGATTTCACTCTCACCATCAGCAGTCTGCAAC

CTGAAGATTTTGCAACTTACTACTGTCAACAGACTTCTTA

TAGTCCTTCTACGTTCGGCCAAGGGNCCAAGGTGGAAATC

AAACGGGCGGCC

4H3 AA Sequence:
(SEQIDNO:36)MAEMQLLESGGGLVQPGGSLRLSCAASG

FTFSSYAMSWVRQAPGKGLEWVSYITANGDSTTYADSVKG

RFTISRDNSKNTLYLQMNSLRAEDTAVYYCAKSTTDFDYW

GQGTLVTVSSGGGGSGGGGSGGGGSTDIQMTQSPSSLSAS

VGDRVTITCRASQSISSYLNWYQQKPGKAPKLLIYSASNL

QSGVPSRFSGSGSGTDFTLTISSLQPEDFATYYCQQTSYS

PSTFGQGXKVEIKRAA

Clone 1A5:
(SEQ ID NO: 37)
ATGGCCGAGGTGCAGCTGTTGGAGTCTGGGGGAGGCTTGG

TACAGCCTGGGGGNTCCCTGAGACTCTCCTGTGCAGCCTC

TGGATTCACCTTTAGCAGCTATGCCATGAGCTGGGTCCGC

CAGGCTCCAGGGAAGGGGCTGGAGTGGGTCTCAACTATTA

ATGCTAGTGGTGGTAGTACAGGTTACGCAGACTCCGTGAA

GGGCCGGTTCACCATCTCCAGAGACAATTCCAAGAACACG

CTGTATCTGCAAATGAACAGCCTGAGAGCCGAGGACACGG

CCGTATATTACTGTGCGAAAGCTGATGCTTATTTTGACTA

CTGGGGCCAGGGAACCCTGGTCACCGTCTCGAGCGGTGGA

GGCGGTTCAGGCGGAGGTGGCAGCGGCGGTGGCGGGTCGA

CGGACATCCAGATGACCCAGTCTCCATCCTCCCTGTCTGC

ATCTGTAGGAGACAGAGTCACCATCACTTGCCGGGCAAGT

CAGAGCATTAGCAGCTATTTAAATTGGTATCAGCAGAAAC

CAGGGAAAGCCCCTAAGCTCCTGATCTATTCTGCATCCTC

GTTGCAAAGTGGGGTCCCATCAAGGTTCAGTGGCAGTGGA

TCTGGGACAGATTTCACTCTCACCATCAGCAGTCTGCAAC

CTGAAGATTTTGCAACTTACTACTGTCAACAGGATGCTAG

TGGTCCTTCTACGTTCGGCCAAGGGACCAAGGTGGAAATC

AAACGGGCGGCCGCA

-continued

1A5 AA Sequence:

(SEQ ID NO: 38)

MAEVQLLESGGGLVQPGGSLRLSCAASGFTFSSYAMSWVR

QAPGKGLEWVSTINASGGSTGYADSVKGRFTISRDNSKNT

LYLQMNSLRAEDTAVYYCAKADAYFDYWGQGTLVTVSSGG

GGSGGGGSGGGGSTDIQMTQSPSSLSASVGDRVTITCRAS

QSISSYLNWYQQKPGKAPKLLIYSASSLQSGVPSRFSGSG

SGTDFTLTISSLQPEDFATYYCQQDASGPSTFGQGTKVEI

KRAA

Clone 3D3:

(SEQ ID NO: 39)

ATGGCCGAGGTGCAGCTGTTGGAGTCTGGGGGAGGCTTGG

TACAGCCTGGGGGGTCCCTGAGACTCTCCTGTGCAGCCTC

TGGATTCACCTTTAGCAGCTATGCCATGAGCTGGGTCCGC

CAGGCTCCAGGGAAGGGGCTGGAGTGGGTCTCATATATTG

CTGATGATGGTGCTAATACAGCTTACGCAGACTCCGTGAA

GGGCCGGTTCACCATCTCCAGAGACAATTCCAAGAACACG

CTGTATCTGCAAATGAACAGCCTGAGAGCCGAGGACACGG

CCGTATATTACTGTGCGAAAAATAATGATGGTTTTGACTA

CTGGGGCCAGGGAACCCTGGTCACCGTCTCGAGCGGTGGA

GGCGGTTCAGGCGGAGGTGGCAGCGGCGGTGGCGGGTCGA

CGAACATCCAGATGACCCAGTCTCCATCCTCCCTGTCTGC

ATCTGTAGGAGACAGAGTCACCATCACTTGCCGGGCAAGT

CAGAGCATTAGCAGCTATTTAAATTGGTATCAGCAGAAAC

CAGGGAAAGCCCCTAAGCTCCTGATCTATTCTGCATCCAC

TTTGCAAAGTGGGGTCCCATCAAGGTTCAGTGGCAGTGGA

TCTGGGACAGATTTCACTCTCACCATCAGCAGTCTGCAAC

CTGAAGATTTTGCAACTTACTACTGTCAACAGGCTGCTAC

TAGTCCTTCTACGTTCGGCCAAGGGNCCAAGGTGGAAATC

AAACGGGCGGNCGCAC

3D3 AA Sequence:

(SEQ ID NO: 40)

MAEVQLLESGGGLVQPGGSLRLSCAASGFTFSSYAMSWVR

QAPGKGLEWVSYIADDGANTAYADSVKGRFTISRDNSKNT

LYLQMNSLRAEDTAVYYCAKNNDGFDYWGQGTLVTVSSGG

GGSGGGGSGGGGSTNIQMTQSPSSLSASVGDRVTITCRAS

QSISSYLNWYQQKPGKAPKLLIYSASTLQSGVPSRFSGSG

SGTDFTLTISSLQPEDFATYYCQQAATSPSTFGQGXKVEI

KRAXA

The following TBI Clone Sequences were identified:

Clone T2B:

(SEQ ID NO: 41)

TTCAAGGAGACAGTCATAATGAAATANCCTATTGCNTACG

GCANNCGCTGGATTGTTATTACTCGCGGCCCAGCCNGNCC

-continued

ATGGCCGAGGTGCAGCTGTTGGAGTCTGGGGGAGGCTTGG

TACAGCCTGGGGGGTCCCTGAGACTCTCCTGTGCAGCCTC

TGGATTCACCTTTAGCAGCTATGCCATGAGCTGGGTCCGC

CAGGCTCCAGGGAAGGGGCTGGAGTGGGTCTCAAATATTA

GTTCTGATGGTGATTCTACAGCTTACGCAGACTCCGTGAA

GGGCCGGTTCACCATCTCCAGAGACAATTCCAAGAACACG

CTGTATCTGCAAATGAACAGCCTGAGAGCCGAGGACACGG

CCGTATATTACTGTGCGAAAGCTTCTAGTAATTTTGACTA

CTGGGGCCAGGGAACCCTGGTCACCGTCTCGAGCGGTGGA

GGCGGTTCAGGCGGAGGTGGCAGCGGCGGTGGCGGGTCGA

CGGACATCCAGATGACCCAGTCTCCATCCTCCCTGTCTGC

ATCTGTAGGAGACAGAGTCACCATCACTTGCCGGGCAAGT

CAGAGCATTAGCAGCTATTTAAATTGGTATCAGCAGAAAC

CAGGGAAAGCCCCTAAGCTCCTGATCTATGCTGCATCCAA

TTTGCAAAGTGGGGTCCCATCAAGGTTCAGTGGCAGTGGA

TCTGGGACAGATTTCACTCTCACCATCAGCAGTCTGCAAC

CTGAAGATTTTGCAACTTACTACTGTCAACAGTCTAATTC

TGATCCTACTACGTTCGGCCAAGGGACCAAGGTAATCAAA

CGGGCGGCCGCACATCATCATCACCATCACGGGGCCGCAG

AACAAAAACTCNTCTCAGAAGAGGATCTGAATGGNNCCGC

ATAGNC

T2B AA sequence:

(SEQ ID NO: 42)

MAEVQLLESGGGLVQPGGSLRLSCAASGFTFSSYAMSWVR

QAPGKGLEWVSNISSDGDSTAYADSVKGRFTISRDNSKNT

LYLQMNSLRAEDTAVYYCAKASSNFDYWGQGTLVTVSSGG

GGSGGGGSGGGGSTDIQMTQSPSSLSASVGDRVTITCRAS

QSISSYLNWYQQKPGKAPKLLIYAASNLQSGVPSRFSGSG

SGTDFTLTISSLQPEDFATYYCQQSNSDPTTFGQGTKVIK

RAAAHHHHHHGAAEQKLXSEEDLNXXA

Clone T1H:

(SEQ ID NO: 43)

CAGGGGGGGCGGNGCCTATGNAAAAAACGCCAGCAACGCG

GCCTTTTACGGTTCCTGGCCCTTTGCTGGCCTTTTGCTCA

CATGTTCTTTCCTGCGTTATCCCCTGATTCTGTGGATAAC

CGTATTACCGCCTTTGAGTGAGCTGATACCGCTCGCCGCA

GCCGAACGACCGAGCGCAGCGAGTCAGTGAGCGAGGAAGC

GGAAGAGCGCCCAATACGCAAACCGCCTCTCCCCGCGCGT

TGGCCGATTCATTAATGCAGCTGGCACGACAGGTTTCCCG

ACTGGAAAGCGGGCAGTGAGCGCAACGCAATTAATGTGAG

TTAGCTCACTCATTAGGCACCCCAGGCTTTACACTTTATG

CTCCCGGCTCGTATGTTGTGTGGAATTGTGAGCGGATAAC

-continued

AATTTCACACAGGAAACAGCTATGACCATGATTACGCCAA

GCTTGCATGCAAATTCTATTTCAAGGAGACAGTCATAGCT

AGCATGAAAAAGATTTGGCTGGCGCTGGCTGGTTTAGTTT

TAGCGTTTAGCGCATCGGCGGACTACAAAGAGGCCCAGCC

GGCCATGGACCTGGGTAAGAAACTGCTGGAAGCTGCTCGT

GCTGGTCAGGACGACGAAGTTCGTATCCTGATGGCTAACG

GTGCTGACGTTAACGCTCATGACGAACAGGGTACTACTCC

GCTGCACCTGGCTGCTAAAGAAGGTCACCTGGAAATCGTT

GAAGTTCTGCTGAAGTACGGTGCTGACGTTAACGCTCAGG

ACAAATTCGGTAAGACCGCTTTCGACATCTCCATCGACAA

CGGTAACGAGGACCTGGCTGAAATCCTGCAAGCGGCCGCA

CATCATCATCACCATCACGGGGCCGCAGAACAAAAACTCA

TCTCAGAAGAGGATCTGAATGGCCGCNTA

T1H AA sequence:
                              (SEQ ID NO: 44)
MLPARMLCGIVSGQFHTGNSYDHDYAKLACKFYFKETVIA

SMKKIWLALAGLVLAFSASADYKEAQPAMDLGKKLLEAAR

AGQDDEVRILMANGADVNAHDEQGTTPLHLAAKEGHLEIV

EVLLKYGADVNAQDKFGKTAFDISIDNGNEDLAEILQAAA

HHHHHHGAAEQKLISEEDLNGRX

Clone T3F:
                              (SEQ ID NO: 45)
GAGCTATGAGANNNNNNCCACGCTTCCCCNAAGGGAGAAAG

GCGGACAGGTATCCCGGTAAGCNGGCAGGGTCGGAACAGG

AGAGCGCACGAGGGAGNNTNCAGGGGGAAACGCCTGGTAT

CTTTATAGTCCTGTCGGNNTTTCGCCACCTCTGACTTGAG

CGTCGATTTTTTGTGATGCTCGTCAGGGGGGCGGAGCCTA

TGGAAAAACGCCAGCAACGCGGCCTTTTTACGGTTCCTGG

CCTTTTGCTGGCCTTTTGCTCACATGTTCTTTCCTGCGTT

ATCCCCTGATTCTGTGGATAACCGTATTACCGCCTTTGAG

TGAGCTGATACCGCTCGCCGCAGCCGAACGACCGAGCGCA

GCGAGTCAGTGAGCGAGGAAGCGGAAGAGCGCCCAATACG

CAAACCGCCTCTCCCCGCGCGTTGGCCGATTCATTAATGC

AGCTGGCACGACAGGTTTCCCGACTGGAAAGCGGGCAGTG

AGCGCAACGCAATTAATGTGAGTTAGCTCACTCATTAGGC

ACCCCAGGCTTTACACTTTATGCTCCCGGCTCGTATGTTG

TGTGGAATTGTGAGCGGATAACAATTTCACACAGGAAACA

GCTATGACCATGATTACGCCAAGCTTGCATGCAAATTCTA

TTTCAAGGAGACAGTCATAGCTAGCATGAAAAAGATTTGG

CTGGCGCTGGCTGGTTTAGTTTTAGCGTTTAGCGCATCGG

CGGACTACAAAGAGGCCCAGCCGGCCATGGTAGGAAGACC

TGACGTTAACGCTCAGGACAAATTCGGTAAGACCGCTTTC

GACATCTCCATCGACAACGGTAACGAGGACCTGGCTGAAA

-continued

TCCTGCAAGCGGCCGCACatCaTCATCACCATCACGGGGC

CGCAGAACAAAAACTCNTCTCAGAAGAGGATCNGAANNNN

NCGCNTAGA

T3F AA sequence:
                              (SEQ ID NO: 46)
MFFPALSPDSVDNRITAFEADTARRSRTTERSESVSEEAE

ERPIRKPPLPARWPIHCSWHDRFPDWKAGSERNAINVSLT

HAPQALHFMLPARMLCGIVSGQFHTGNSYDHDYAKLACKF

YFKETVIASMKKIWLALAGLVLAFSASADYKEAQPAMVGR

PDVNAQDKFGKTAFDISIDNGNEDLAEILQAAAHHHHHHG

AAEQKLXSEED

Clone T3G:
                              (SEQ ID NO: 47)
TCGTCAGGGGGGNCGGNAGCCTATGGAAAAAACGNNAGCA

ACGNGNCNTTTTTACGGNNNNTGGCCTTTTGCTGGCNTTT

GCTCACATGTTCTTTCCTGCGTTNNCCCCTGATTCTGTGG

ATANCCGTATTACCGCCTTTNGAGTGAGCTGATACCGNTC

GCCGCAGCCGAACGACCGAGCGCAGCGAGTCAGTGAGCGA

GGAAGCGGAAGAGCGCCCAATACGCAAACCGCCTCTCCCC

GCGCGTTGGCCGATTCATTAATGCAGCTGGCACGACAGGT

TTCCCGACTGGAAAGCGGGCAGTGAGCGCAACGCAATTAA

TGTGAGTTAGCTCACTCATTAGGCACCCCAGGCTTTACAC

TTTATGCTCCCGGCTCGTATGTTGTGTGGAATTGTGAGCG

GATAACAATTTCACACAGGAAACAGCTATGACCATGATTA

CGCCAAGCTTGCATGCAAATTCTATTTCAAGGAGACAGTC

ATAGCTAGCATGAAAAAGATTTGGCTGGCGCTGGCTGGTT

TAGTTTTAGCGTTTAGCGCATCGGCGGACTACAAAGAGGC

CCAGCCGGCCATGGACCTGGGTAAGAAACTGCTGGAAGCT

GCTCGTGCTGGTCAGGACGACGAAGTTCGTATCCTGATGG

CTAACGGTGCTGACGTTAACGCTTGGGACATGACTGGTCA

TACTCCGCTGCACCTGGCTGCTCAGTTCGGTCACCTGGAA

ATCGTTGAAGTTCTGCTGAAGCACGGTGCTGACGTTAACG

CTCAGGACAAATTCGGTAAGACCGCTTTCGACATCTCCAT

CGACAACGGTAACGAGGACCTGGCTGAAATCCTGCAAGCG

GCCGCACatcatCATCACCATCACGGGGcCGCAGAACAAA

AAcTCaTcTCAGAAGAGGATNNGAANGNNNCCGCA

T3G AA sequence:
                              (SEQ ID NO: 48)
MLPARMLCGIVSGQFHTGNSYDHDYAKLACKFYFKETVIA

SMKKIWLALAGLVLAFSASADYKEAQPAMDLGKKLLEAAR

AGQDDEVRILMANGADVNAWDMTGHTPLHLAAQFGHLEIV

EVLLKHGADVNAQDKFGKTAFDISIDNGNEDLAEILQAAA

HHHHHHGAAEQKLISEED

-continued        -continued

Clone TIA:

(SEQ ID NO: 49)

TTTATAGTNCNTGTCGGGTTTCNCCACNTNTGACNTGAGC

NTCGATNTTTNNNNTGCTCNNCAGGGGGGCGGAGCCTATG

GAAAAACGNCAGCAACGCGNCNTTTNTNCGGTTNNTGNCN

TTTTGCTGGCCTTTTGCTCACATGTTCTTTCNTGCGTTAT

CCCNTGATTNTGTGGATANCCGTATTACCGCCTTTGAGTG

AGCTGATACCGCTCGCCGCANNCGAACGACCGAGCGCAGN

GAGTCAGTGAGCGAGGAAGCGGAAGAGCGCCCAATACGCA

AACCGCCTCTCNCCGCGCGTTGGCCGATTCATTAATGCAG

CTGGCACGACAGGTTTNNNGACTGGAAAGCGGGCAGTGAG

CGCAACGCAATTAATGTGAGTTAGCTCACTCATTAGGCAC

CCCAGGCTTTACACTTTATGCTCCCGGCTCGTATGTTGTG

TGGAATTGTGAGCGGATAACAATTTCACACAGGAAACAGN

TATGACCATGATTACGCCAAGCTTGCATGCAAATTCTATT

TCAAGGAGACAGTCATAGCTAGCATGAAAAAGATTTGGCT

GGCGCTGGCTGGTTTAGTTTTAGCGTTTAGCGCATCGGCG

GANTACAAAGAGGCCCAGCCGGCCATGGGCGGAACCAGCA

GTTTNTTACCCAGGTCCATGGACCTGGGTCACCTGGAAAT

CGTTGAAGTTCTGCTGAAGTACGGTGNTGACGTTAACGNT

CAGGACAAATTCGGTAAGACCGCTTTCGACATNTCCATCG

ACAACGGTAACGAGGACCTGGCTGAAATCCTGCAAGCGGC

CGCACATCATCATCACCATCATCGGGCTCGCAGAACAAAA

ATCATCTC

TIA AA sequence:

(SEQ ID NO: 50)

MFFXALSXDXVDXRITAFEADTARRXRTTERXESVSEEAE

ERPIRKPPLXARWPIHCSWHDRFXDWKAGSERNAINVSLT

HAPQALHFMLPARMLCGIVSGQFHTGNXYDHDYAKLACKF

YFKETVIASMKKIWLALAGLVLAFSASAXYKEAQPAMGGT

SSXLPRSMDLGHLEIVEVLLKYGXDVNXQDKFGKTAFDXS

IDNGNEDLAEILQAAAHHHHHHRARRTKII

Clone T1D:

(SEQ ID NO: 51)

GAGCCTATGGAAAAAACGCCCAGCAACGCGGCNTTTTTAC

GGTTCCTGGCCTTTTGCTGNCNTTTTGNTCACATGTTCT

TTCCTGCGTTATCCCCTGATTCTGTGGATAACCGTATTAC

CGCCTTTGAGTGNNNNGATACCGCTCGCCGCAGCCGAACG

ACCGAGCGCAGCGAGTCAGTGAGCGAGGAAGCGGAAGAGC

GCCCAATACGCAAACCGCCTCTCCCCGCGCGTTGGCCGAT

TCATTAATGCAGCTGGCACGACAGGTTTCCCGACTGGAAA

GCGGGCAGTGAGCGCAACGCAATTAATGTGAGTTAGCTCA

CTCATTAGGCACCCCAGGCTTTACACTTTATGCTCCCGGC

TCGTATGTTGTGTGGAATTGTGAGCGGATAACAATTTCAC

ACAGGAAACAGCTATGACCATGATTACGCCAAGCTTGCAT

GCAAATTCTATTTCAAGGAGACAGTCATAGCTAGCATGAA

AAAGATTTGGCTGGCGCTGGCTGGTTTAGTTTTAGCGTTT

AGCGCATCGGCGGACTACAAAGAGGCCCAGCCGGCCATGG

ACCTGGGTAAGAAACTGCTGGAAGCTGCTCGTGCTGGTCA

GGACGACGAAGTTCGTATCCTGATGGCTAACGGTGCTGAC

GTTAACGCTGACGACTTCTCTGGTACTACTCCGCTGCACC

TGGCTGCTCATCATGGTCACCTGGAAATCGTTGAAGTTCT

GCTGAAGTACGGTGCTGACGTTAACGCTCAGGACAAATTC

GGTAAGACCGCTTTCGACATCTCCATCGACAACGGTAACG

AGGACCTGGCTGAAATCCTGCAAGCGGCCGCANNNNNNCA

TCACCATCACGGGGCCGCAGAACAAAAACTCNNNCAGAAG

AGGATNNGAANNNNCGCATA

T1D AA sequence:

(SEQ ID NO: 52)

MFFPALSPDSVDNRITAFEXXDTARRSRTTERSESVSEEA

EERPIRKPPLPARWPIHCSWHDRFPDWKAGSERNAINVSL

THAPQALHFMLPARMLCGIVSGQFHTGNSYDHDYAKLACK

FYFKETVIASMKKIWLALAGLVLAFSASADYKEAQPAMDL

GKKLLEAARAGQDDEVRILMANGADVNADDFSGTTPLHLA

AHHGHLEIVEVLLKYGADVNAQDKFGKTAFDISIDNGNED

LAEILQAAAXXHHHHGAAEQKLX

Clone T2C:

(SEQ ID NO: 53)

GANGNTCNNCAGGGGGGGCGGAGCCTATNGAAAAAACGCC

AGCAACGCGGCNTTTTTTACGGTTCCTGGCCTTTTGCTGG

CCTTTTGCTCACATGTTCTTTCCTGCGTTATCCCCTGATT

CTGTGGATANCCGTATTACCGCCTTTGAGTGAGCTGATAC

CGCTCGCCGCAGCCGAACGACCGAGCGCAGCGAGTCAGTG

AGCGAGGAAGCGGAAGAGCGCCCAATACGCAAACCGCCTC

TCCCCGCGCGTTGGCCGATTCATTAATGCAGCTGGCACGA

CAGGTTTCCCGACTGGAAAGCGGGCAGTGAGCGCAACGCA

ATTAATGTGAGTTAGCTCACTCATTAGGCACCCCAGGCTT

TACACTTTATGCTCCCGGCTCGTATGTTGTGTGGAATTGT

GAGCGGATAACAATTTCACACAGGAAACAGCTATGACCAT

GATTACGCCAAGCTTGCATGCAAATTCTATTTCAAGGAGA

CAGTCATAGCTAGCATGAAAAAGATTTGGCTGGCGCTGGC

TGGTTTAGTTTTAGCGTTTAGCGCATCGGCGGACTACAAA

GAGGCCCAGCCGGCCATGGACCTGGGTAAGAAACTGCTGG

AAGCTGCTCGTGCTGGTCAGGACGACGAAGTTCGTATCCT

GATGGCTAACGGTGCTGACGTTAACGCTCTGGACGAAGTT

GGTTCTACTCCGCTGCACCTGGCTGCTATGGCTGGTCACC

-continued

```
TGGAAATCGTTGAAGTGCTGAAGCACGGTGCTGACGTTAA

CGCTCAGGACAAATTCGGTAAGACCGCTTTCGACATCTCC

ATCGACAACGGTAACGAGGACCTGGCTGAAATCCTGCAAG

CGGCCGCACATCATCATCACCATCACGGGGCCGCAGAACA

AAAACTCATCTCAGAAGAGGATCTGAATGNNNCGCNTAG
```

T2C AA sequence:

(SEQ ID NO: 54)
```
MLPARMLCGIVSGQFHTGNSYDHDYAKLACKFYFKETVIA

SMKKIWLALAGLVLAFSASADYKEAQPAMDLGKKLLEAAR

AGQDDEVRILMANGADVNALDEVGSTPLHLAAMAGHLEIV

EVLKHGADVNAQDKFGKTAFDISIDNGNEDLAEILQAAAH

HHHHHGAAEQKLISEED
```

Clone T2F:

(SEQ ID NO: 55)
```
GGACAGGNTATCCGGTAAAGCGGCAGGGTCGGANCANNAG

AGCGCACGAGGGAGCTTNNCAGGGGGAAACGCCTGGTATC

TTTATAGTCCTGTCGGNTTTCGCCCACCTCTGACTTGAGC

GTCGATTTTTGTGATGCTCGTCAGGGGGGCGGAGCCTAT

GGAAAAACGCCAGCAACGCGGCCTTTTTACGGTTCCTGGC

CTTTTGCTGGCCTTTTGCTCACATGTTCTTTCCTGCGTTA

TCCCCTGATTCTGTGGATAACCGTATTACCGCCTTTGAGT

GAGCTGATACCGCTCGCCGCAGCCGAACGACCGAGCGCAG

CGAGTCAGTGAGCGAGGAAGCGGAAGAGCGCCCAATACGC

AAACCGCCTCTCCCCGCGCGTTGGCCGATTCATTAATGCA

GCTGGCACGACAGGTTTCCCGACTGGAAAGCGGGCAGTGA

GCGCAACGCAATTAATGTGAGTTAGCTCACTCATTAGGCA

CCCCAGGCTTTACACTTTATGCTCCCGGCTCGTATGTTGT

GTGGAATTGTGAGCGGATAACAATTTCACACAGGAAACAG

CTATGACCATGATTACGCCAAGCTTGCATGCAAATTCTAT

TTCAAGGAGACAGTCATAGCTAGCATGAAAAAGATTTGGC

TGGCGCTGGCTGGTTTAGTTTTAGCGTTTAGCGCATCGGC

GGACTACAAAGAGGCCCAGCCGGCCATGGACCTGGCTGCT

CATGTTGGTCACCTGGAAATCGTTGAAGTTCTGCTGAAGT

ACGGTGCTGACGTTAACGCTCAGGACAAATTCGGTAAGAC

CGCTTTCGACATCTCCATCGACAACGGTAACGAGGACCTG

GCTGAAATCCTGCAAGCGGCCgCACatCaTCATCACCATC

ACGGGGCCGCAGAACAAAAACTCaTCTCAGAAGAGGATCT

GANNNNNCGCNTAG
```

T2F AA sequence:

(SEQ ID NO: 56)
```
MFFPALSPDSVDNRITAFEADTARRSRTTERSESVSEEAE

ERPIRKPPLPARWPIHCSWHDRFPDWKAGSERNAINVSLT

HAPQALHFMLPARMLCGIVSGQFHTGNSYDHDYAKLACKF

YFKETVIASMKKIWLALAGLVLAFSASADYKEAQPAMDLA
```

-continued

```
AHVGHLEIVEVLLKYGADVNAQDKFGKTAFDISIDNGNED

LAEILQAAAHHHHHHGAAEQKLISEEDL
```

A "variant" of an amino acid sequence described herein, or a nucleic acid sequence encoding such an amino acid sequence, is a sequence that is substantially similar to SEQ ID NO:1-56. Variant amino acid and nucleic acid sequences include synthetically derived amino acid and nucleic acid sequences, or recombinantly derived amino acid or nucleic acid sequences. Generally, amino acid or nucleic acid sequence variants of the invention will have at least 40, 50, 60, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to SEQ ID NO: 1-56. The present invention includes variants of the amino acid sequences of the antibodies and antibody fragments described herein, as well as variants of the nucleic acid sequences encoding such amino acid sequences (i.e., SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55 or SEQ ID NO:56).

"Variants" are intended to include sequences derived by deletion (so-called truncation) or addition of one or more amino acids to the N-terminal and/or C-terminal end, and/or addition of one or more bases to the 5' or 3' end of the nucleic acid sequence; deletion or addition of one or more amino acids/nucleic acids at one or more sites in the sequence; or substitution of one or more amino acids/nucleic acids at one or more sites in the sequence. The amino acids described herein may be altered in various ways including amino acid substitutions, deletions, truncations, and insertions. Methods for such manipulations are generally known in the art. For example, amino acid sequence variants can be prepared by mutations in the DNA. Methods for mutagenesis and nucleotide sequence alterations are well known in the art. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall protein retains its spatial conformation but does not alter its biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains.

As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

Nucleic Acids and Vectors

In certain embodiments, the present invention provides a nucleic acid encoding the amino acids described herein.

In certain embodiments, the present invention provides a vector comprising the nucleic acid described herein.

In certain embodiments, the present invention provides a phage comprising the vector described herein.

As used herein, the term "nucleic acid" and "polynucleotide" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

A "nucleic acid fragment" is a portion of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" may also be used interchangeably with gene, cDNA, DNA and RNA encoded by a gene, e.g., genomic DNA, and even synthetic DNA sequences. The term also includes sequences that include any of the known base analogs of DNA and RNA.

By "fragment" or "portion" is meant a full length or less than full length of the nucleotide sequence.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have in at least one embodiment 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

As used herein, "sequence identity" or "identity" in the context of two nucleic acid sequences makes reference to a specified percentage of residues in the two sequences that are the same when aligned by sequence comparison algorithms or by visual inspection.

As used herein, "percentage of sequence identity" means the value determined by comparing two optimally aligned sequences, wherein the portion of the polynucleotide sequence may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70%, 71%, 72%, 73%, 74%, 75%, 76%, 77%, 78%, or 79%; at least 80%, 81%, 82%, 83%, 84%, 85%, 86%, 87%, 88%, or 89%; at least 90%, 91%, 92%, 93%, or 94%; or even at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code.

As noted above, another indication that two nucleic acid sequences are substantially identical is that the two molecules hybridize to each other under stringent conditions. The phrase "hybridizing preferentially to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched nucleic acid. Specificity is typically the function of post-hybridization washes, the critical factors being the ionic strength and temperature of the final wash solution. For DNA-DNA hybrids, the $T_m$ can be approximated from the equation of Meinkoth and Wahl: $T_m$ 81.5° C.+16.6 (log M)+0.41 (% GC)−0.61 (% form)−500/L. M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. Generally, highly stringent hybridization and wash conditions are selected to be about 5° C. lower than the thermal melting point ($T_m$) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

"Operably-linked" nucleic acids refers to the association of nucleic acid sequences on single nucleic acid fragment so that the function of one is affected by the other, e.g., an arrangement of elements wherein the components so described are configured so as to perform their usual function. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. Control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

The terms "isolated and/or purified" refer to in vitro isolation of a nucleic acid, e.g., a DNA or RNA molecule from its natural cellular environment, and from association with other components of the cell or test solution (e.g. RNA pool), such as nucleic acid or polypeptide, so that it can be sequenced, replicated, and/or expressed. For example, "isolated nucleic acid" may be a DNA molecule containing less than 31 sequential nucleotides that is transcribed into an RNAi molecule. Such an isolated RNAi molecule may, for example, form a hairpin structure with a duplex 21 base pairs in length that is complementary or hybridizes to a sequence in a gene of interest, and remains stably bound under stringent conditions (as defined by methods well known in the art, e.g., in Sambrook and Russell, 2001). Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

As used herein, the term "derived" or "directed to" with respect to a nucleotide molecule means that the molecule has complementary sequence identity to a particular molecule of interest.

In certain embodiments, the expression cassette further contains a promoter. In certain embodiments, the promoter is a regulatable promoter. In certain embodiments, the promoter is a constitutive promoter. In certain embodiments, the promoter is a PGK, CMV or RSV promoter.

The present invention provides a vector containing the expression cassette described above. Expression vectors include, but are not limited to, viruses, plasmids, and other vehicles for delivering heterologous genetic material to cells. Accordingly, the term "expression vector" as used herein refers to a vehicle for delivering heterologous genetic material to a cell. In particular, the expression vector is a recombinant adenoviral, adeno-associated virus, or lentivirus or retrovirus vector. In certain embodiments, the viral vector is an adenoviral, lentiviral, adeno-associated viral (AAV), poliovirus, HSV, or murine Maloney-based viral vector.

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. It also may include sequences required for proper translation of the nucleotide sequence. The coding region usually codes for a protein of interest. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of a regulatable promoter that initiates transcription only when the host cell is exposed to some particular stimulus. In the case of a multicellular organism, the promoter can also be specific to a particular tissue or organ or stage of development.

Binding Molecules

As used herein, the term "binding molecule" includes antibodies, which includes scFvs (also called a "nanobodies"), humanized, fully human or chimeric antibodies, single-chain antibodies, diabodies, and antigen-binding fragments of antibodies (e.g., Fab fragments).

In certain embodiments, the binding molecule does not contain the constant domain region of an antibody.

In certain embodiments, the binding molecule is less than 500 amino acids in length, such as between 200-450 amino acids in length, or less than 400 amino acids in length.

In certain embodiments, the binding molecule preferentially recognizes a particular stage of human AD Tau (e.g., AD Braak Stage I, compared to other AD stages).

In certain embodiments, the binding molecule preferentially recognizes tau associated with TBI.

In certain embodiments, the binding molecule binds to AD Tau. In certain embodiments, the binding molecule comprises an amino acid sequence of SEQ ID NO: 2, 4, 6, 8, 10, 12, 14, 16, 18, 20, 22, 24, 26, 28, 30, 32, 34, 36, 38, or 40. In certain embodiments, the binding molecule comprises an amino acid sequence encoded by a nucleic acid, wherein the nucleic acid has at least 80% identity to SEQ ID NO: 1, 3, 5, 7, 9, 11, 13, 15, 17, 19, 21, 23, 25, 27, 29, 31, 33, 35, 37, or 39.

In certain embodiments, the binding molecule binds to TBI Tau. In certain embodiments, the binding molecule comprises an amino acid sequence of SEQ ID NO: 42, 44, 46, or 48, 50, 52, 54, 56. In certain embodiments, the binding molecule comprises an amino acid sequence encoded by a nucleic acid, wherein the nucleic acid has at least 80% identity to SEQ ID NO: 41, 43, 45, 47, 49, 51, 53, or 55.

Detection Reagents and Assays

For purposes of the diagnostic methods of the invention, the compositions or ligand of the invention (e.g., binding molecule such as an antibody or antibody fragment) may be conjugated to a detecting reagent that facilitates detection of the ligand. For example, example, the detecting reagent may be a direct label or an indirect label. The labels can be directly attached to or incorporated into the detection reagent by chemical or recombinant methods.

In one embodiment, a label is coupled to the ligand through a chemical linker. Linker domains are typically polypeptide sequences, such as poly gly sequences of between about 5 and 200 amino acids. In some embodiments, proline residues are incorporated into the linker to prevent the formation of significant secondary structural elements by the linker. In certain embodiments, linkers are flexible amino acid subsequences that are synthesized as part of a recombinant fusion protein comprising the RNA recognition domain. In one embodiment, the flexible linker is an amino acid subsequence that includes a proline, such as Gly(x)-Pro-Gly(x) where x is a number between about 3 and about 100 (SEQ ID NO: 57). In other embodiments, a chemical linker is used to connect synthetically or recombinantly produced recognition and labeling domain subsequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

The detectable labels can be used in the assays of the present invention to diagnose TBI, these labels are attached to the ligand of the invention, can be primary labels (where the label comprises an element that is detected directly or that produces a directly detectable element) or secondary labels (where the detected label binds to a primary label, e.g., as is common in immunological labeling). An introduction to labels, labeling procedures and detection of labels is found in Polak and Van Noorden (1997) Introduction to Immunocytochemistry, 2nd ed., Springer Verlag, N.Y. and in Haugland (1996) Handbook of Fluorescent Probes and Research Chemicals, a combined handbook and catalogue Published by Molecular Probes, Inc., Eugene, Oreg. Patents that described the use of such labels include U.S. Pat. Nos. 3,817,837; 3,850,752; 3,939,350; 3,996,345; 4,277,437; 4,275,149; and 4,366,241.

Primary and secondary labels can include undetected elements as well as detected elements. Useful primary and secondary labels in the present invention can include spectral labels such as green fluorescent protein, fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$P, etc.), enzymes (e.g., horse radish peroxidase, alkaline phosphatase etc.), spectral calorimetric labels such as colloidal gold or colored glass or plastic (e.g. polystyrene, polypropylene, latex, etc.) beads. The label can be coupled directly or indirectly to a component of the detection assay (e.g., the detection reagent) according to methods well known in the art. As indicated above, a wide variety of labels may be used, with the choice of label depending on sensitivity required, ease of conjugation with the compound, stability requirements, available instrumentation, and disposal provisions.

Exemplary labels that can be used include those that use: 1) chemiluminescence (using horseradish peroxidase and/or alkaline phosphatase with substrates that produce photons as breakdown products as described above) with kits being available, e.g., from Molecular Probes, Amersham, Boehringer-Mannheim, and Life Technologies/Gibco BRL; 2) color production (using both horseradish peroxidase and/or alkaline phosphatase with substrates that produce a colored precipitate (kits available from Life Technologies/Gibco BRL, and Boehringer-Mannheim)); 3) fluorescence using, e.g., an enzyme such as alkaline phosphatase, together with the substrate AttoPhos (Amersham) or other substrates that produce fluorescent products, 4) fluorescence (e.g., using Cy-5 (Amersham), fluorescein, and other fluorescent tags); 5) radioactivity. Other methods for labeling and detection will be readily apparent to one skilled in the art.

Where the ligand-based compositions of the invention are contemplated to be used in a clinical setting, the labels are preferably non-radioactive and readily detected without the necessity of sophisticated instrumentation. In certain embodiments, detection of the labels will yield a visible signal that is immediately discernable upon visual inspection. One example of detectable secondary labeling strategies uses an antibody that recognizes oligomers in which the antibody is linked to an enzyme (typically by recombinant or covalent chemical bonding). The antibody is detected when the enzyme reacts with its substrate, producing a detectable product. In certain embodiments, enzymes that can be conjugated to detection reagents of the invention include, e.g., 0-galactosidase, luciferase, horse radish peroxidase, and alkaline phosphatase. The chemiluminescent substrate for luciferase is luciferin. One embodiment of a fluorescent substrate for β-galactosidase is 4-methylumbelliferyl-β-D-galactoside. Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl) spiro[1,2-dioxetane-3,2'-adamantane], which is detected with a luminometer. Embodiments of horse radish peroxidase substrates include 2,2'azino-bis(3-ethylbenzthiazoline-6 sulfonic acid) (ABTS), 5-aminosalicylic acid (5AS), o-dianisidine, and o-phenylenediamine (OPD), which are detected with a spectrophotometer, and 3,3,5,5'-tetramethylbenzidine (TMB), 3,3' diaminobenzidine (DAB), 3-amino-9-ethylcarbazole (AEC), and 4-chloro-1-naphthol (4C1N), which are detected visually. Other suitable substrates are known to those skilled in the art. The enzyme-substrate reaction and product detection are performed according to standard procedures known to those skilled in the art and kits for performing enzyme immunoassays are available as described above.

The presence of a label can be detected by inspection, or a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis.

The ligand compositions of the invention can be used in any diagnostic assay format to determine the presence of human CSF/brain-associated tau variants. A variety of immunodetection methods are contemplated for this embodiment. Such immunodetection methods include enzyme linked immunosorbent assay (ELISA), radioimmunoassay (RIA), immunoradiometric assay, fluoroimmunoassay, chemiluminescent assay, bioluminescent assay, and Western blot, though several others are well known to those of ordinary skill. The steps of various useful immunodetection methods have been described in the scientific literature.

In general, the binding methods include obtaining a sample suspected of containing a protein, polypeptide and/or peptide (e.g., human CSF/brain-associated Tau variants), and contacting the sample with a first antibody, monoclonal or polyclonal, in accordance with the present invention, as the case may be, under conditions effective to allow the formation of complexes.

The binding methods include methods for detecting and quantifying the amount of the target oligomer component in a sample and the detection and quantification of any complexes formed during the binding process. Here, one would obtain a sample suspected of containing target oligomers, and contact the sample with an antibody fragment of the invention, and then detect and quantify the amount of complexes formed under the specific conditions.

Contacting the chosen biological sample with the antibody under effective conditions and for a period of time sufficient to allow the formation of complexes (primary complexes) is generally a matter of simply adding the antibody composition to the sample and incubating the mixture for a period of time long enough for the antibodies to form complexes with, i.e., to bind to, any antigens present. After this time, the sample-antibody composition, such as a tissue section, ELISA plate, dot blot or western blot, will generally be washed to remove any non-preferentially bound antibody species, allowing only those scFv molecules preferentially bound within the primary complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939, 350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

As noted above, a ligand of the invention may itself be linked to a detectable label, wherein one would then simply detect this label, thereby allowing the amount of the primary complexes in the composition to be determined. Alternatively, a first antibody that becomes bound within the primary complexes may be detected by means of a second binding ligand that has binding affinity for the complex. In these cases, the second binding ligand may be linked to a detectable label. The second binding ligand is itself often an antibody, which may thus be termed a "secondary" ligand. The primary complexes are contacted with the labeled, secondary binding ligand or antibody under effective conditions and for a period of time sufficient to allow the formation of secondary complexes. The secondary complexes are then generally washed to remove any non-specifically bound labeled secondary antibodies or ligands, and the remaining label in the secondary complexes is then detected.

Further methods include the detection of primary complexes by a two-step approach. A second binding ligand, such as an antibody, that has binding affinity for the scFv is used to form secondary complexes, as described above. After washing, the secondary complexes are contacted with a third binding ligand or antibody that has binding affinity for the second antibody, again under effective conditions and for a period of time sufficient to allow the formation of complexes (tertiary complexes). The third ligand or antibody is linked to a detectable label, allowing detection of the tertiary complexes thus formed. This system may provide for signal amplification if this is desired.

One method of immunodetection designed by Charles Cantor uses two different antibodies. A first step biotinylated, monoclonal or polyclonal antibody or antibody fragment (in the present example a scFv) is used to detect the target antigen(s), and a second step antibody is then used to detect the biotin attached to the complex. In this method the sample to be tested is first incubated in a solution containing the first step ligand. If the target antigen is present, some of the ligand binds to the antigen to form a biotinylated ligand/antigen complex. The ligand/antigen complex is then amplified by incubation in successive solutions of streptavidin (or avidin), biotinylated DNA, and/or complementary biotinylated DNA, with each step adding additional biotin sites to the ligand/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of detection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

As detailed above, the assays in their most simple and/or direct sense are binding assays. Certain preferred assays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

The diagnostic assay format that may be used in the present invention could take any conventional format such as ELISA or other platforms such as luminex or biosensors. The present invention provides various ligands (e.g., scFv). These ligands can readily be modified to facilitate diagnostic assays, for example a tag (such as GFP) can be added to these ligands to increase sensitivity. In one exemplary ELISA, ligands (e.g., scFvs) are immobilized onto a selected surface exhibiting protein affinity, such as a well in a polystyrene microtiter plate. Then, a test composition suspected of containing a target oligomer, such as a clinical sample (e.g., a biological sample obtained from the subject), is added to the wells. After binding and/or washing to remove non-specifically bound complexes, the bound antigen may be detected. Detection is generally achieved by the addition of an antibody that is linked to a detectable label. This type of ELISA is a simple "sandwich ELISA." Detection may also be achieved by the addition of a second antibody, followed by the addition of a third antibody that has binding affinity for the second antibody, with the third antibody being linked to a detectable label.

In another exemplary ELISA, the samples suspected of containing the antigen are immobilized onto the well surface and/or then contacted with binding agents. After binding and/or washing to remove non-specifically bound complexes, the bound anti-binding agents are detected. Where the initial binding agents are linked to a detectable label, the complexes may be detected directly. Again, the complexes may be detected using a second antibody that has binding affinity for the first binding agents, with the second antibody being linked to a detectable label.

Another ELISA in which the antigens are immobilized, involves the use of antibody competition in the detection. In this ELISA, labeled antibodies (or nanobodies) against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes.

In coating a plate with either target oligomers or a ligand (e.g., antibody) of the invention, one will generally incubate the wells of the plate with a solution of the antigen or ligand, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the tau oligomers and/or scFv composition with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. An example of a washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. This may be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

Diagnostic Methods

In certain embodiments, the present invention provides a method for determining risk of traumatic brain injury (TBI) and/or susceptibility to neurodegenerative disease in a subject by measuring levels of particular tau oligomeric proteins preferentially associated with different stages of AD or with TBI.

In certain embodiments, the present invention provides a method for determining risk of traumatic brain injury (TBI), assessment of the amount of neuronal damage, and/or susceptibility to neurodegenerative disease in a subject, comprising the steps of:

(A) providing a sample obtained from a subject post-injury;
(B) assessing levels of TBI-associated tau in the sample;
(C) comparing the TBI-associated tau protein level in the sample with TBI-associated tau protein level in a normal control; and
(D) determining whether the subject has a risk of TBI in accordance with the result of step (C);
wherein a subject having elevated TBI-associated tau protein has a high risk of TBI.

In certain embodiments, the sample and the normal control are blood product samples or cerebrospinal fluid (CSF) samples. In certain embodiments, the blood product is serum.

In certain embodiments, the detecting in step (B) is by means of a ligand specific for the protein.

In certain embodiments, the ligand is an antibody.

In certain embodiments, the ligand is a scFv specific for TBI-associated tau.

In certain embodiments, the protein levels are detected by means of ELISA.

The invention will now be illustrated by the following non-limiting Example.

Example 1

Isolation of Nanobodies Selective for Tau Species in TBI but not ND CSF Samples

Morphology-specific nanobodies are used to identify the set of serum biomarkers that are diagnostic for AD, and determine if these also show up in a subset of TBI patients. Soldiers suffering TBI who show reactivity similar to the AD biomarker set, have suffered damage similar to that shown in AD brain, and should be much more susceptible to AD. The goal is to rapidly and accurately detect and quantify a selected set of toxic protein variants of Aβ, tau and a-syn that are characteristic of AD.

Nanobodies specific to selected tau species unique to TBI were isolated. Tau is present in human tissue in a variety of different forms since it is generated through multiple splicing events and can have a variety of different post-translational modifications. Because of the diversity of tau species, there are selected species that are indicative of particular neuronal conditions such as AD or other tauopathies. Nanobodies were generated that selectively recognize tau species present in TBI patients.

Immunoprecipitate Total Tau from Two Different Regions of Age Matched Post-Mortem Human AD and Cognitively Normal Brain Tissue Brain Tissue and CSF: AD and normal brain tissue samples were obtained from Banner/Sun Health Brain Bank (BSHBB). Samples were obtained from two different brain regions of AD cases confirmed to have abundant tangles, the superior frontal gyrus and middle temporal gyrus. Ten different AD and 10 different control patient samples were received for a total of 20 AD and 20 control samples. All subjects had a PMI less than 5 hours. Detailed clinical and neuropathological data were available on these subjects, including MMSE, CERAD neuritic plaque density scores, Braak tangle stage and regional Lewy-type alpha-syncleinopathy density scores. Post-mortem samples were de-identified for all personal patient information. CSF from four different patients who had sustained head injury and control CSF from 15 normal/healthy individuals were obtained from Banner Sun Health. These samples were used to identify potential markers in traumatic brain injury compared to control.

Brain tissue lysis: Briefly, frozen samples were homogenized by supersonication in cold lysis buffer: 25 mM HEPES NaOH (pH 7.9), 150 mM NaCl, 1.5 mM $MgCl_2$, 0.2 mM EDTA, 0.5% Triton-X-100, 1 mM dithiothreitol, protease inhibitor cocktail. The homogenized sample was centrifuged and the supernatant was frozen in $-80°$ C. The presence of fibrillar tau was verified by immunohistochemistry using slices from one AD and one ND sample and staining with an antibody against phosphorylated tau. The AD sample showed significantly more tau tangle pathology than the control sample (FIG. 1).

Figure 2:
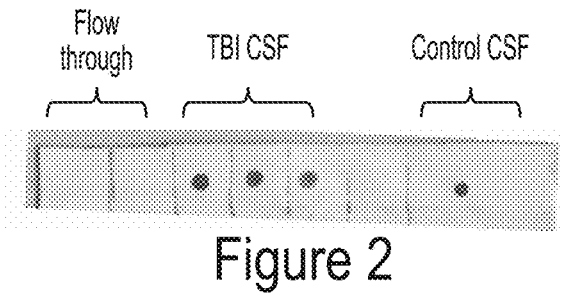
FIG. 2: Dotblot assay confirming the presence of immunoprecipitated tau from TBI and control CSF samples in the IP elutes following immunoprecipitation protocol.
Figure 3A:
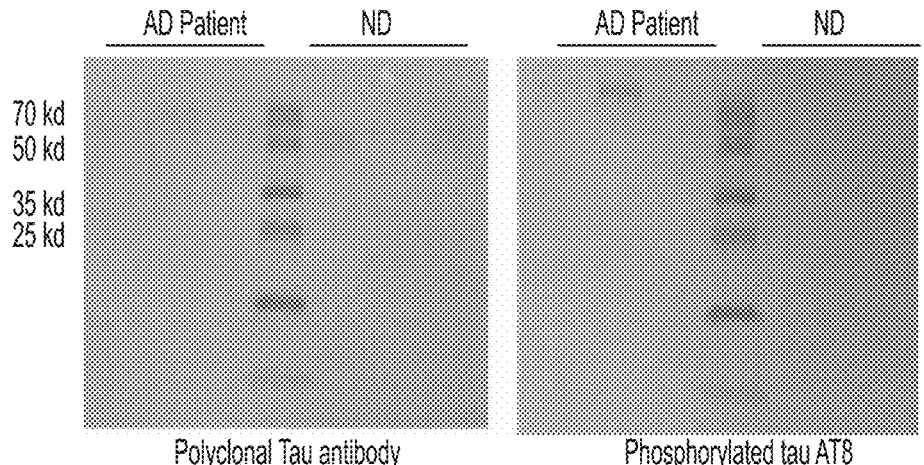
FIGS. 3a and 3b.
Figure 3B:
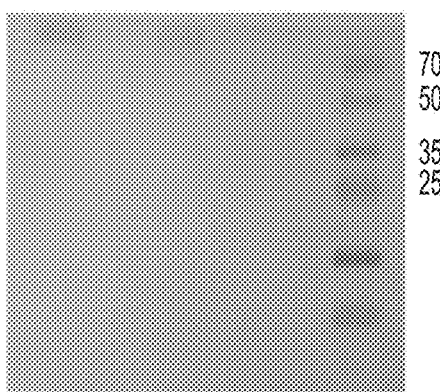

Immunoprecipitation of tau protein: Two polyclonal tau antibody preparations were used to immunoprecipitate tau from the AD brain homogenates, TBI CSF and corresponding controls: PA1 against amino-acids 240-450 of tau and PA5 against amino-acid 1-286 to cover all isoforms. Antibody conjugates were captured using the Pierce Crosslink IP Kit A following the manufacturers' protocols. With the crosslink kit, the antibody first binds the protein A/G agarose and then is chemically crosslinked to the resin preventing the antibody from eluting off the column. Tau was eluted from the column using a low pH elution buffer. To preserve integrity of the tau aggregates, the elution buffer was neutralized with 1M Tris, pH 9.5 as recommended by the manufacturer. The brain slices (FIG. 1) were analyzed and tau eluted from TBI CSF using dot blots (FIG. 2), and tau eluted from the brain tissue by western blot (FIGS. 3a and 3b).

Figure 4:
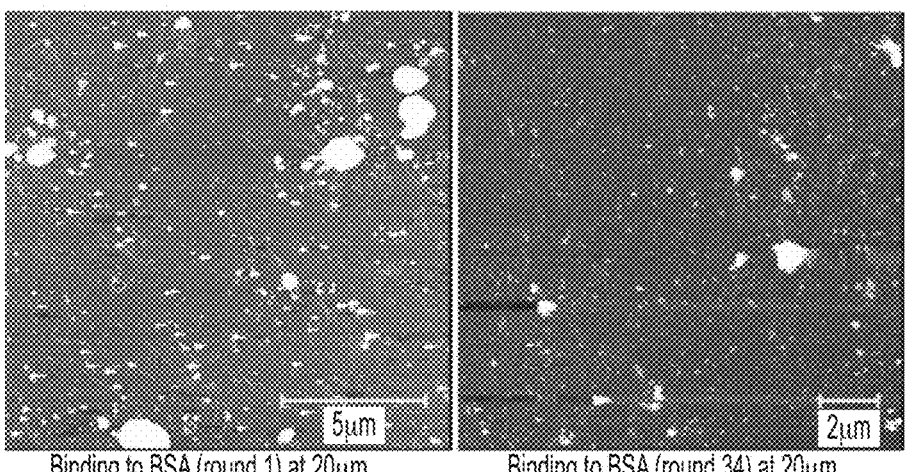
FIG. 4: Negative panning against bovine serum albumin.

Biopanning—AD tau specific morphologies: Aliquots of the Sheets, Tomlinson I and J and DARPin scFv libraries were grown and combined to generate scFv library stock with titers of around 10e13. Negative panning steps were performed to remove phage clones that bind to non-target sticky protein samples including bovine serum album (FIG. 4). Several rounds of negative panning was performed against a-synuclein aggregates to remove all antibody fragments that bind generic forms of aggregated protein morphologies. Additional negative panning steps against monomeric tau, healthy tissue samples and healthy tau samples were performed to remove all antibody fragments that bind to generic forms of tau found in healthy individuals. Atomic force microscopy (AFM) imaging was performed after every negative panning step to ensure removal of non-specific antibody fragments. Final positive selection was performed using for AD braak stage III and V specific tau variant morphologies.

Figure 5:
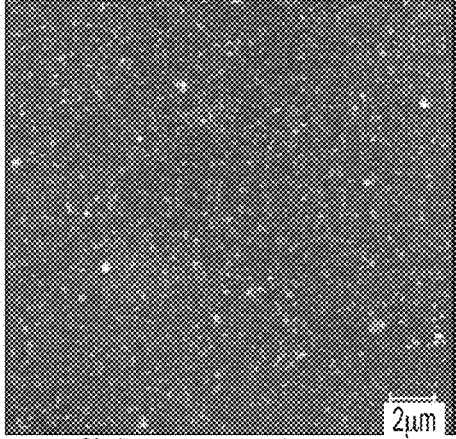
FIG. 5: Negative panning against aggregated α-synuclein.
Figure 5:
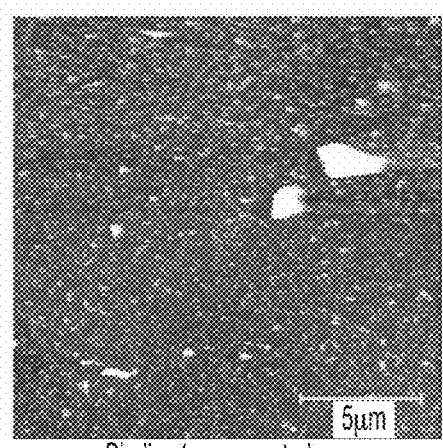
Figure 6:
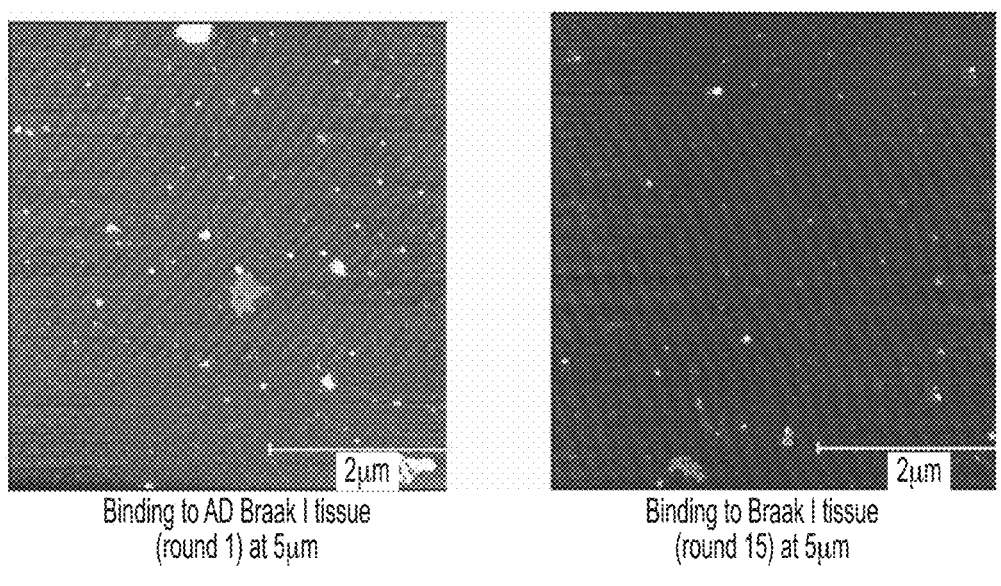
FIG. 6: Negative panning against AD Braak stage I tissue.
Figure 7:
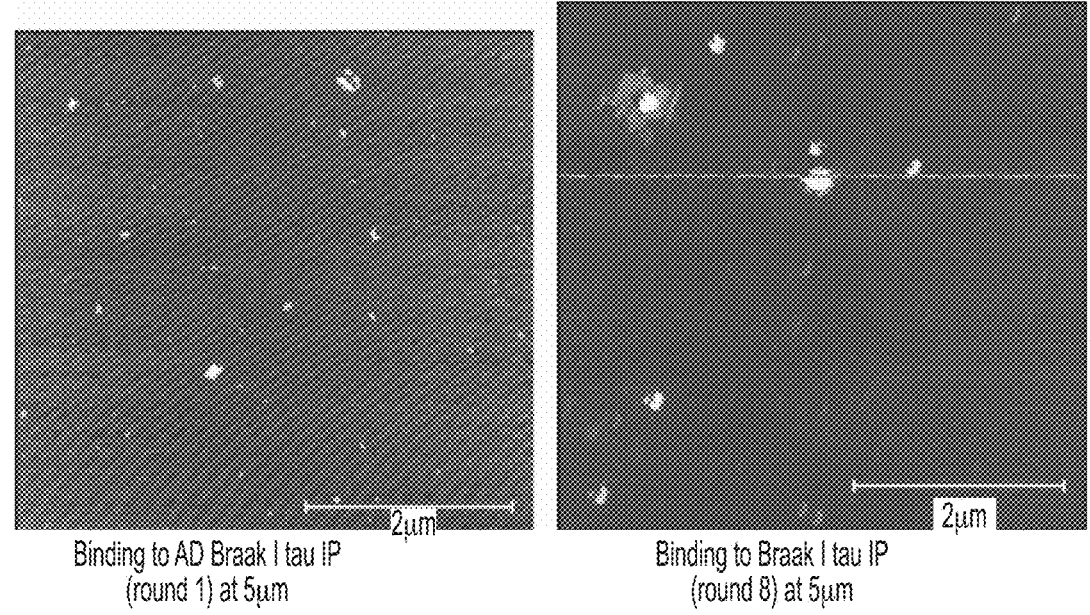
FIG. 7: Negative panning against AD Braak stage I tau IP (Black arrow indicates phage).

TBI tau specific morphologies: A clone that could bind to all forms of tau is essential and is used as a secondary detection reagent in sandwich ELISA. Hence, phage obtained after negative panning with α-synuclein (FIG. 5) was used for positive panning against monomeric tau. For panning against tau isolated from TBI, eight rounds of negative panning against control CSF samples (10 μg/mL) were first performed. Cleaved mica surface was used to conserve sample. This step was used to remove all phage binding to proteins and other components present in normal CSF including any tau variants present in healthy individuals. Phage remaining after negative panning against BSA, α-synuclein and control CSF was used to carry out positive panning with tau immunoprecipitated from TBI CSF samples (FIGS. 6, 7). Positive binding clones were eluted using either Trypsin or TEA and recovered by infecting TG1 cells.

Figure 8:
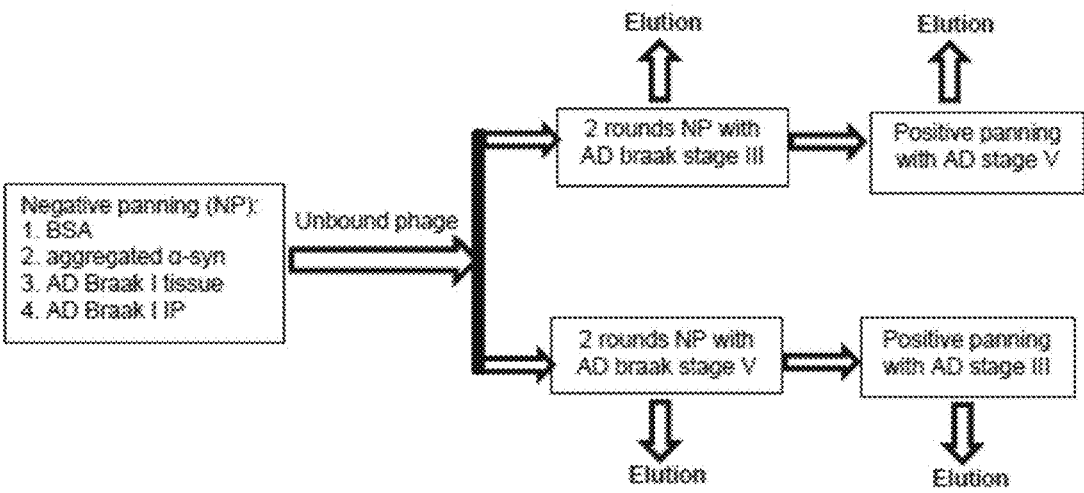
FIG. 8: Flow diagram indicating steps in the panning protocol. Negative selection to remove non-specific clones was followed by positive selection with tau immunoprecipitated from AD Braak stage III and Braak stage V.

AD tau clones: After two rounds of positive panning with AD Braak stage III, unbound phage clones were used for a positive round of selection against AD Braak stage V and vice versa (FIG. 8). Each of the micas was eluted using trypin and TEA and grown on LB-Amp plates overnight at $37°$ C. About 60 clones were obtained before negative panning with AD Braak stage III and V. Typically 50-100 clones are obtained in this step and the results obtained are encouraging. After further rounds of negative panning with AD Braak stage V and III, 15 and 20 clones were obtained against AD Braak stage III and Braak stage V respectively. The number of clones after the final rounds of positive panning was as anticipated. To ensure these clones are capable of making full length antibody fragment, their sequences were checked for any mutations and stop codons. Phage was produced for clone sequences free of any errors. Dotblots spotted with human AD homogenized brain tissue and corresponding controls were used to verify each of the phage clones.

TBI tau clone: Approximately 24 clones were recovered from the panning against tau variants present in the TBI CSF samples. Typically it is expected to recover around 20-50 clones in the positive panning step so this was an encouraging result. These clones were further sequenced to check for any stop codons or mutations. This step ensures that these clones are capable of making full length antibody fragments. Several clones isolated against TBI had complete sequences free of any stop codons, mutations or errors. Phage was produced for such clones which were verified using dotblots using TBI CSF and corresponding CSF controls. The blot was visualized using a chemiluminescent substrate and the blot was developed using film. The dot-blots showed high binding to TBI and relatively lower binding to controls. Further characterization using ELISA assays were performed.

Indirect AD ELISA: Indirect ELISA was performed to check the specificity of each of the phage clones to tau variants in AD brain tissue. The assay parameters and wash steps were optimized to yield a high signal to noise ratio. Human brain homogenates (mix of individual samples classified by their Braak stage) was used to coat the plates and 2% milk was used subsequently to block the wells. Each of the phage clones were tested with pooled ND controls, AD Braak stage III and AD Braak stage V homogenates. Secondary anti-M13 and chemiluminescent substrate was used for detection. The luminescence was measured using a spectrophotometer and represented as a ratio with respect to ND control.

Figure 9:
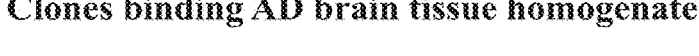
FIG. 9: Indirect ELISA assay testing different AD tau phage clones with pooled AD brain tissue homogenates. X axis represents the various clones and Y axis represents luminescence signal ratio to ND controls. All the clones have high levels of binding to AD tissue (Braak stage III and V) compared to the controls.
Figure 9:
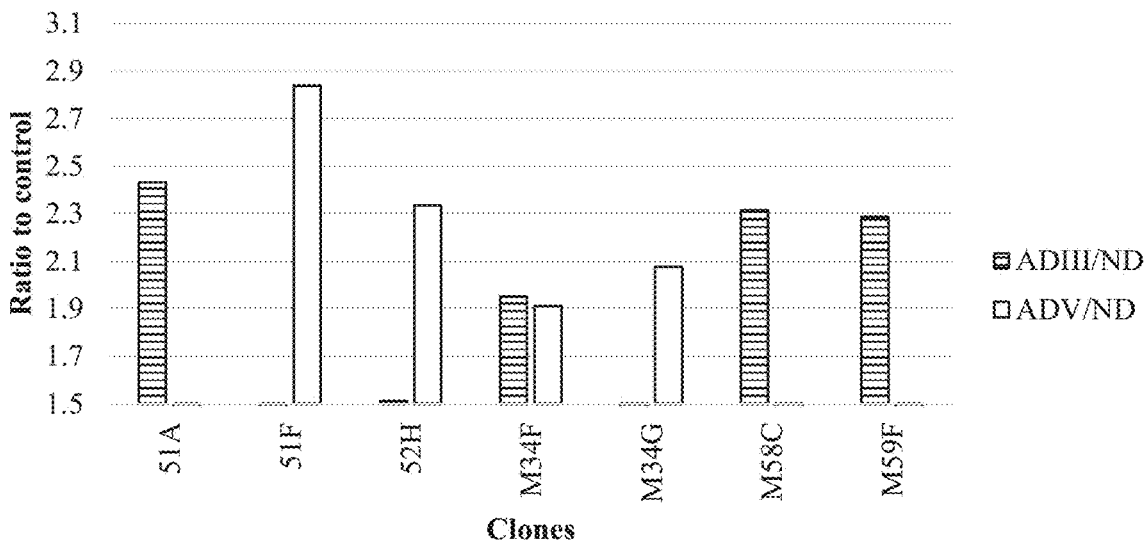

The clones were initially screened with pooled samples to check if they selected AD over control samples. From this initial assay it can be noted that several clones preferentially bound to tau morphologies in AD Braak stage III (51A, M58C and M59F) and there were a few clones (51F, 52H and M34G) that preferentially bound to tau forms present in AD Braak stage V (FIG. 9). This indicates that unique tau species exist during different AD Braak stages. These clones serve as a tool in tracking the progression of AD. Other clones that preferentially bound to both AD Braak stage III and V (M34F) indicate overlap of tau species common to Braak stages III and V. These clones serve as a potential secondary reagent for detection in a sandwich ELISA.

Figure 10:
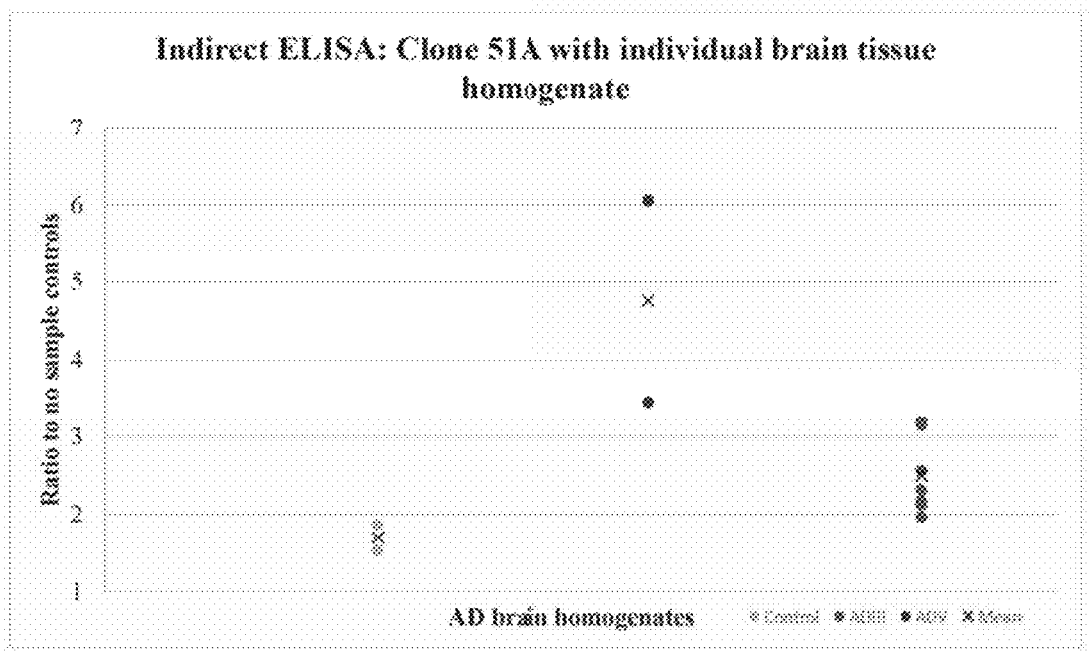
FIG. 10: Indirect ELISA of clone 51A with individual AD brain tissue homogenates. 7 samples (Braak V), 2 samples (Braak III) and 2 samples (Braak I) were tested. This clone binds tau morphologies present in AD Braak stage III.
Figure 11:
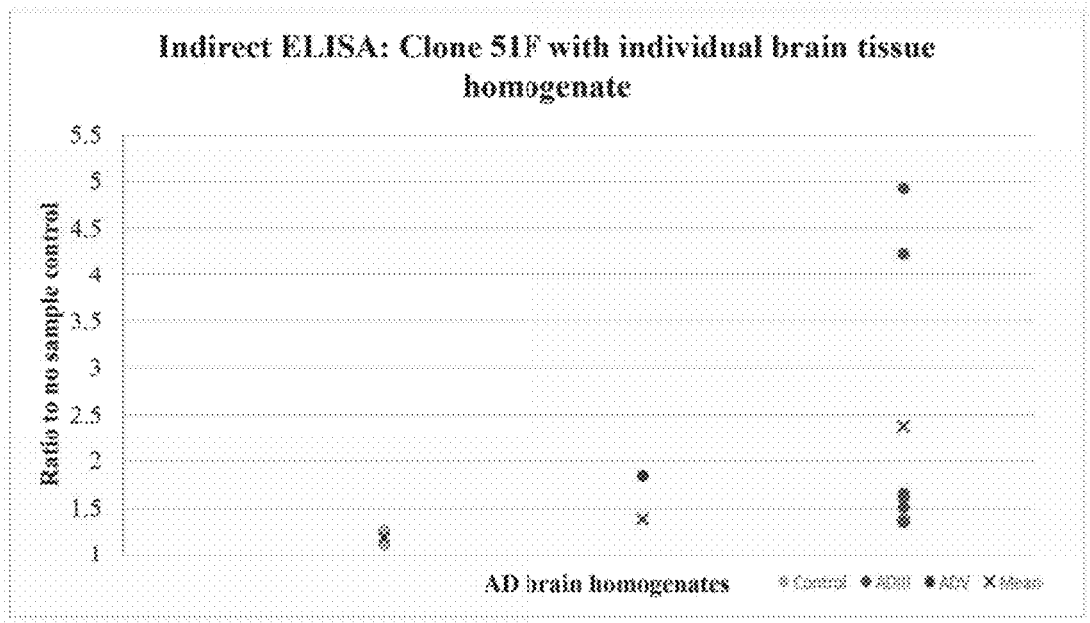
FIG. 11: Indirect ELISA of clone 51F with individual AD brain tissue homogenates. 7 samples (Braak V), 2 (Braak III) and 2 (Braak I) were tested. This clone binds tau morphologies in AD Braak stage V.
Figure 12:
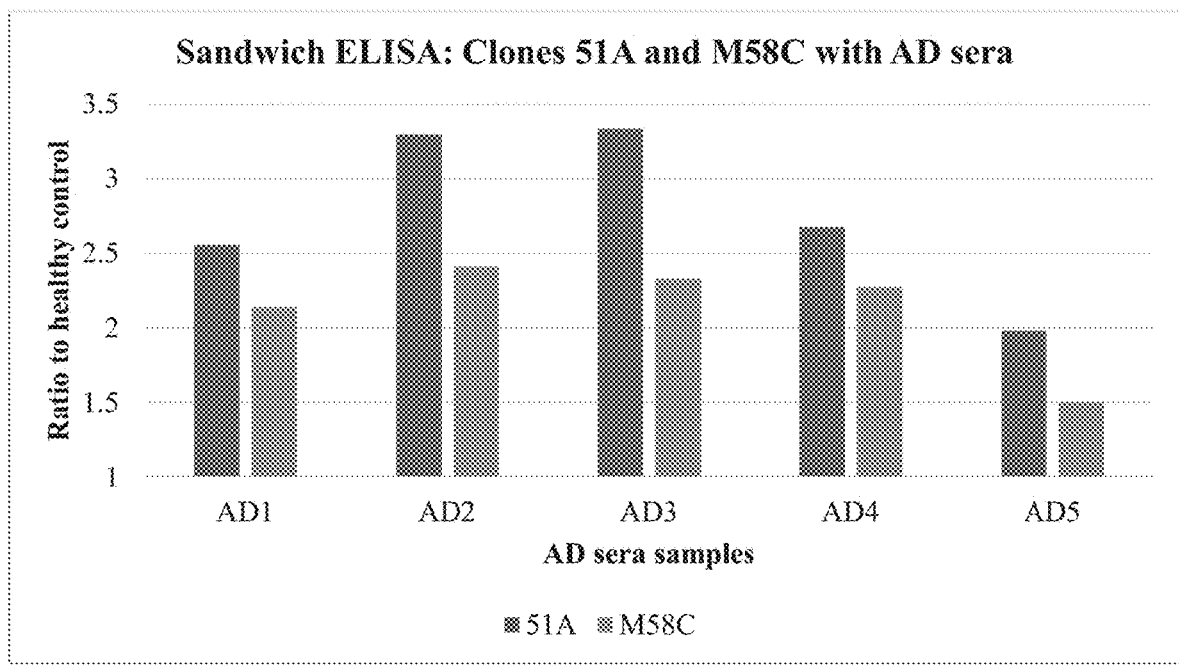
FIG. 12: Sandwich ELISA with AD clones 51A and M58C with 5 AD sera samples. X-Axis represents individual sera samples and Y-Axis represents ratio to healthy control. Both the clones selectively bind to tau morphologies present in AD sera over healthy control.

51A and 51F clones had high binding ratios to AD Braak stage III and V respectively in the initial ELISA assay. These clones were further tested with individual AD brain tissue homogenates (FIGS. 10 through 12). They selectively bind to individual samples classified under Braak stage III and V respectively. Both these clones have relatively very low binding to ND control indicating that the negative panning steps against the ND controls was successful.

Indirect TBI ELISA: Indirect ELISA was performed to check the specificity of each of the phage clones to tau variants in TBI CSF. The assay parameters and wash steps were optimized to yield a high signal to noise ratio. Pooled TBI and control CSF samples were used to coat the plates and milk was used subsequently to block the wells. Each of the phage clones were tested with AD I, ADIII and ADV homogenates. Secondary anti-M13 and chemiluminescent substrate was used for detection. The luminescence was measured using a spectrophotometer and represented as a ratio with respect to no sample control.

Figure 13:
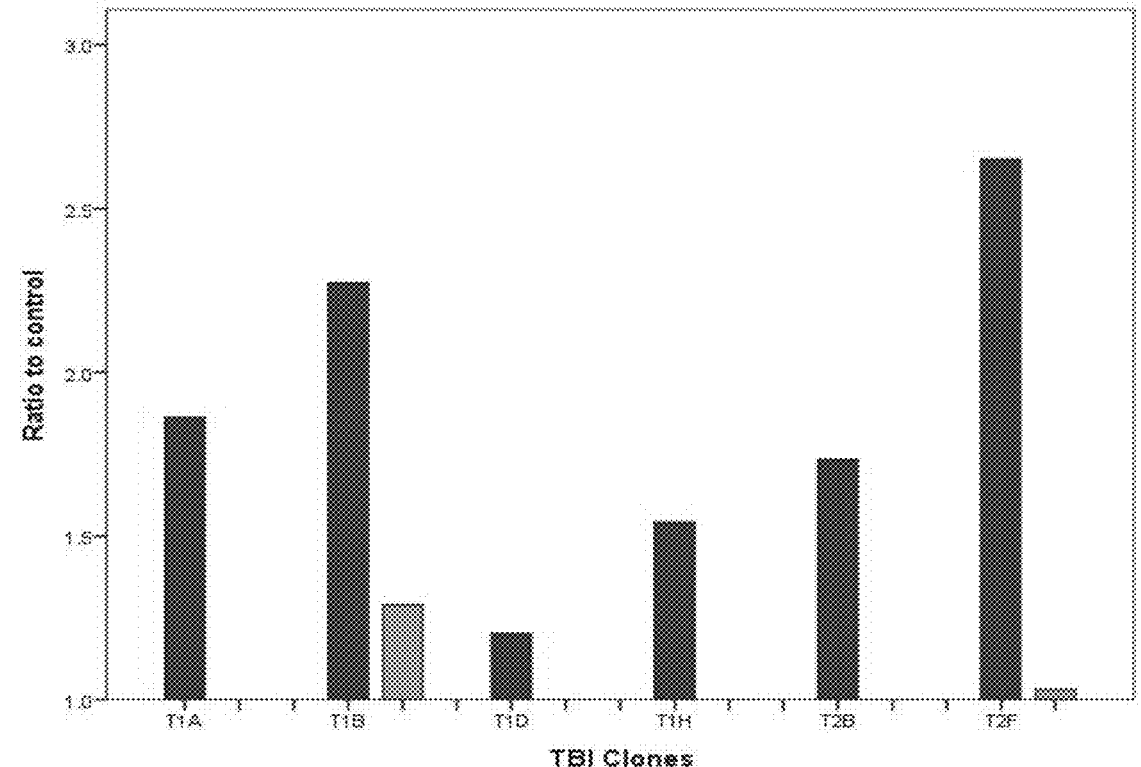
FIG. 13: Indirect ELISA of TBI clones with pooled TBI and control CSF. X axis represents the TBI clones and Y axis represents ratio to no sample control. Most of the clones had high levels of binding to TBI compared to control.

Several clones preferentially bound to tau morphologies in TBI CSF over control (FIG. 13). This indicates that unique tau species circulate in the CSF of traumatic brain injured individuals compared to controls. These clones can serve as a tool in differentiating TBI and healthy individuals.

Figure 14:
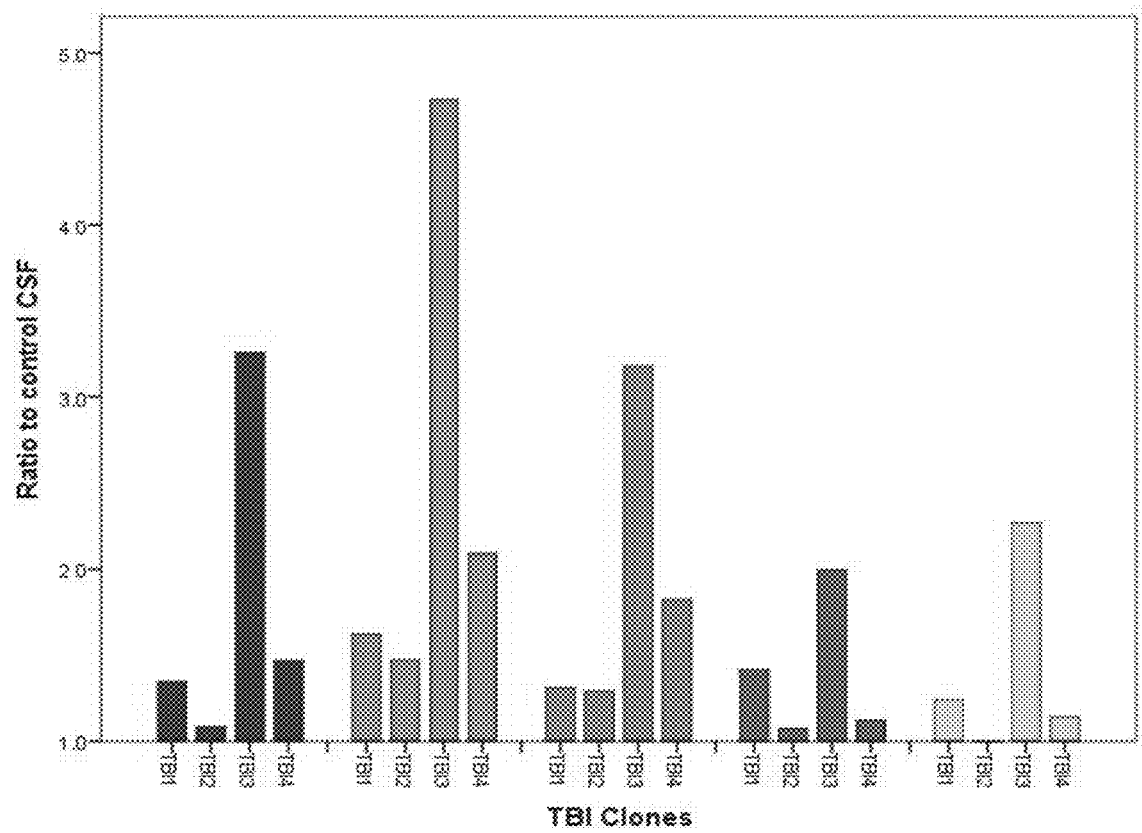
FIG. 14: Indirect ELISA of TBI clones with individual TBI (4 samples) and pooled control CSF. X axis represents the TBI clones and Y axis represents ratio to control CSF. Most of the clones have high levels of binding to TBI samples.
Figure 15:
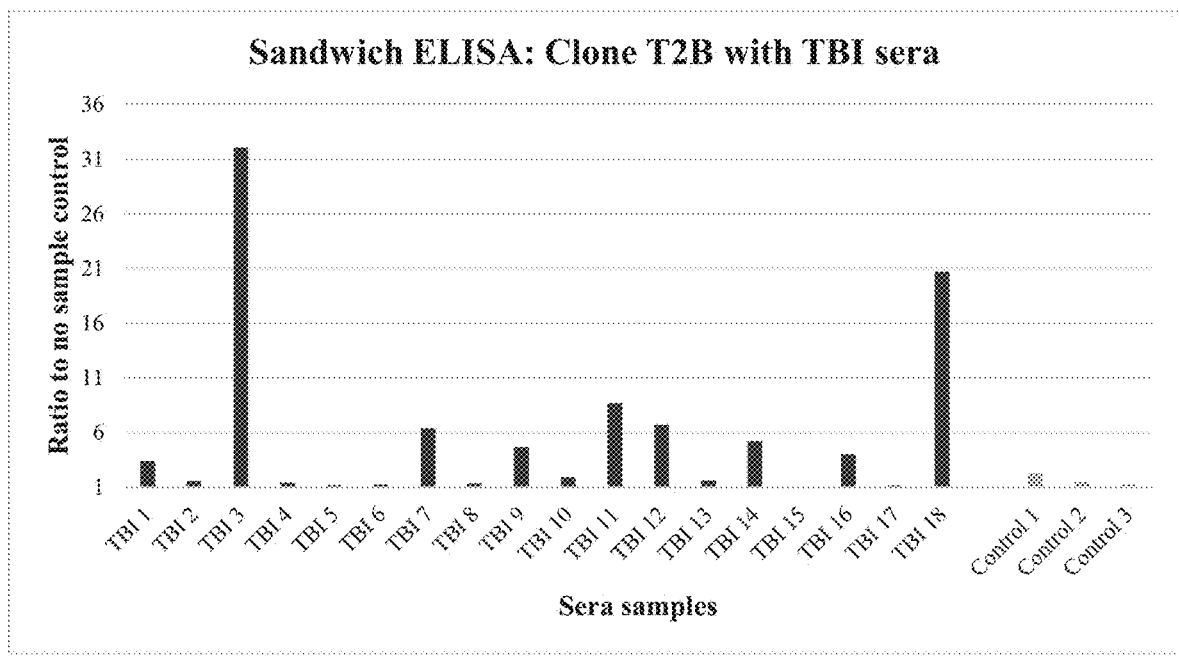
FIG. 15: Sandwich ELISA of clone T2B with 18 TBI sera samples and 3 healthy aged controls. X-Axis represents individual sera samples and Y-Axis represents ratio to no sample control. T2B selectively binds to tau species that possibly circulates in TBI individuals several years after their head trauma when compared to healthy controls.

Clones that gave a high binding ratio to pooled TBI CSF samples were further tested with individual TBI and control CSF samples. As can be seen from FIGS. 14-15, each of the TBI clones were able to selectively pick out all four of the TBI CSF samples over pooled control CSF sample. Almost all the clones had high binding ratio to one of the TBI samples. This could possibly be due to the presence of high levels of TBI specific tau morphologies in this sample which were recognized by the individual clones. Each clone's binding ratio to the individual TBI samples are different indicating that each clone might not necessarily be binding to the same type of tau species. These clones can serve as a tool in recognizing specific tau forms in TBI.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A binding molecule, wherein the binding molecule preferentially recognizes human traumatic brain injury (TBI)-associated tau relative to tau from a healthy normal control and comprises an amino acid sequence at least 96% identical to: (a) an antibody heavy chain variable domain and light chain variable domain of SEQ ID NO:42, or (b) a designed ankyrin repeat protein (DARPin) of SEQ ID NO:44, SEQ ID NO:48, SEQ ID NO:52, or SEQ ID NO:54; wherein differences from the heavy chain variable domain and light chain variable domain of (a) or the DARPIN of (b) are conservative substitutions.

2. The binding molecule of claim 1, wherein the binding molecule comprises the antibody heavy chain variable domain and light chain variable domain of SEQ ID NO:42.

3. The binding molecule of claim 2, wherein the binding molecule is a chimeric antibody, a single-chain antibody, an Fab, or an scFv.

4. A nucleic acid that encodes the binding molecule of claim 1.

5. A vector comprising the nucleic acid of claim 4.

6. A phage comprising the vector of claim 5.

7. A phage comprising a nucleic acid encoding the binding molecule of claim 1.

8. A method of detecting traumatic brain injury (TBI)-associated tau in a subject, the method comprising: (a) incubating a sample from the subject with the binding molecule of claim 1; and (b) detecting an increased amount of TBI-associated tau bound to the binding molecule in the sample from the subject relative to the amount of TBI-associated tau bound to the binding molecule in a healthy normal control sample.

9. The method of claim 8, wherein the binding molecule comprises the antibody heavy chain variable domain and light chain variable domain of SEQ ID NO:42.

10. The method of claim 9, wherein the binding molecule is a chimeric antibody, a single-chain antibody, an Fab, or an scFv.

11. A method for detecting traumatic brain injury (TBI) in a subject, the method comprising: (a) detecting TBI-associated tau in a sample from the subject obtained after head trauma or injury; and (b) comparing the level of TBI-associated tau protein in the sample from the subject with the level of TBI-associated tau protein in a sample from a healthy normal control; wherein detecting TBI-associated tau comprises incubating the sample from the subject with the binding molecule of claim 1; and wherein an elevated level of TBI-associated tau protein in the sample from the subject compared to the level of TBI-associated tau protein in the sample from the healthy normal control indicates TBI.

12. The method of claim 11, wherein the binding molecule comprises the antibody heavy chain variable domain and light chain variable domain of SEQ ID NO:42.

13. The method of claim 12, wherein the binding molecule is a chimeric antibody, a single-chain antibody, an Fab, or an scFv.

14. The method of claim 11, wherein the sample from the subject and the sample from the healthy normal control are blood, serum or cerebrospinal fluid (CSF).

* * * * *